United States Patent
Rasmussen

(10) Patent No.: US 10,517,583 B2
(45) Date of Patent: *Dec. 31, 2019

(54) ARTHOPLASTY SYSTEMS AND METHODS FOR OPTIMALLY ALIGNING AND TENSIONING A KNEE PROSTHESIS

(71) Applicant: G. Lynn Rasmussen, Salt Lake City, UT (US)

(72) Inventor: G. Lynn Rasmussen, Salt Lake City, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 15/351,135

(22) Filed: Nov. 14, 2016

(65) Prior Publication Data

US 2017/0128057 A1    May 11, 2017

Related U.S. Application Data

(63) Continuation of application No. 14/531,749, filed on Nov. 3, 2014, now Pat. No. 9,492,180, which is a
(Continued)

(51) Int. Cl.
| | |
|---|---|
| *A61B 17/02* | (2006.01) |
| *A61B 17/15* | (2006.01) |
| *A61B 17/17* | (2006.01) |
| *A61B 17/72* | (2006.01) |

(52) U.S. Cl.
CPC .......... *A61B 17/025* (2013.01); *A61B 17/154* (2013.01); *A61B 17/155* (2013.01);
(Continued)

(58) Field of Classification Search
CPC .............................. A61B 17/154; A61B 17/025
See application file for complete search history.

(56) References Cited

U.S. PATENT DOCUMENTS

| | | | |
|---|---|---|---|
| 3,696,446 A | 10/1972 | Bousquet et al. | |
| 4,257,129 A | 3/1981 | Volz | |

(Continued)

FOREIGN PATENT DOCUMENTS

| | | |
|---|---|---|
| AU | 2004257445 A1 | 1/2005 |
| CA | 2090189 C | 10/1993 |

(Continued)

OTHER PUBLICATIONS

"Advance Knee System Single Reference Point, Surgical Technique, Traditional, Medial-Pivot, Posterior Stabilized"; © 1998 Wright Medical Technology, Inc.; 15 pages.
(Continued)

*Primary Examiner* — Andrew Yang
(74) *Attorney, Agent, or Firm* — David B. Tingey; Bryant J. Keller; Kirton McConkie

(57) ABSTRACT

A combination of a first assembly for guiding resection of a femur and tibia of a knee joint and a second assembly including femoral and tibial knee components. The combination of the first assembly and the second assembly provides optimal placement and positioning of the femoral and tibial knee components to achieve near-normal knee kinematics and tension. The preparation for and placement of the prosthetic knee components provides medial-pivoting kinematics mimicking that of the natural knee thereby promoting improved outcome for the patient.

17 Claims, 50 Drawing Sheets

Related U.S. Application Data continuation of application No. 13/685,660, filed on Nov. 26, 2012, now Pat. No. 8,876,831, which is a continuation of application No. 12/191,262, filed on Aug. 13, 2008, now Pat. No. 8,317,797, which is a continuation-in-part of application No. 11/349,772, filed on Feb. 8, 2006, now Pat. No. 7,927,336.

(60) Provisional application No. 60/651,102, filed on Feb. 8, 2005.

(52) U.S. Cl.
CPC ........ *A61B 17/157* (2013.01); *A61B 17/1764* (2013.01); *A61B 17/72* (2013.01); *A61B 17/7283* (2013.01); *A61B 2017/0268* (2013.01)

(56) References Cited

U.S. PATENT DOCUMENTS

| | | |
|---|---|---|
| 4,298,992 A | 11/1981 | Burstein et al. |
| 4,355,429 A | 10/1982 | Mittelmeier et al. |
| 4,474,177 A | 10/1984 | Whiteside |
| 4,487,203 A | 12/1984 | Androphy |
| 4,566,448 A | 1/1986 | Rohr, Jr. |
| 4,567,886 A | 2/1986 | Petersen |
| 4,608,052 A | 8/1986 | Van Kampen et al. |
| 4,673,409 A | 6/1987 | Van Kampen |
| 4,714,473 A | 12/1987 | Bloebaum |
| 4,718,413 A | 1/1988 | Johnson |
| 4,769,039 A | 9/1988 | Horber |
| 4,769,040 A | 9/1988 | Wevers |
| 4,778,473 A | 10/1988 | Matthews et al. |
| 4,871,368 A | 10/1989 | Wagner |
| 4,938,762 A | 7/1990 | Wehrli |
| 4,952,213 A | 8/1990 | Bowman et al. |
| 4,955,919 A | 9/1990 | Pappas et al. |
| 4,964,868 A | 10/1990 | Bloebaum |
| 5,041,140 A | 8/1991 | Teinturier |
| 5,074,881 A | 12/1991 | Thull et al. |
| 5,108,396 A | 4/1992 | Lackey et al. |
| 5,108,435 A | 4/1992 | Gustavson et al. |
| 5,171,285 A | 12/1992 | Broderick |
| 5,176,684 A | 1/1993 | Ferrante et al. |
| 5,192,329 A | 3/1993 | Christie et al. |
| 5,217,498 A | 6/1993 | Henssge et al. |
| 5,219,362 A | 6/1993 | Tuke et al. |
| 5,228,459 A | 7/1993 | Caspari et al. |
| 5,271,737 A | 12/1993 | Baldwin et al. |
| 5,282,866 A | 2/1994 | Cohen et al. |
| 5,326,354 A | 7/1994 | Kwarteng |
| 5,326,361 A | 7/1994 | Hollister |
| 5,356,414 A | 10/1994 | Cohen et al. |
| 5,358,530 A | 10/1994 | Hodorek |
| 5,364,401 A | 11/1994 | Ferrante et al. |
| 5,370,703 A | 12/1994 | Willert et al. |
| 5,413,604 A | 5/1995 | Hodge |
| 5,415,662 A | 5/1995 | Ferrante et al. |
| 5,458,649 A | 10/1995 | Spotorno et al. |
| 5,514,143 A | 5/1996 | Bonutti et al. |
| 5,520,695 A | 5/1996 | Luckman |
| 5,549,691 A | 8/1996 | Harwin |
| 5,597,379 A | 1/1997 | Haines et al. |
| 5,649,928 A | 7/1997 | Grundei |
| 5,649,929 A * | 7/1997 | Callaway ............. A61B 17/025 606/87 |
| 5,662,656 A | 9/1997 | White |
| 5,672,178 A | 9/1997 | Petersen |
| 5,681,316 A | 10/1997 | DeOrio et al. |
| 5,688,280 A | 11/1997 | Booth, Jr. et al. |
| 5,688,281 A | 11/1997 | Cripe et al. |
| 5,702,458 A | 12/1997 | Burstein et al. |
| 5,733,292 A | 3/1998 | Gustilo |
| 5,735,904 A | 4/1998 | Pappas |
| 5,824,102 A | 10/1998 | Buscayret |
| 5,860,980 A | 1/1999 | Axelson, Jr. et al. |
| 5,874,123 A | 2/1999 | Park |
| 5,964,808 A | 10/1999 | Blaha et al. |
| 6,004,351 A | 12/1999 | Tomita et al. |
| 6,013,081 A | 1/2000 | Burkinshaw et al. |
| 6,013,103 A | 1/2000 | Kaufman et al. |
| 6,022,377 A | 2/2000 | Nuelle et al. |
| 6,042,609 A | 3/2000 | Giordano et al. |
| 6,056,756 A | 5/2000 | Eng et al. |
| 6,063,091 A | 5/2000 | Lombardo et al. |
| 6,096,082 A | 8/2000 | Stemuller et al. |
| 6,099,570 A | 8/2000 | Livet et al. |
| 6,203,844 B1 | 3/2001 | Park |
| 6,267,762 B1 | 7/2001 | Millard et al. |
| 6,290,704 B1 | 9/2001 | Burkinshaw et al. |
| 6,344,043 B1 | 2/2002 | Pappas |
| 6,355,045 B1 | 3/2002 | Gundlapalli et al. |
| 6,478,799 B1 | 11/2002 | Williamson |
| 6,488,687 B1 | 12/2002 | Masini |
| 6,558,428 B2 | 5/2003 | Park |
| 6,605,293 B1 | 8/2003 | Giordano et al. |
| 6,613,052 B1 | 9/2003 | Kinnett |
| 6,645,215 B1 | 11/2003 | McGovern et al. |
| 6,740,092 B2 | 5/2004 | Lombardo et al. |
| 6,770,078 B2 | 8/2004 | Bonutti |
| 6,852,115 B2 | 2/2005 | Kinnett |
| 7,011,664 B2 | 3/2006 | Haney et al. |
| 7,029,477 B2 | 4/2006 | Grimm |
| 7,104,996 B2 | 9/2006 | Bonutti |
| 7,309,363 B2 | 12/2007 | Dietz |
| 7,374,563 B2 | 5/2008 | Roger et al. |
| 7,558,603 B2 | 9/2009 | Leonard |
| 7,618,422 B2 | 11/2009 | Goodwin |
| 7,740,661 B2 | 6/2010 | Baratz et al. |
| 7,780,672 B2 | 8/2010 | Metzger et al. |
| 7,927,336 B2 | 4/2011 | Rasmussen |
| 7,959,637 B2 | 6/2011 | Fox et al. |
| 7,993,341 B2 | 8/2011 | Grimm et al. |
| 8,043,294 B2 | 10/2011 | Fencl et al. |
| 8,303,597 B2 | 11/2012 | Rasmussen |
| 8,317,797 B2 | 11/2012 | Rasmussen |
| 8,876,831 B2 | 11/2014 | Rasmussen |
| 9,492,179 B2 | 11/2016 | Rasmussen |
| 9,492,180 B2 | 11/2016 | Rasmussen |
| 2007/0162036 A1 | 7/2007 | Schifrine et al. |
| 2007/0293868 A1 | 12/2007 | Delfosse et al. |
| 2008/0177261 A1 | 7/2008 | McMinn |
| 2011/0046744 A1 | 2/2011 | Errico et al. |
| 2014/0277543 A1 | 9/2014 | Fox et al. |
| 2015/0190243 A1 | 7/2015 | Claypool et al. |

FOREIGN PATENT DOCUMENTS

| | | |
|---|---|---|
| DE | 44 23 717 C1 | 1/1996 |
| EP | 0 809 969 A2 | 12/1997 |
| EP | 0 976 636 A2 | 2/2000 |
| EP | 1348382 A2 | 10/2003 |
| FR | 2 806 901 A1 | 10/2001 |
| FR | 2 857 576 | 1/2005 |
| JP | H05041510 U | 6/1993 |
| JP | 11221244 | 8/1999 |
| JP | 2005527294 A | 9/2005 |
| KR | 1019990014833 | 2/1999 |
| WO | 2001/085038 A1 | 11/2001 |
| WO | 2005/006993 A2 | 1/2005 |
| WO | 2006/010871 A1 | 2/2006 |
| WO | 2006/056751 A1 | 6/2006 |
| WO | 2007/092614 A1 | 8/2007 |
| WO | 2008-112996 A1 | 9/2008 |
| WO | 2010/019284 A1 | 2/2010 |
| WO | 2010/019822 A9 | 2/2010 |

OTHER PUBLICATIONS

"Advance Knee Distal Cut First Surgical Technique"; © 2002 Wright Medical Technology, Inc.; 17 pages.
"Advance Anterior Rough Cut, Surgical Technique"; © 2002 Wright Medical Technology, Inc.; 20 pages.

(56) References Cited

OTHER PUBLICATIONS

"Advance Knee Distal Cut First Surgical Technique"; © 2002 Wright Medical Technology, Inc.; 20 pages.

* cited by examiner

ARTHOPLASTY SYSTEMS AND METHODS FOR OPTIMALLY ALIGNING AND TENSIONING A KNEE PROSTHESIS

CROSS-REFERENCE TO RELATED APPLICATIONS

This is a continuation of U.S. patent application Ser. No. 14/531,749, filed Nov. 3, 2014, and entitled ARTHROPLASTY SYSTEMS AND METHODS FOR OPTIMALLY ALIGNING AND TENSIONING A KNEE PROSTHESIS, which is a continuation of U.S. patent application Ser. No. 13/685,660, filed Nov. 26, 2012 and entitled ARTHROPLASTY SYSTEMS AND METHODS FOR OPTIMALLY ALIGNING AND TENSIONING A KNEE PROSTHESIS (now issued as U.S. Pat. No. 8,876,831), which is a continuation of U.S. patent application Ser. No. 12/191,262, filed Aug. 13, 2008 and entitled ARTHROPLASTY SYSTEMS AND METHODS FOR OPTIMALLY ALIGNING AND TENSIONING A KNEE PROSTHESIS (now issued as U.S. Pat. No. 8,317,797), which is a continuation-in-part of U.S. patent application Ser. No. 11/349,772, filed Feb. 8, 2006, and entitled GUIDE ASSEMBLY FOR GUIDING CUTS TO A FEMUR AND TIBIA DURING A KNEE ARTHROPLASTY (now issued as U.S. Pat. No. 7,927,336), which claims priority to U.S. Provisional Patent Application Ser. No. 60/651,102, filed Feb. 8, 2005 and entitled GUIDE ASSEMBLY FOR GUIDING CUTS TO A FEMUR AND TIBIA DURING A KNEE ARTHROPLASTY, each of which is incorporated herein by reference in its entirety.

BACKGROUND OF THE INVENTION

Field of the Invention

The present invention is related to the use of instruments for guiding preparation of a knee for installation of an implant during an arthroplasty, and in particular, to the use of ligaments around the knee and other anatomical features to position the guide instruments and making reference cuts to the tibia and the femur.

Description of Related Art

During a knee arthroplasty, a surgeon typically must gain access to the knee joint in order to perform resections of existing bone and cartilage so as to shape the tibia and femur to fit mating surfaces of the implant. Some arthroplasty procedures seek to minimize the invasiveness of the approach to the knee joint by minimizing the size of the incision in the surrounding soft tissue structure of the knee and the patella. Preserving the soft tissue structure also preserves some of the support provided by these tissues. However, preserving the soft tissues surrounding the knee can be difficult at times due to the need to firmly support the resection guides relative to the bone of the tibia and the femur.

The manner in which the natural knee joint performs is largely affected by the tension in the collateral ligaments of the knee, as well as by the alignment of the articular surfaces of the knee joint relative to the collateral ligaments. In the natural knee joint, the plane of the articular surfaces of the femur and the tibia bisects the collateral ligaments at an optimal, physiological position. This optimal, physiological position enables the knee joint to flex and extend in a balanced and properly aligned manner. Exemplary arthroplasty procedures resection the femur and the tibia, yet preserve the optimal, physiological position of the knee joint when fitted with a prosthesis.

Preservation of the ligamentous and other soft tissue structures around the knee can provide a reference point for accurately positioning the tibial and femoral components of the knee implant, in particular when said structure is in tensed or otherwise loaded condition. For example, ligament tensions can be used to guide placement of resection guides. Conversely, preservation of the soft tissue structures requires balancing of the forces exerted by the soft tissues to promote normal kinematics in the knee and normal patellar tracking. Therefore, ligament forces can play a significant role in restoring normal function to a knee. Generally, therefore, reductions in the invasiveness of the knee arthroplasty procedure combined with improvements in the positioning and installation of knee components can result in a better overall surgical outcome for the patient.

It would therefore be advantageous to have instrumentation for guiding resection of the femur, tibia and other structures in the knee during a knee arthroplasty that works well with minimally invasive approaches to the tibia and femur. It would be further advantageous if the instrumentation assisted the balancing of forces between the knee implant components and the preserved ligamentous and soft tissue structures for improved function of the knee implant. Also, it would be advantageous to have instrumentation for guiding resection that uses the ligamentous structure of the knee to guide placement of the instrumentation and the resulting optimal alignment and physiological positioning of the knee prosthesis.

BRIEF SUMMARY OF THE INVENTION

The present invention meets the above needs, and achieves other advantages, by providing an assembly for guiding resection of a femur and tibia of a knee joint in preparation for installing femoral and tibial knee components. The components of the present invention may be configured for use in both total knee replacement and unicompartmental, or partial knee arthroplasty. Embodiments of the present assembly can include tibial and femoral IM rods which are connected through a torque bolt that allows controlled adjustment of the distraction of the tibia and femur during cut positioning in a range of flexion angles. Also, the assembly is usable with relatively small, noninvasive approaches to the knee joint by way of relatively narrow, low profile components that attach to tibial and femoral IM rods. Further, the assembly includes several quick-release components to allow fast assembly and disassembly in a surgical setting. Each of these aspects, along with the ability of the assembly to accurately guide initial reference cuts to the tibia and femur, promotes an improved outcome for the patient.

An assembly of one embodiment of the present invention includes femoral and tibial IM rods, a flexion cutting guide, an extension cutting guide and a selection of selectively lockable components. Each of the IM rods includes a shaft portion that is configured to extend within the IM canal of the femur or tibia. The femoral IM rod also includes a femoral mount on an end of the shaft that is configured to extend away from the femur when the shaft is in the femoral IM canal. Similarly, the tibial IM rod includes a tibial mount on an end of the shaft that is configured to extend away from the tibia when the shaft is in the tibial IM canal. Each of the mounts is configured to attach to one or more of the selectively lockable components. The flexion and extension cutting guides define one or more slots wherein the slots are configured to guide the use of cutting and other instruments to make preparatory cuts to the femur and/or the tibia with the knee in flexion and extension. Each of the cutting guides is configured to attach to one or more of the selectively lockable components so as to be supported by the femoral and tibial IM rods. The selectively lockable components are configured to attach to the femoral and tibial IM rods, to have at least one portion with a relatively small cross section extending anteriorly or anterior-medial out of the knee joint compartment and to attach to the flexion and extension cutting guides and support and limit the motion thereof.

In one aspect, the femoral mount has a cylindrical shape that extends in an anterior-posterior direction between the femoral condyles and includes a central opening and a plurality of gauge marks extending along its outside surface. The central opening may also include an anterior anti-rotation portion (e.g., a hexagonal shaped portion) and a larger diameter cylindrical portion. The tibial mount can include or support a flexion bolt with a threaded shaft at one end configured to extend into an opening in the tibial IM shaft, a bushing at the other end and an exterior hexagonal flange in between the ends. The bushing is configured to extend into the cylindrical portion and also contains an interior hexagonal bore. The hexagonal flange is configured to allow gripping by an external torque wrench or internal torque driver to urge the femoral mount away from the tibial mount (by turning of the threaded shaft) and distract the tibia and femur to a desired torque reading. This allows the surgeon to apply the appropriate amount of tension to the ligamentous structure as defined by said surgeon and recorded for comparison later in the technique.

Included in an exemplary embodiment of the selectively lockable components is a first locking mechanism that has an arm, a plunger assembly and an anti-rotation extension, defined in this instance as a hex. The arm has an elongate portion extending away from a head portion. Also extending from the head portion is the hex-shaped anti-rotation extension. Defined through the head portion and hex extension is an opening that is configured to receive a shaft of the plunger assembly. The plunger assembly includes a thumb press at one end of the shaft and an anti-rotation feature similar to anti-rotation extension, defined in this instance as a hexagonal tip at the other end of the shaft that extends out of the hex extension. Also, the shaft includes a peg that extends into a helically shaped slot defined in the head portion. A spring extends between the head portion and the thumb press. Depression of the thumb press advances the shaft, while the peg and helical slot cause the shaft to rotate, and the flats of the hexagonal tip to align with the hex extension. This allows the hexagonal tip and hex extension to become concentric and to be inserted into the anterior hex portion of the central opening of the femoral mount. In addition, the hexagonal tip is configured to extend out of the hex portion of the opening and into the cylindrical portion, and to rotate (due to the helical slot and peg) into an eccentric position upon release of the thumb press, thereby locking the locking mechanism into the femoral mount. When attached, the head portion of the arm extends proximally out of the knee joint compartment and the elongate portion extends anteriorly (with respect to the tibia) through the surgical incision.

A flexion guide support member of the assembly of the present invention includes a slider member and a ratchet bar. The slider member is configured to attach to, and slide along, the elongate portion of the arm of the first locking mechanism, such as by having an opening defined therein matching the cross-section of the elongate portion. The ratchet bar is configured to extend toward a plane defined by the tibial plateau. Preferably, when assembled, the femoral mount, first locking mechanism and flexion guide support member roughly form a U-shape that is relatively narrow in the medial-lateral direction to allow its use with narrow incisions.

Also included in the selectively lockable components is a quick release mechanism that is configured to slide along and lock to the ratchet bar of the flexion guide support member. For example, the quick release mechanism may define an opening configured to extend and slide along the ratchet bar, and a locking pin that is spring loaded to extend into a portion of the ratchet to stop the sliding motion. The locking pin is spring biased, but can be overcome with a manual draw pull (for example) to allow further sliding or repositioning of the quick release mechanism. The quick release mechanism may also include a spring-biased locking lever that, along with an engagement member of the quick release mechanism, can extend into an opening and lock to the flexion cutting guide. Depressing the locking lever again easily releases the flexion cutting guide after k-wire or other fasteners have been used to secure the flexion cutting guide in place to the tibia or femur. This allows the resection guide to translate toward the proximal tibia and away from the tensioning assembly with the knee in flexion.

Once the flexion resection guide is fixed to the proximal tibia, the resection guide has a plurality of slots for which to resect multiple components of the femur and tibia, most notably a measured proximal tibial resection and a posterior condylar resection. Making these resections with the knee in tension at 90 degrees will allow the user to theoretically make a tensed flexion gap resection.

The selectively lockable components may also include components configured to attach to the femoral and tibial IM rods when the knee is in extension. For example, the components may include a cannulated extension bolt, a tibial angulation guide, an extension guide support member and a second locking mechanism. The tibial angulation guide is configured to attach to the tibial IM rod through the cannulated extension bolt which is, in turn, coupled to the tibial IM rod and extend around the femoral mount, such as by having a block defining an arc-shaped channel that is configured to receive the cylindrical outer surface of the femoral mount. Included on the tibial angulation guide are a plurality of gauge marks that, when correlated to gauge marks on the outer surface of the femoral mount, register an amount of valgus angulation of the tibia with respect to the femur. The tibial angulation guide may be configured to extend into the bushing of the bolt described above, or to have its own threaded shaft and hexagonal flange allowing it to be used to distract the tibia and femur in extension to a torque value corresponding to the torque value previously measured with the knee in flexion.

The extension guide support member is configured to have a relatively narrow profile and extend anteriorly out of the joint compartment through the incision providing access thereto. For example, the extension guide support member may include a mounting portion that is cylindrical and defines a cylindrical opening and a support arm that is configured to extend proximally from the mounting portion. The second locking mechanism is generally configured similar to the first, except it lacks the fixed elongate portion of the arm. Rather, it includes a cylindrical head portion that is configured to extend through the cylindrical opening of the mounting portion of the extension guide support member so as to connect the extension guide support member to the femoral mount while allowing said support member to rotate in a desired position independent of the previously selected valgus angle.

The extension guide support member also includes a support arm that is configured to extend proximally from the mounting portion when the mounting portion is attached to the femoral mount using the second locking member. The extension cutting guide is configured to slidably attach over the support arm, such as via a channel defined in its body. Also, the extension cutting guide preferably includes a swivel arm that can be swung into an abutting relationship with the tibial plateau and the plateau flange of the tibial mount to provide an additional reference point for making a femoral resection with the knee in extension. The extension cutting guide, similar to the flexion cutting guide, may also define a plurality of fixation openings allowing fasteners to extend therethrough and attach the extension cutting guide to the tibia or femur. This allows removal of the selectively lockable components to provide room for the cuts to the tibia and/or the femur.

The swivel arm, once referenced off the proximal tibial resection, will allow the extension cutting guide to make a pre-determined resection of the distal femur. Resecting with the knee tensed in the extended position will allow the user to make a balanced extension gap resection when compared with the tensed resections made with the knee previously positioned in flexion.

The assembly of the present invention has many advantages. For example, it provides a relatively narrow and low profile collection of locking components that securely attach cutting guides to tibial and/or femoral IM rods. This provides a robust guide to reference cuts being made to the tibia and the femur with an approach to the joint that minimizes invasiveness. Further, many of the components, such as the first and second locking mechanisms and the quick release mechanism, facilitate quick assembly, easy adjustment and quick disassembly for improved efficiency. Additionally, the use of the flexion bolt in flexion and the extension bolt in extension, combined with the other components of the tensioning assembly, allow the tibia and femur to be distracted under a matching amount of tension in flexion and extension to ensure a better fit for the tibial and femoral knee replacement components throughout a range of flexion. Spacers, as well as limited radial movement of the tensioning assembly components further allow the knee to adjust to accommodate the natural physiology of the patient's knee throughout the tensioning and resection processes. Thus, the described procedures and assemblies allow the surgeon to adjust the amount of valgus angulation of the tibia as desired to match the anatomy of the patient.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

An assembly 10 of the present invention for facilitating preparation of a knee joint, including guiding positioning of cuts to a femur 11 and tibia 12 of the knee joint, for later mating with femoral and tibial knee replacement components, is shown in the accompanying figures. Generally, the assembly 10 includes various components selected and arranged to attach to a reference point inside the knee joint compartment (such as one or more intramedullary (IM) rods), extend through a relatively narrow, small or noninvasive approach defined in the soft-tissues of the knee and attach outside the knee to a selection of resection guides.

Anatomical directions as used herein are in reference to the knee during the preparatory surgery and correspond to the illustrated embodiment of the assembly 10. However, depending upon the handedness of the knee, or variations in individual morphology and ligamentous structure, these directions could vary and should not typically be considered limiting.

The assembly 10 can be configured to be applied at different knee flexion angles to facilitate positioning of the components throughout the range of flexion or extension. Illustrated herein are components of the assembly 10 for guiding cuts and preparation of the knee at two different flexion angles, namely 90° and full extension. However, the components can be adjusted or configured, or other components employed within the spirit and scope of the present invention, to extend through relatively non-invasive approaches to the knee joint at any range of flexion be it hyper-extension, 30°, 45°, 60°, etc., through to hyper-flexion.

Figure 1:
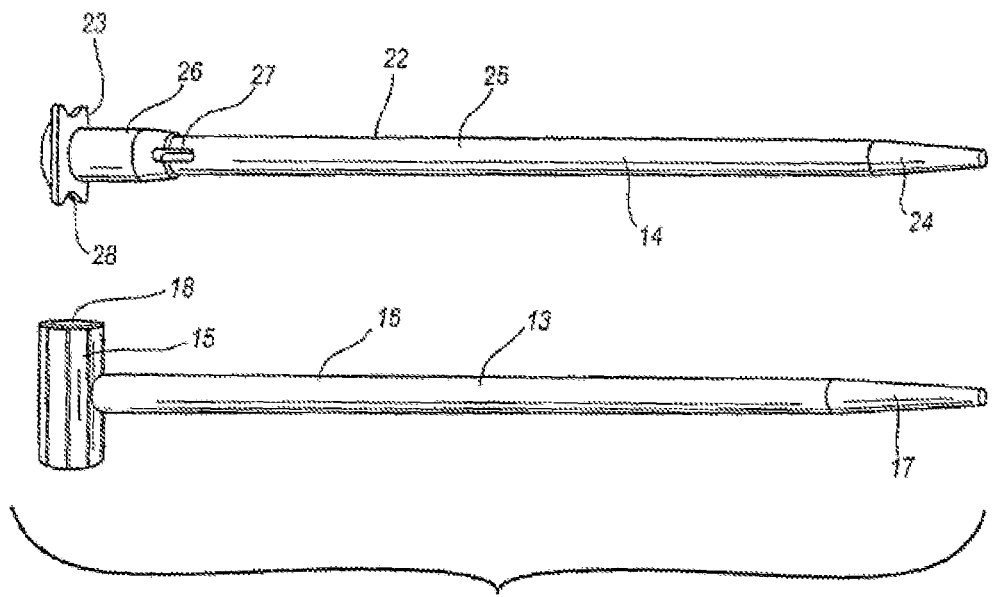
FIG. 1 is a plan view of a tibial intramedullary (IM) rod and femoral IM rod of an assembly of one embodiment of the present invention.
Figure 2:
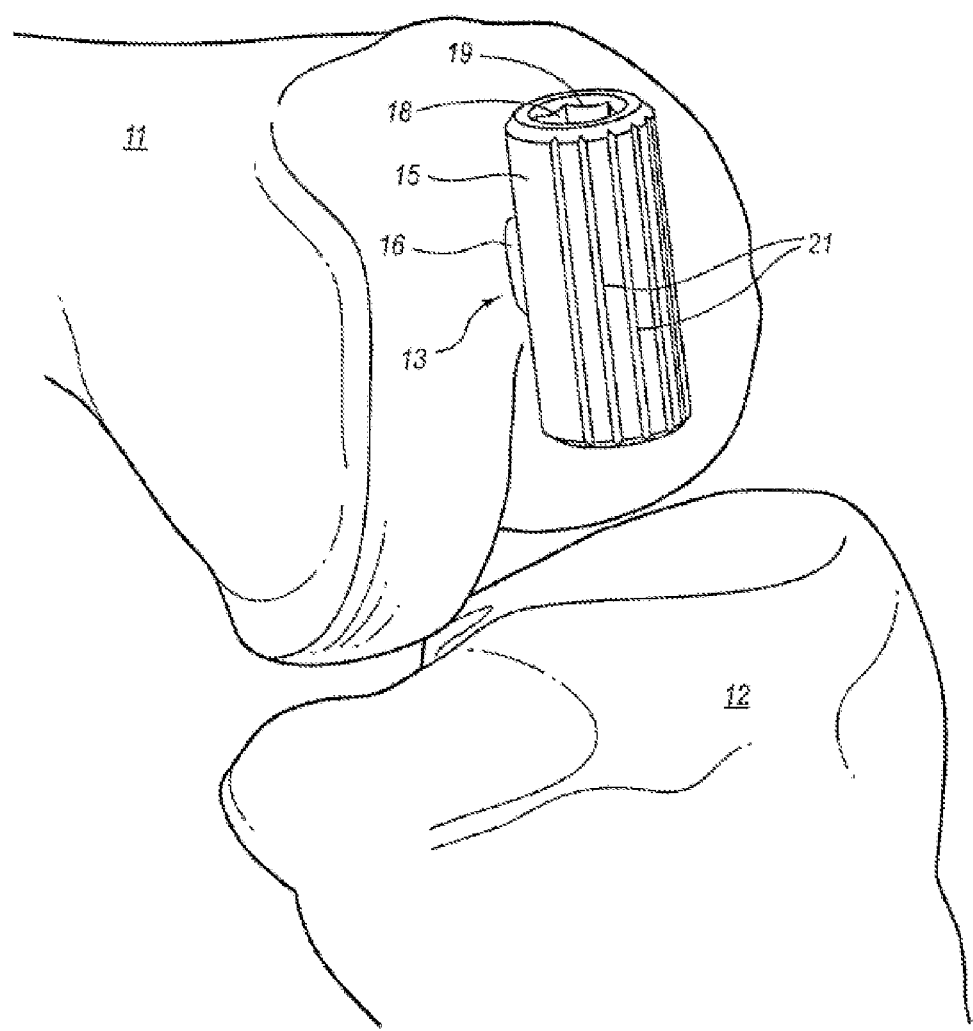
FIG. 2 is a perspective view of the femoral IM rod of FIG. 1 inserted into a femur.

In the illustrated embodiment, the assembly 10 includes two IM rods, a femoral IM rod 13 and a tibial IM rod 14 that provide a reference point for supporting the remainder of the assembly 10 with the knee in flexion, in this case 90° of flexion. The femoral IM rod 13 includes a femoral mount 15 and a main shaft 16, as shown in FIG. 1. The main shaft 16 of the femoral IM rod 13 is preferably an elongate, relatively rigid shaft that, when installed, extends within the IM canal of the femur 11 in a proximal-distal direction, as shown in FIG. 2. The main shaft 16 can include structure that facilitates its insertion into the femur 11, such as a tapered end 17. Preferably, the main shaft 16 is constructed of a relatively rigid material, such as a hard plastic, stainless steel, titanium or other metal or material that is capable of insertion into bone without damage and of stably supporting the femoral mount 15.

Figure 3:
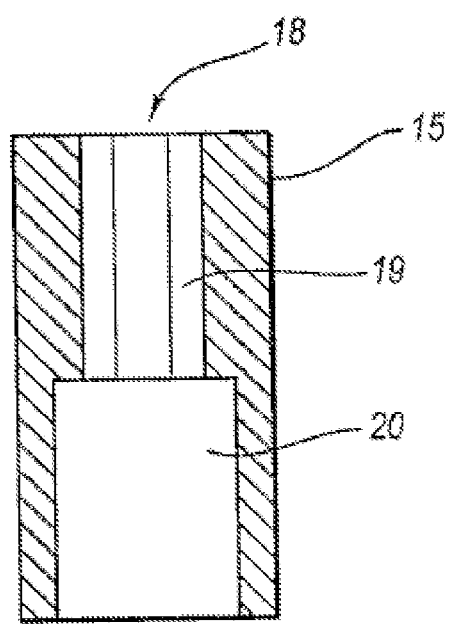
FIG. 3 is a cross-section of a femoral mount of the femoral IM rod shown in FIG. 2.

Attached to the distal end of the main shaft 16, opposite the tapered end 17, is the femoral mount 15. Generally, the femoral mount has a cylindrical shape with an axis extending perpendicular to a long axis of the main shaft 16. Defined along the axis of the femoral mount 15 is a central opening 18, as shown by the cross-sectional view of the femoral mount in FIG. 3. The central opening includes two portions, an anti-rotation portion, in this instance a hex portion, 19 and a cylindrical portion 20 which allow locking of other components of the assembly 10 to the femoral mount 15, as will be described in greater detail below. Regardless, once the femoral IM rod 13 is installed, the femoral mount 15 and its central opening 18 preferably extend in an anterior-posterior direction along the femoral notch between the femoral condyles. Defined on the outer cylindrical surface of the femoral mount 15 is a plurality of longitudinally extending gauge marks 21 that aid in positioning of the tibial and femoral components, as will be described in more detail below.

Figure 4:
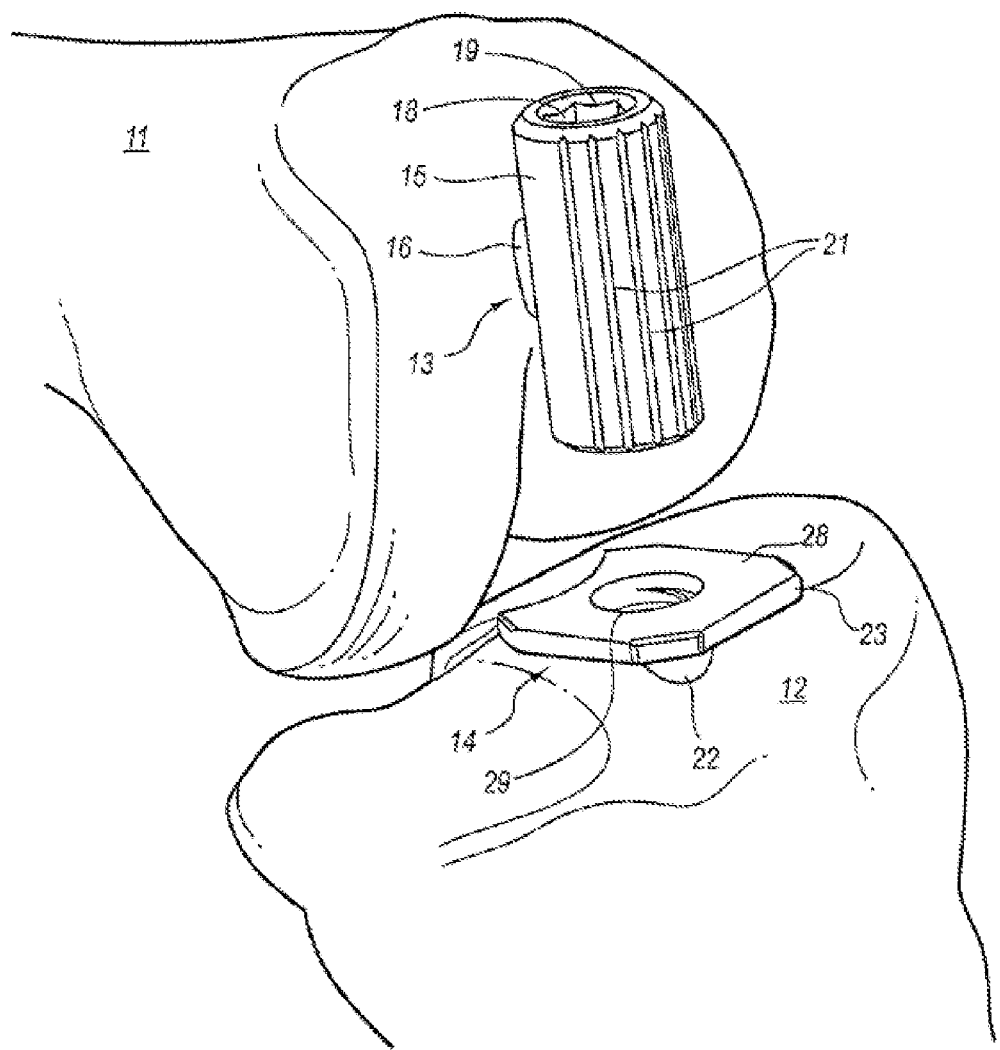
FIG. 4 is a perspective view of a femoral and tibial IM rods of FIG. 1 inserted in the femur and tibia of a knee, respectively.

As shown in FIGS. 1 and 4, the tibial IM rod 14 includes a main shaft 22 supporting a tibial mount 23. Similar to the main shaft 16 of the femoral IM rod 13, the main shaft 22 has an elongate structure with a tapered distal end 24 to facilitate its insertion into the IM canal of the tibia. However, the main shaft 22 preferably includes one or more flutes 25 extending along its length in order to further facilitate insertion and to resist rotation within the IM canal of the tibia. These flutes may also, optionally, be included on the main shaft 16. Defined in the main shaft 22 at its proximal end is an opening 27 that extends into the flutes 25. These openings further facilitate insertion into the IM canal of the tibia. As with the main shaft 16 of the femoral IM rod 13, the main shaft 22 may be constructed of a range of relatively rigid materials to provide firm support for the tibial mount 23. In some embodiments of the current invention, the main shaft 22 of the tibial IM rod is truncated to form a short extension for engaging an opening in the upper surface of the tibia. As such, the tibial IM canal is not accessed but rather the tibial mount 23 and the truncated tibial IM rod primarily engage and interface with the external surface of the tibia. In other embodiments, the tibial mount 23 is provided without a tibial IM rod, such that a flat surface of the tibial mount 23 seats directly on the resectioned surface of the tibia. As such, the interface between the tibial mount 23 the tibia is completely extramedullary. In these embodiments, the position of the tibial mount 23 with respect to the tibia is maintained by the perpendicular compression force between the tibial mount 23 and the tibia. In other embodiments, the flat surface of the tibial mount 23 is modified to include a plurality of spikes which further interface with the resectioned tibial surface to prevent undesirable movement of the tibial mount component 23 during tensioning.

Included in the tibial mount 23 are a thickened cylindrical portion 26 and a plateau flange 28, as shown in FIG. 4. The cylindrical portion 26 is preferably sized to fit the IM canal of the tibia 12. The cylindrical portion is connected at its distal end to the main shaft 22 and at its proximal end supports the plateau flange 28. The plateau flange extends outward at right angles from the cylindrical portion 26 and has three flat sides and one crescent-shaped side. The crescent shaped side is a cutout to provide room for the anterior cruciate ligament prior to resection of the proximal tibia. The flat sides can further aid in guide positioning and cutting, such as during a tibial compartmental resection in a unicondylar arthroplasty procedure wherein only a single condyle and a portion of the tibial plateau are reconstructed.

Figure 5:
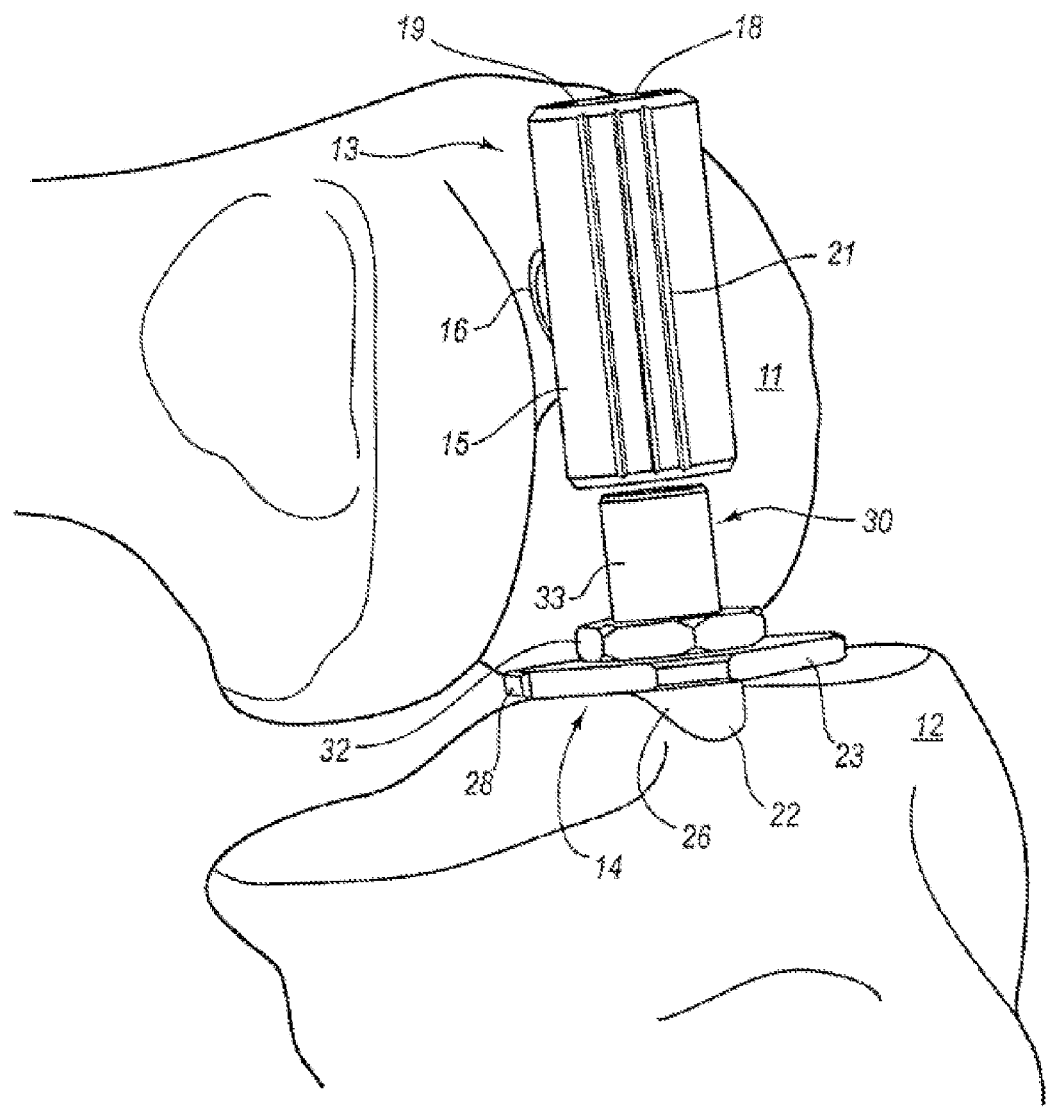
FIG. 5 is a perspective view of a bushing extending from an extension bolt of the assembly of the present invention wherein the extension bolt is coupled to the tibial IM rod of FIG. 1.
Figure 6:
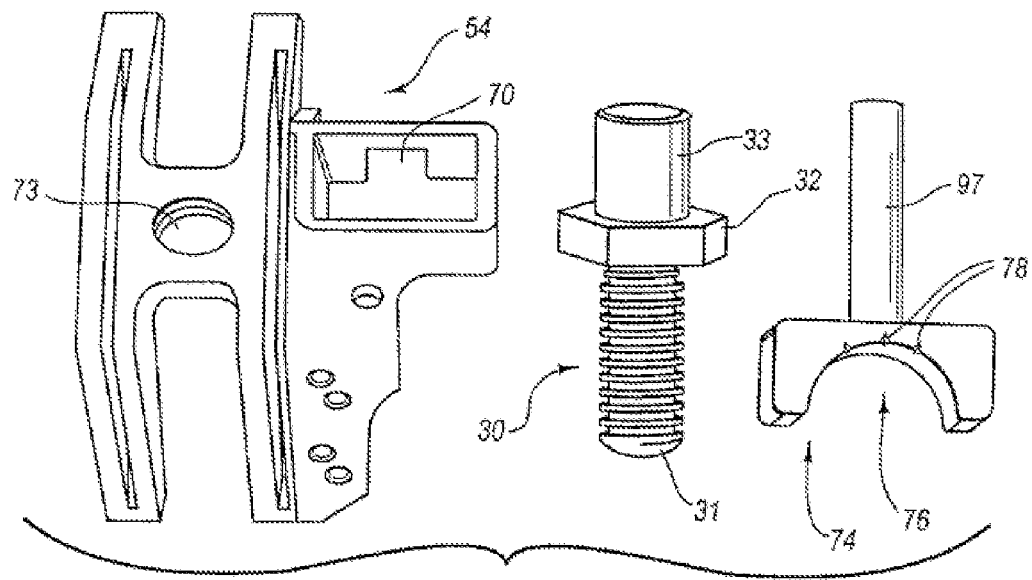
FIG. 6 is a plan view of the extension bolt of FIG. 5 and of a tibial angulation guide and flexed knee cutting guide of the assembly of the present invention.

A threaded opening 29 extends into the tibial mount 23 and provides a coupling attachment for the flexion bolt 30, which includes a threaded shaft 31, a hex flange 32 and a bushing 33, as shown in FIGS. 5 and 6. The threaded shaft 31 has a plurality of threads and extends away from the hex flange 32, while the bushing 33 is a smooth, cylindrical shaft that extends opposite the threaded shaft from the other side of the hex flange 32. The hex flange 32 is shaped to allow gripping by a torque or other wrench to provide motivation for advancement of the threaded shaft 32.

Figure 7:
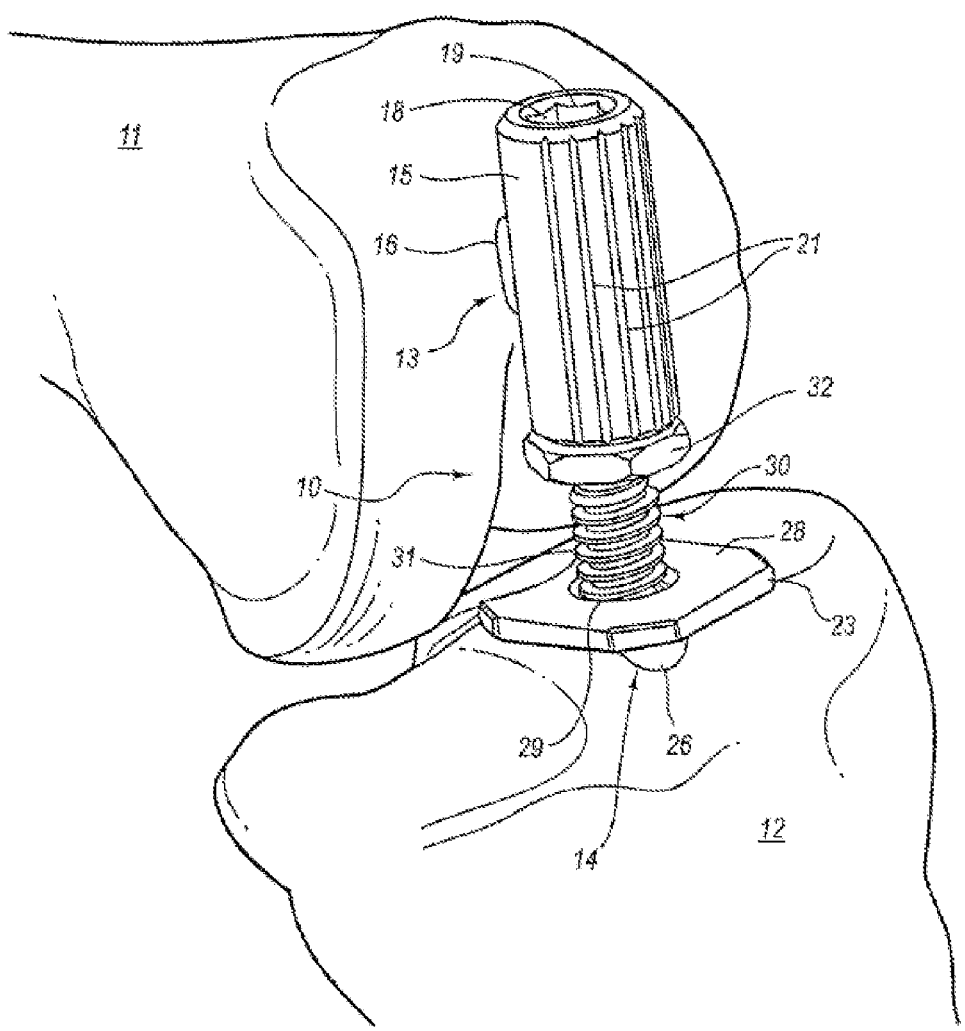
FIG. 7 is a perspective view of the bushing and IM rods of FIG. 5, wherein the bushing of the extension bolt is advanced to connect the IM rods.

The threaded shaft 31 is configured to be advanced into the threaded opening 29 of the tibial mount 23 until it is flush with the plateau flange 28 thereby positioning the bushing 33 at its lowest profile position, as shown in FIG. 5. This position allows the femur 11 and femoral mount 15 extending therefrom to be slipped into position above the bushing 33. Then, the torque wrench is used to reverse the advancement of the threaded shaft 31 until the bushing 33 engages the cylindrical portion 20 of the central opening 18 in the femoral mount 15, as shown in FIG. 7. Advancement is reversed until a pre-selected torque measurement is reached on the torque wrench, or adequate tension of the ligamentous structure is obtained. Once the appropriate ligament tension is obtained, this torque value is recorded for comparison later in the technique. The resulting assembly emulates a static linkage of the femur and tibia with the knee in flexion (e.g., at 30°, 60°, or 90° of flexion or increments therebetween) from which the surgeon can reference subsequent resection instruments as described below.

Figure 8:
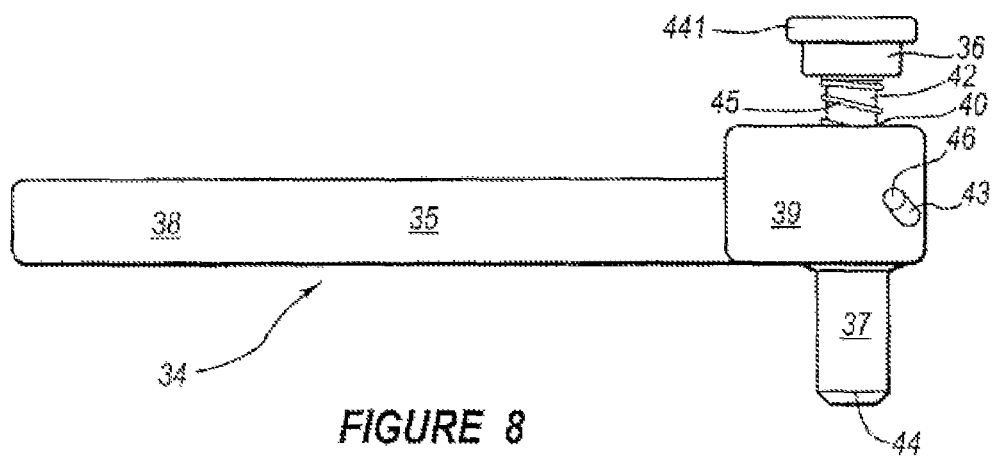
FIG. 8 is a side elevation view of a first locking mechanism of the assembly of the present invention.
Figure 9:
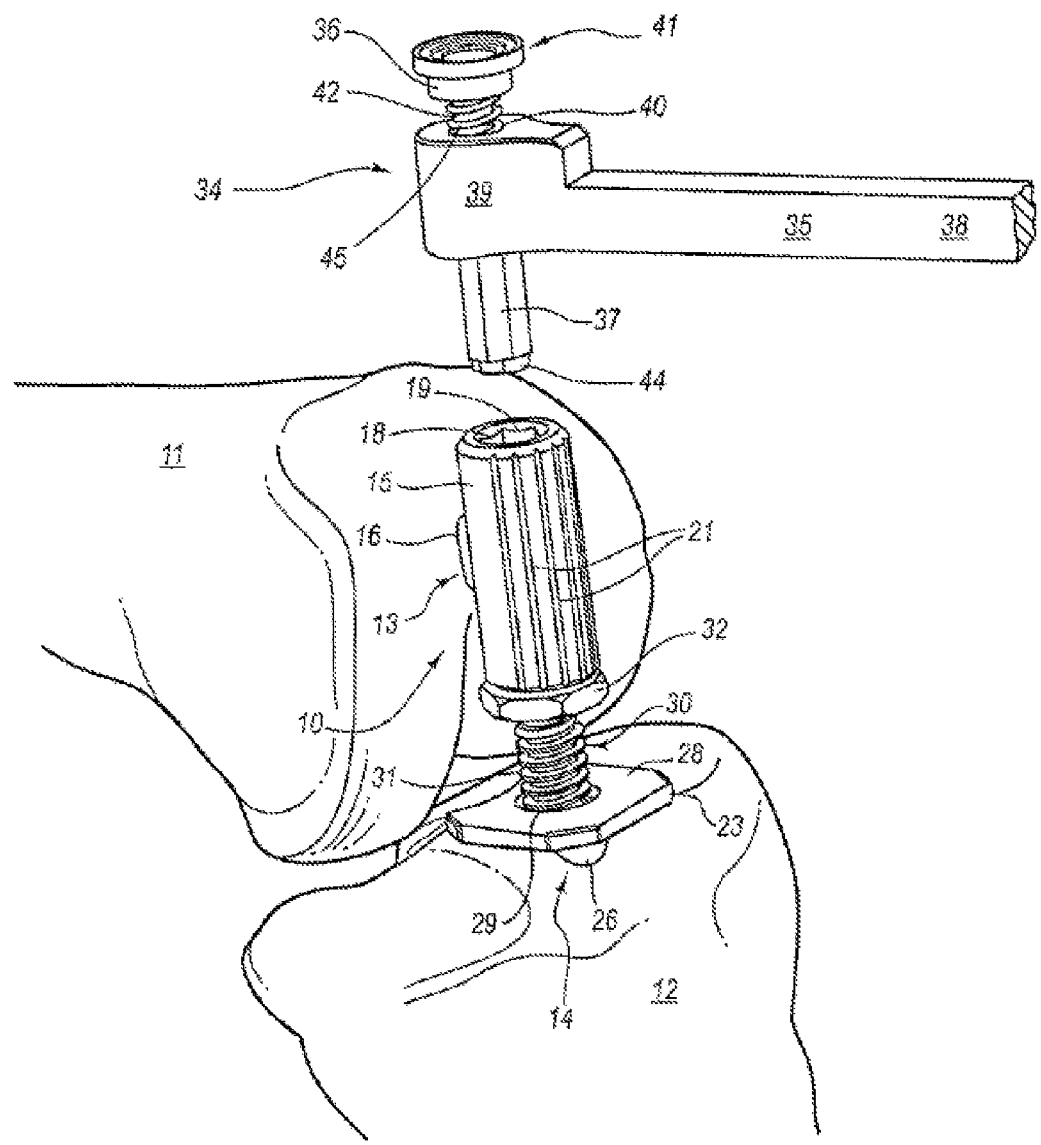
FIG. 9 is a perspective view of the first locking mechanism being connected to the assembled IM rods and bolt of FIG. 7, torqued to a desired load.

Also included in the assembly 10 is a quick connect locking mechanism 34 that connects into the hex portion 19 of the central opening 18, as shown in FIGS. 8 and 9. Included in this embodiment of the locking mechanism are a static outrigger arm 35, a spring-biased plunger 36 and a static clocking extension 37 which emulates the anti-rotation feature 19, and in this instance has a hexagonal shape. The arm 35 has an elongate portion 38 and a rounded head portion 39. The elongate portion 38 of the arm 35 has a square cross-section and extends from the rounded head portion 39 which has a partially cylindrical shape with a pair of opposing flats at its ends. Extending from one of the flats of the rounded head portion is the hex extension 37. The hex extension 37 has a hexagonal cross-section configured to snugly fit within the hex portion 19 of the central opening 18 defined in the femoral mount 15. As shown in FIG. 8, defined in one rounded surface of the head portion 39 is a helically extending slot 43 which, as will be described below, guides motion of the plunger 36.

Defined through the rounded head portion 39 and the hex extension 37 is a cylindrical opening 40 through which the plunger 36 extends. In particular, the plunger 36 includes a thumb press 41, a shaft 42, a spring 45 and rotating extension 44 which emulates the anti-rotation feature 37, in this instance is a hex, but could be any non-cylindrical shape, such as square, triangle or ellipse, capable of limiting rotation. The thumb press 41 is positioned at one end of the plunger 36 and has the shape of a circular disk with ridges to promote pressing with a thumb. Subjacent the thumb press 41 is the spring 45 which is preferably in the shape of a coil and extends around the shaft 42 and between the thumb press and head portion 39 so as to bias them apart.

The shaft 42 includes a peg 46 that extends perpendicular to the shaft and into the helical slot 43 defined in the head portion 39, as shown in FIG. 8. Thus, depression of the thumb press 41 advances the shaft 42 within the opening 40 in the head portion 39, and also results in rotation of the shaft as the peg 46 fixed thereto helically travels in the helical slot 43. The hexagonal end 44 of the plunger 36 is fixed to the end of the shaft 42 opposite the thumb press 41, extends along a free end of the hex extension 37 and has a hexagonal shape and size matching that of the hex extension 37.

Figure 10:
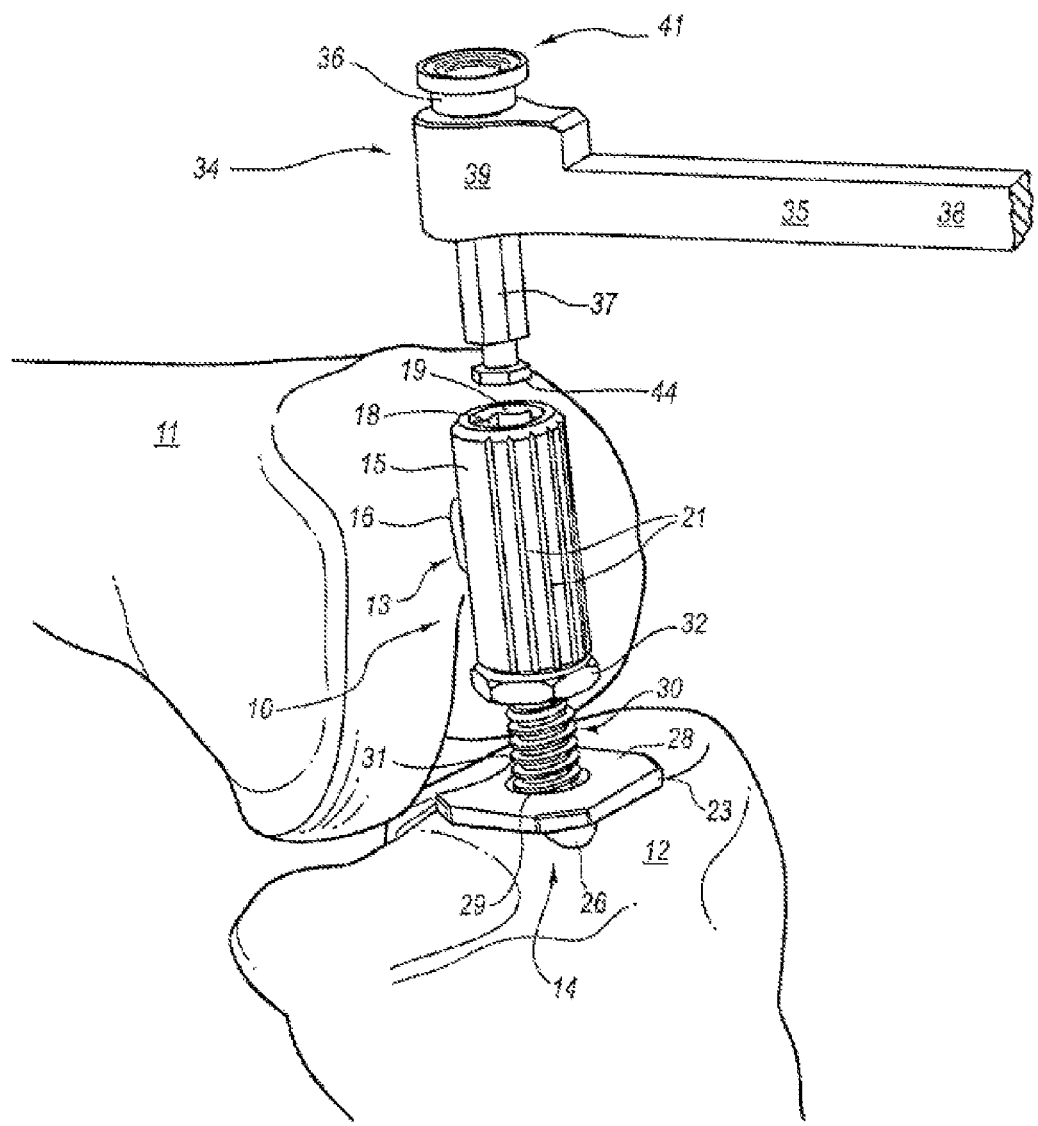
FIG. 10 is another perspective view of the first locking mechanism in the unlocked position, assembled IM rods and bolt of FIG. 9, torqued to a desired load.
Figure 11:
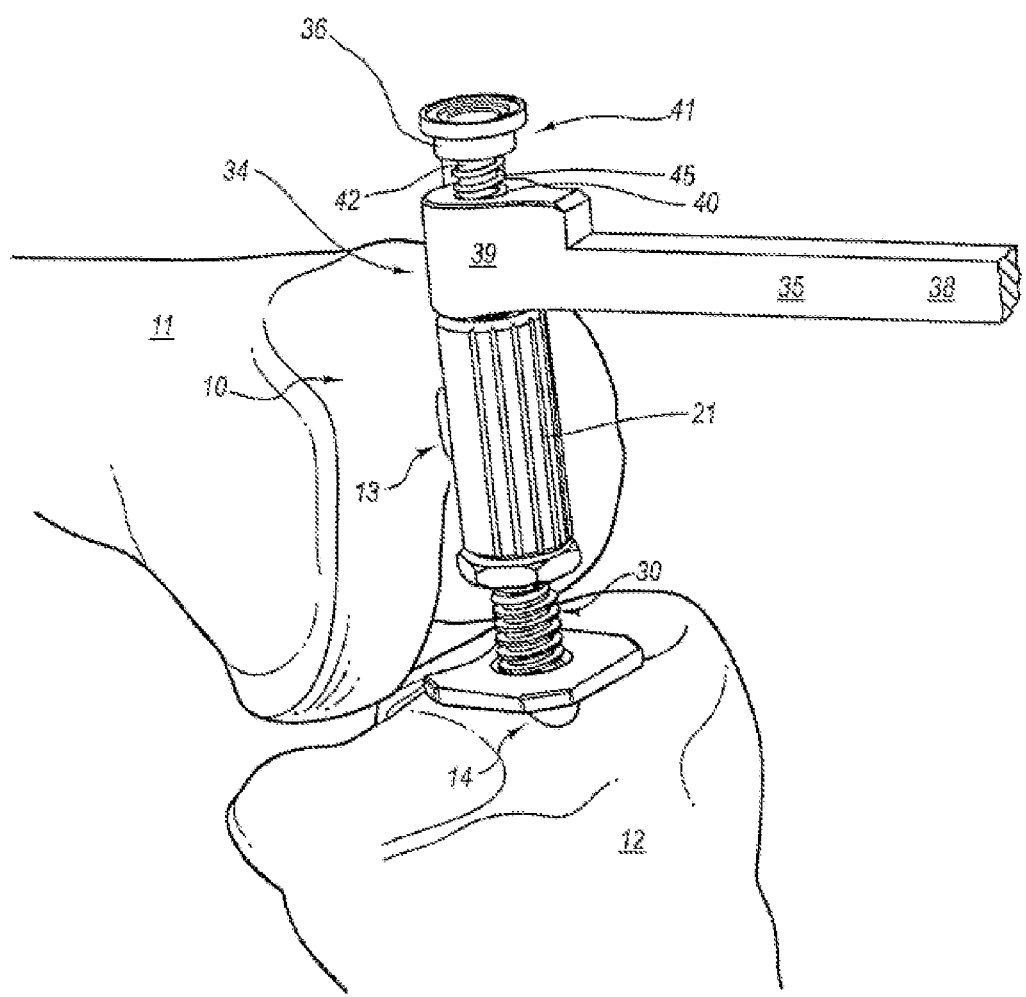
FIG. 11 is yet another perspective view of the first locking mechanism assembled and locked to the IM rods and extension bolt of FIG. 9, torqued to a desired load.

Due to its connection to the shaft 42, depression of the thumb press 41 also causes rotation of the hexagonal end 44 of the plunger 36 until the flats of the hexagonal end match the orientation of the flats of the hex extension 37, as shown in FIG. 10. Matching of this orientation allows insertion of the hex extension 37 and the hexagonal end 44 into the hex portion 19 of the central opening 18 of the femoral mount 15, as shown in FIG. 11. Once the thumb press 41 is released, the spring 45 biases the thumb press, shaft 42 and hexagonal end 44 upwards, causing the flats of the hexagonal end to return to their non-matching, out-of-phase position (shown in FIG. 9) with respect to the flats of the hexagonal extension 37.

At this point, the hexagonal end 44 of the plunger 36 resides in the cylindrical portion 20 of the central opening 18 and, due to its non-matching position, cannot be withdrawn through the hex portion 19 of the central opening. As a result, the locking mechanism 34 becomes rotationally and translationally locked with respect to the femoral mount 15 and the femoral IM rod 13. Once locked in place, the arm 35 of the locking mechanism 34 extends anteriorly outward from the femoral mount 15 and the condyles of the femur 11. Notably, the combination of the relatively narrow femoral mount 15 and narrow, elongate structure of the arm 35 allows passage through relatively small surgical approach openings, facilitating use of the assembly 10 with less invasive procedures. For example, a modified mid-vastus, medial mid-vastus or subvastus approach could be used with a small 8-10 cm cut which allows avoidance of a release of the quadriceps from the anterior tibia.

Figure 12:
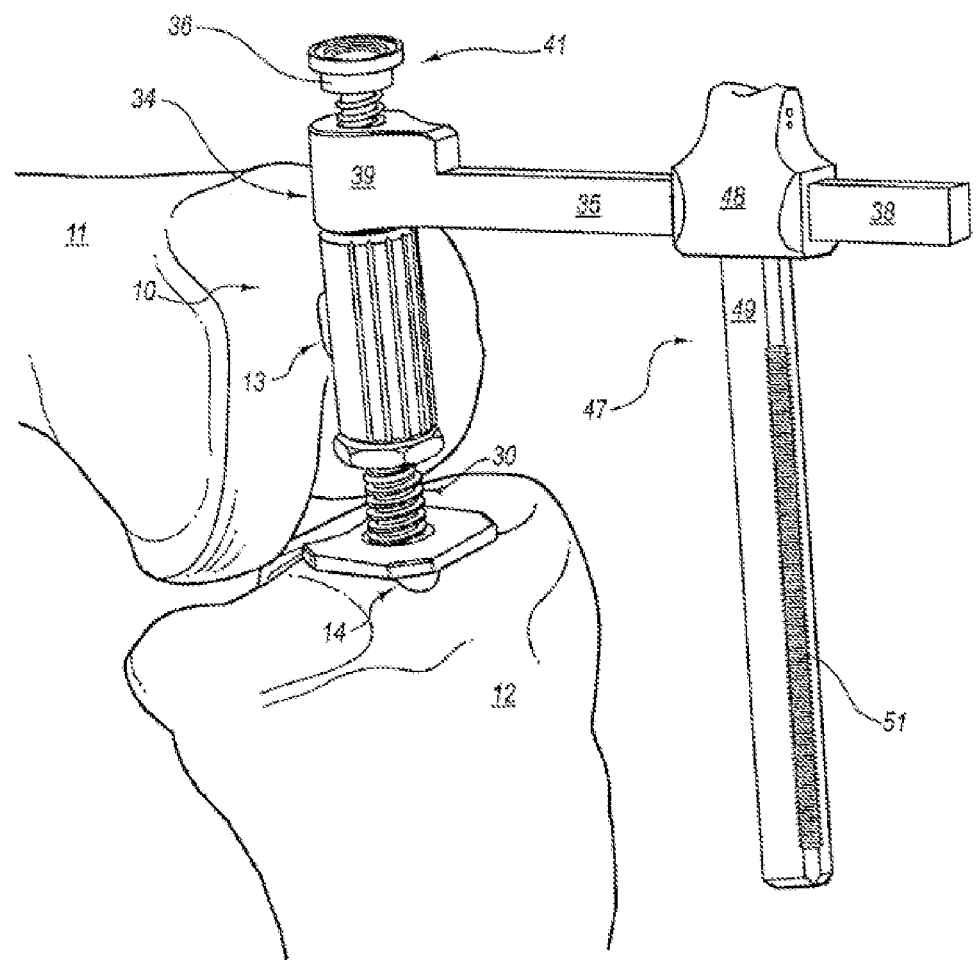
FIG. 12 is a perspective view of a flexion guide support member of the assembly of the present invention connected to the first locking mechanism of FIG. 11.

Also included in the assembly 10 of the illustrated embodiment of the invention is a flexion guide support member 47 which is supported by the locking mechanism 34. Included in the flexion guide support member is a slider member 48 and a ratchet bar 49. The slider member defines a rectangular opening 50 which is sized and shaped to allow the slider member to be supported by, and slide along, the rectangular cross-section of the arm 35 of the locking mechanism 34. This motion allows the ratchet bar 49, which is attached to the slider member 48, to move toward and away from the knee joint. The slider member 48 is preferably shaped to have finger grips (e.g., the tapered portion of the illustrated slider member) and may also include some type of a pin or locking assembly to resist, but not prohibit its sliding relative to the arm 35. The ratchet bar 49 itself is also rectangular shaped in cross-section and, when assembled, extends distally from the arm 35 of the locking mechanism 34, as shown in FIG. 12. The ratchet bar 49 also includes a pair of chamfered corners supporting a plurality of adjacent ratchet grooves 51 extending along the length of the ratchet bar.

Figure 13:
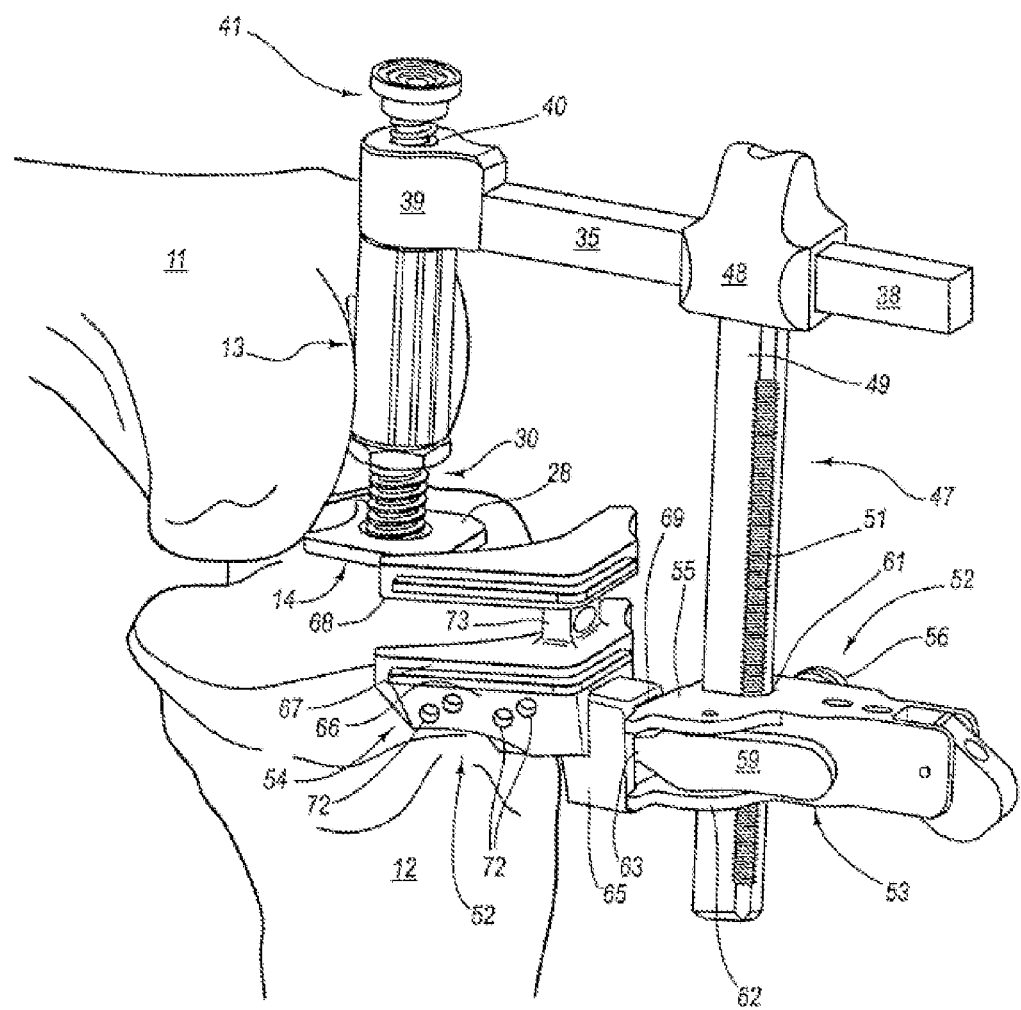
FIG. 13 is a perspective view of a flexed knee cutting guide assembly of the assembly of the present invention connected to the flexion guide support member of FIG. 12.
Figure 14:
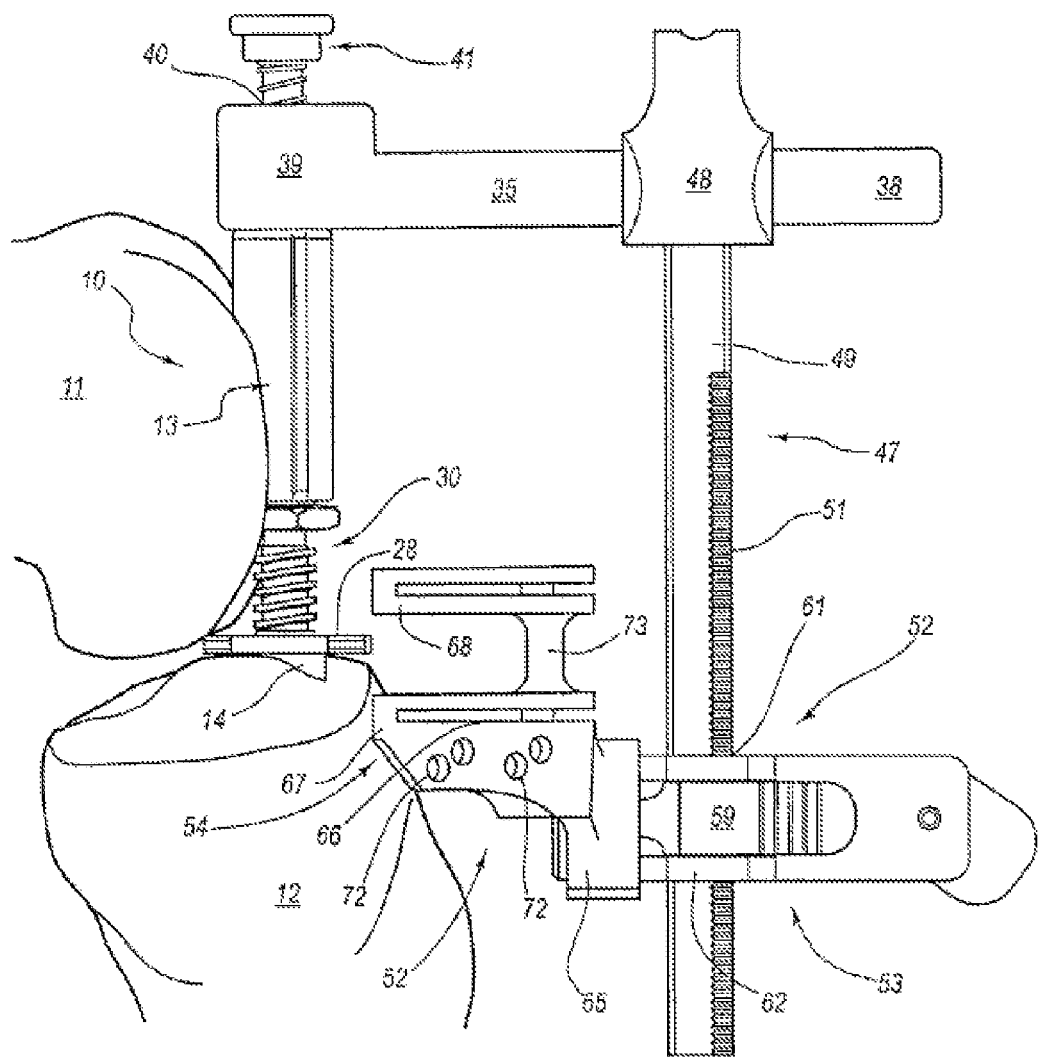
FIG. 14 is a side elevation view of the assembly of FIG. 13.
Figure 15:
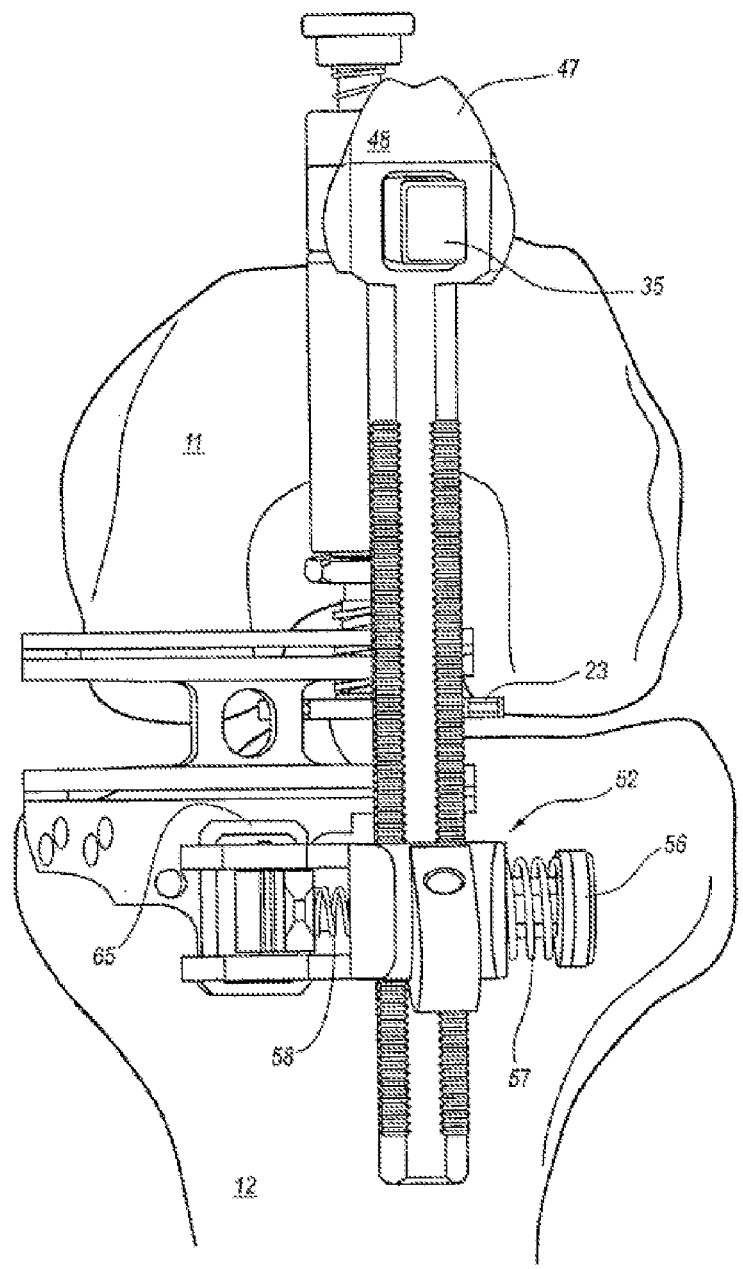
FIG. 15 is a rear elevation view of the assembly of FIG. 13.
Figure 16:
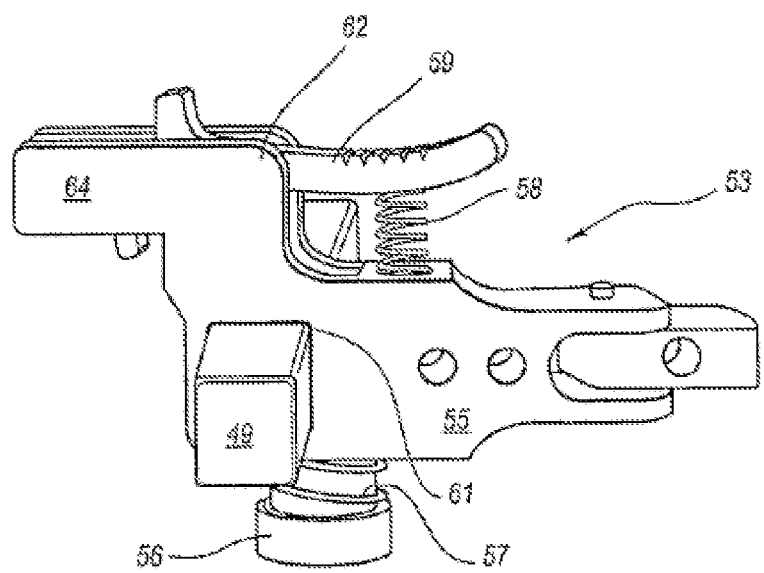
FIG. 16 is a bottom elevation view of a quick release mechanism of the flexed knee cutting guide assembly of FIG. 13.

The assembly 10 also includes a flexed knee cutting guide assembly 52 that attaches to the flexion guide support member 47, as shown in FIGS. 13, 14 and 15. The flexed knee cutting guide assembly 52 includes a quick release mechanism 53 and a cutting guide 54. The quick release mechanism 53 includes a body 55, a draw pin 56, first and second springs 57, 58, a locking lever 59 and a locking pin 60. As shown in FIG. 16, the body 55 defines a rectangular opening 61 which allows the body to be slid over the rectangular cross-section of the ratchet bar 49. In addition, the body 55 includes a side opening into which the draw pin 56 extends so that its end engages the ratchet grooves 51. In particular, the first spring 57 biases the draw pin into a position normally engaging the ratchet grooves so as to lock the draw pin, and hence the body 55, into a particular position on the slider member 48. The locking pin 60 extends through the body and through the draw pin 56 to secure the draw pin 56 and prevent it from disassembly.

Figure 17:
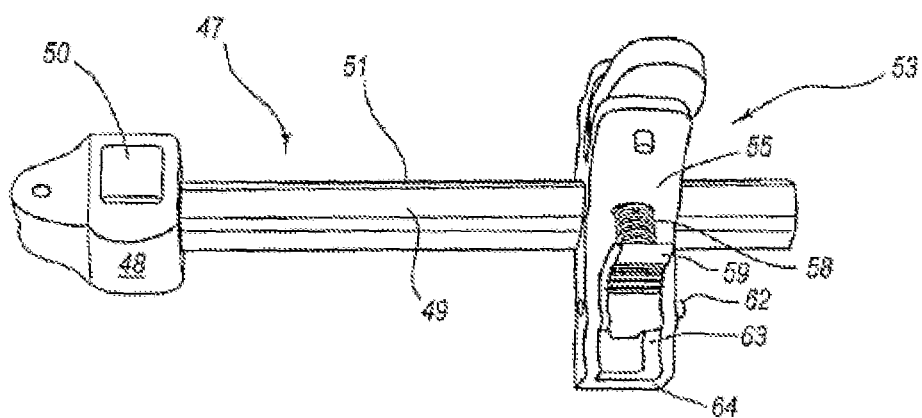
FIG. 17 is a perspective view of the quick release mechanism of FIG. 16 and the flexion guide support member of FIG. 12.

The body 55 additionally includes a clevis 62 that extends outwards from the opposite side of the body from the draw pin 56 and which supports rotation of the locking lever 59 about its middle portion. As well shown in FIG. 17, the locking lever has a curved finger grip biased outward from the body 55 by the second spring 58 and the opposite end of the locking lever includes a tapered tongue 63 which, as will be described below, engages the cutting guide 54 so as to lock the quick release mechanism 53 thereto. Extending away from the clevis 62, opposite the locking lever, is an engagement member 64 of the body 55. The engagement member 64 has a rectangular cross-section and, in the assembled condition shown in FIG. 13, extends into a connection with the cutting guide 54.

Figure 18:
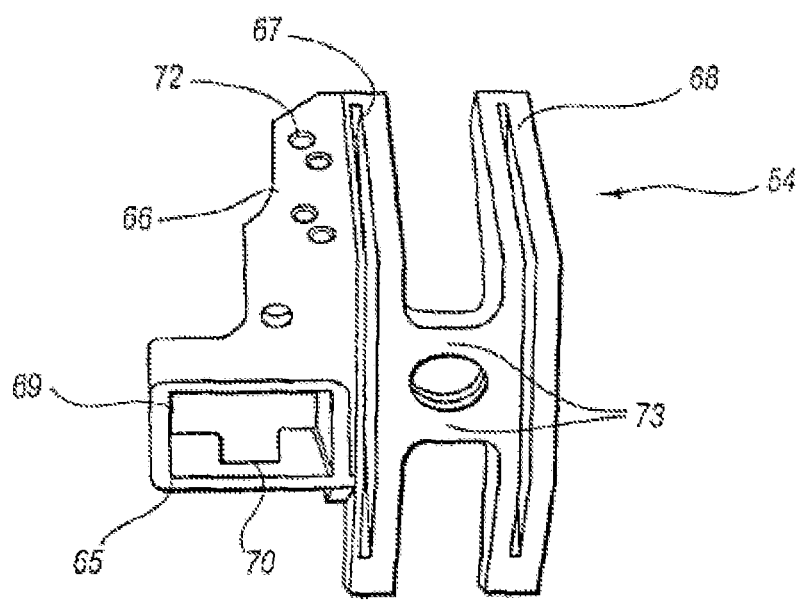
FIG. 18 is a perspective view of a flexed knee cutting guide of the flexed knee cutting guide assembly of FIG. 13.

As shown in FIG. 13, the cutting guide 54 extends posteriorly (when assembled) from the quick release mechanism 53 and includes a mounting portion 65, a k-wire guide or fixation pin portion 66, a crosspin portion 71, a proximal tibial cut guide portion 67 and a posterior condylar femoral cut guide portion 68. The mounting portion 65 defines a rectangular opening 69 that is sized and shaped to slidably receive the engagement member 64 of the body 55 of the quick release mechanism 53. The mounting portion 65 also defines a notch 70 in one of the sidewalls of the rectangular opening 69, as shown in FIG. 18. The notch 70 is sized, shaped and positioned to receive the tapered tongue 63 of the locking lever 59 when the locking lever is under the bias of the second spring 58, as shown in FIG. 15. Release of the cutting guide 54 is easily accomplished by depressing the free end of the locking lever 59, overcoming the bias of the second spring 58 and disengaging the tapered tongue from the notch 70 of the mounting portion 65.

The fixation pin (or k-wire) guide portion 66, the tibial cut guide portion 67 and the femoral cut guide portion 68 each have a crescent shape that extends in a medial-lateral direction around the anatomical curvature of the anterior-medial or anterior-lateral tibia (depending upon which cut is being made), as shown in FIG. 13. The fixation pin guide portion 66 is adjacent the mounting portion 65 and defines a plurality of fixation pin holes 72 that extend in a posterior direction at an angle so as to guide fixation pins (used to fix the cutting guide 54 before release of the other components of the assembly 10) into the thickest anterior portions of cortical bone on the tibia 12. Although less preferred, the number and orientation of the fixation pin holes could be varied depending upon the firmness of the connection desired, size and morphology of the tibia 12, etc.

Figure 19:
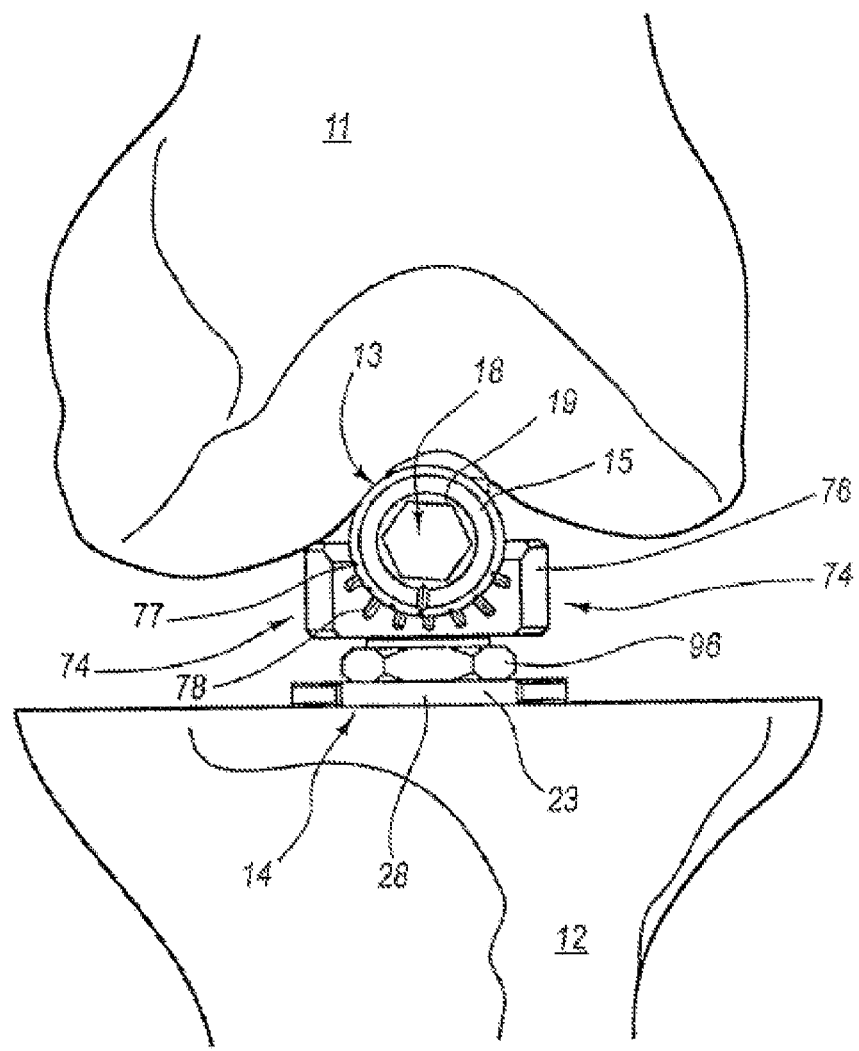
FIG. 19 is a front elevation view of a tibial angulation guide of the assembly of the present invention extending between the femoral and tibial IM rods of FIG. 1, coupled with an extension bolt.

The tibial cut guide portion 67 is positioned adjacent the fixation pin guide portion 66 and defines a slot for guiding the tibial cut. The slot extends along the length of the crescent shape of the guide portion 67 and generally has a parallel orientation with respect to the tibial plateau. However, the resection plane defined by guide portion 67 may vary in posterior slope (sagittal plane angularity) and varus/valgus (coronal plane angularity), depending on the desired position and preference of the surgeon for the cutting guide 54. An example of such a cut is illustrated in FIG. 19, wherein the tibia has a flat planar cut extending in the anterior-posterior and medial-lateral planes on the proximal end of the tibia 12. The femoral cut guide portion 68 is proximally spaced from the tibial cut guide portion 67 by a pair of connection flanges 73 so as to bridge the knee joint compartment. Similar to the tibial cut guide portion 67, the femoral cut guide portion 68 defines a slot that extends along the length of the crescent shape. However, because the knee is in flexion, the cut is guided through the posterior of the condyles of the femur 11.

An advantage of the components of the assembly 10 for positioning cuts with the knee in flexion, including the femoral mount 15, the tibial mount 23, the flexion bolt 30, the locking mechanism 34, the flexion guide support member 47 and the flexed knee cutting guide assembly 52, is their usability with relatively non-invasive, narrow cuts in the anterior soft tissues of the knee (and with a retracted patella). Generally, as can be seen in FIGS. 14 and 15, the assembled components for making the cuts in knee flexion are relatively narrow as they extend out of the joint space in a U-shape, while at the same time providing a firm connection for supporting the cutting guide 54, a quick assembly and release of the components and accurate positioning of the flexed knee cutting guide. Considering the cutting guide 54 by itself (which can be positioned inside of the capsular incision), the width of this component is small compared to conventional cutting guides, for example, within a range of up to 4 to 5 cm thereby allowing their use with minimally invasive approaches to the knee joint.

The assembly 10 also includes instrumentation configured to guide cuts with the knee in extension (i.e., with the tibia and femur generally aligned, or at 0° of flexion), as shown in FIGS. 19-29. For knee extension, both the femoral IM rod 13 and the tibial IM rod 14 remain in place, as shown in FIG. 19. However, instead of attachment of the tibial mount 23 to the tibial IM rod 14, a tibial angulation guide 74 is attached to the tibial IM rod. The tibial angulation guide 74 includes a gauge block 76 and a post 97 which fits into an extension bolt 96 (similar to the flexion bolt 30, but without the bushing 33). The extension bolt 96 also has a hex flange 75. Alternatively, a separate gauge block 76 may be employed with a shaft (as shown in FIG. 6) that extends into an opening in the bushing 33, allowing removal of the bolt 30 to be avoided.

Figure 20:
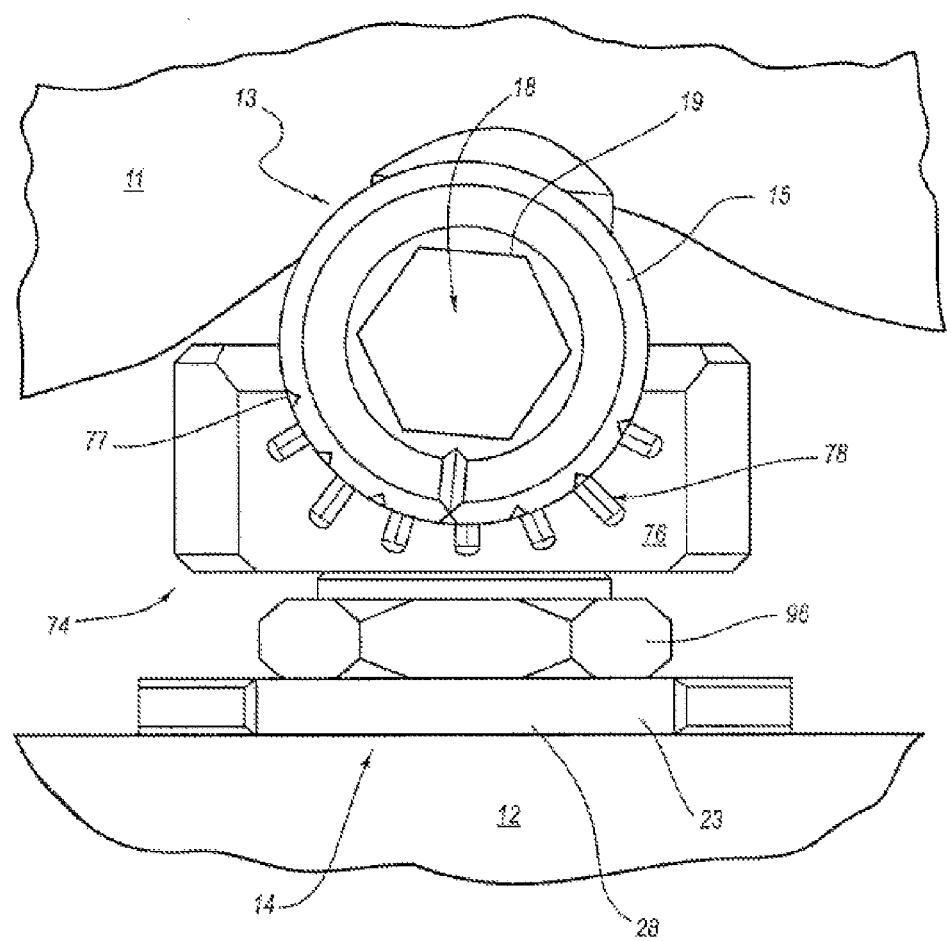
FIG. 20 is an enlarged view of the IM rods and tibial angulation guide of FIG. 19.
Figure 21:
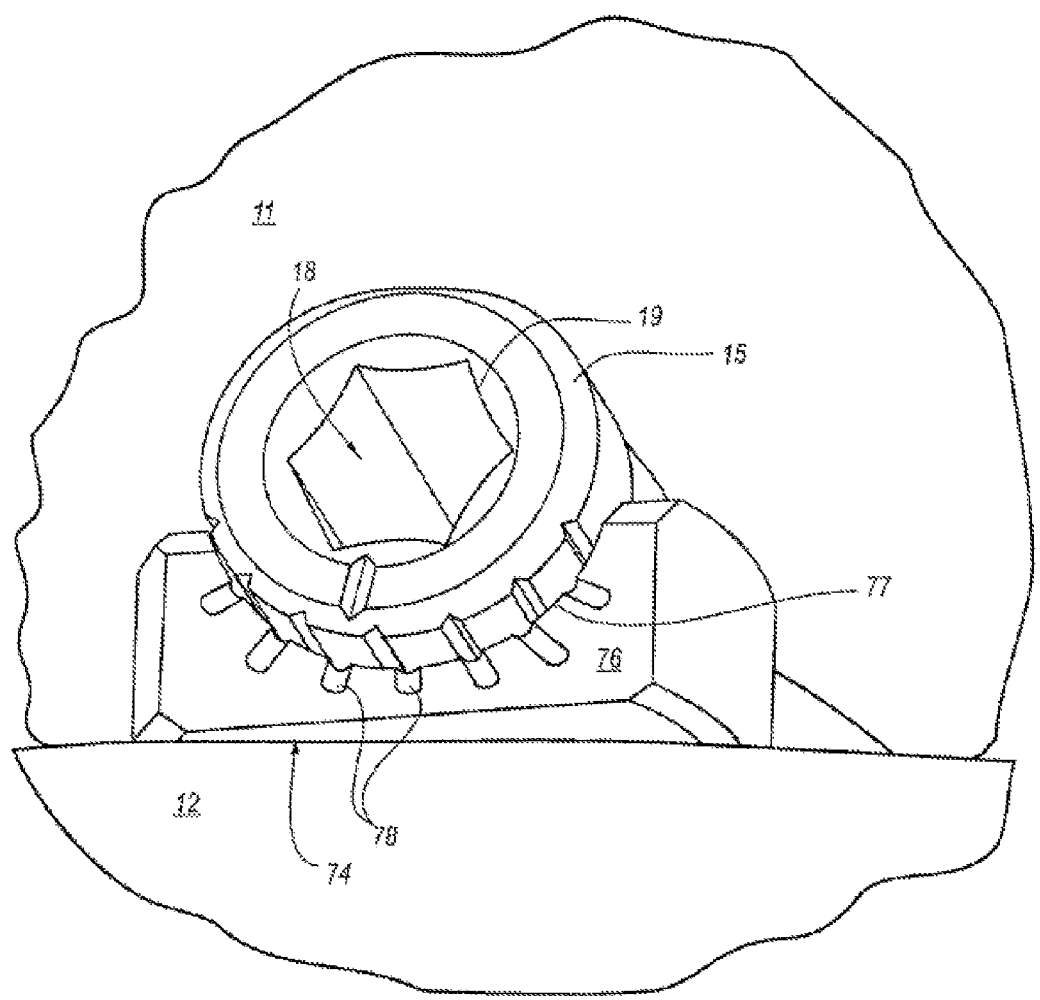
FIG. 21 is another enlarged view of the IM rods and tibial angulation guide of FIG. 19.

Regardless, gauge block 76 extends upward from the plateau flange 28 of the tibial mount 23 when the threaded shaft of the extension bolt 96 extends into the threaded opening 29 and defines an arc surface 77 and a plurality of gauge marks 78 defined on its anterior surface, as shown in FIGS. 19-21. The arc surface 77 is shaped and sized to receive the outer surface of the cylindrically shaped femoral mount 15 and allow the femoral mount 15 to rotate in the varus-valgus direction and slide in the anterior-posterior direction therein. These motions are left free so as to not over-constrain the femur 11 and tibia 12, but still promote anterior-posterior alignment of the instruments and rotational position selection, for better positioning of the tibial and femoral cuts. Other variations and combinations of shapes of the femoral mount 15 and tibial angulation guide 74 could be employed to allow these ranges of motion, such as by reversing the shapes of the gauge block 76 (it having a cylindrical shape) and the femoral mount 15 (it having the arc shape), by having a rounded shape between two plates, extending the angulation readings away from the instrument assembly, etc., and still be within the purview of the present invention.

Adjustment of the relative proximal-distal positioning of the femur 11 and the tibia 12 is accomplished, similar to the technique in the flexion position, by adjusting the rotation of the hex flange 75 of the extension bolt 96 with a torque wrench. This motion advances or retracts the threaded shaft of the tibial extension bolt 96 into and out of the threaded opening 29 in the tibial mount 23 and advances the tibial angulation guide 74 toward the femoral mount 15. Preferably, the femur 11 and tibia 12 are distracted until the torque wrench has a reading similar to that for the knee in flexion to ensure that the joint is not overly tight in knee extension. With respect to the torque wrench and the amount of joint space, the torque wrench may be equipped with an extender that extends the length of the wrench, has hex-shaped jaws at its end and is relatively thin or low profile. If this is the case, the torque measurements may be adjusted to compensate for the additional length of the extender. In either case, the objective is to match the torque value obtained when the instrument construct constrained the knee in some degree of flexion, in this instance 90° of flexion or increments therebetween, and torque the bolt to a similar torque measurement that was reached on the torque wrench in the previous step, or until adequate tension of the ligamentous structure is obtained.

Referring again to FIGS. 20 and 21, the gauge marks 78 of the gauge block 76 radiate outward from the center of rotation of the femoral mount 15, starting at the outer surface of the femoral mount, and are positioned on the anterior surface of the gauge block. The gauge marks 78 of the gauge block 76 are configured to match up with gauge marks 21 of the femoral mount 15 (as shown by the arrow) to indicate a valgus angle of the tibia 12 with respect to the femur 11. Generally, the valgus angle should be within a range of 3 to 7 degrees, or even 2 to 9 degrees, depending upon the knee's morphology, surgeon preference, etc.

Figure 22:
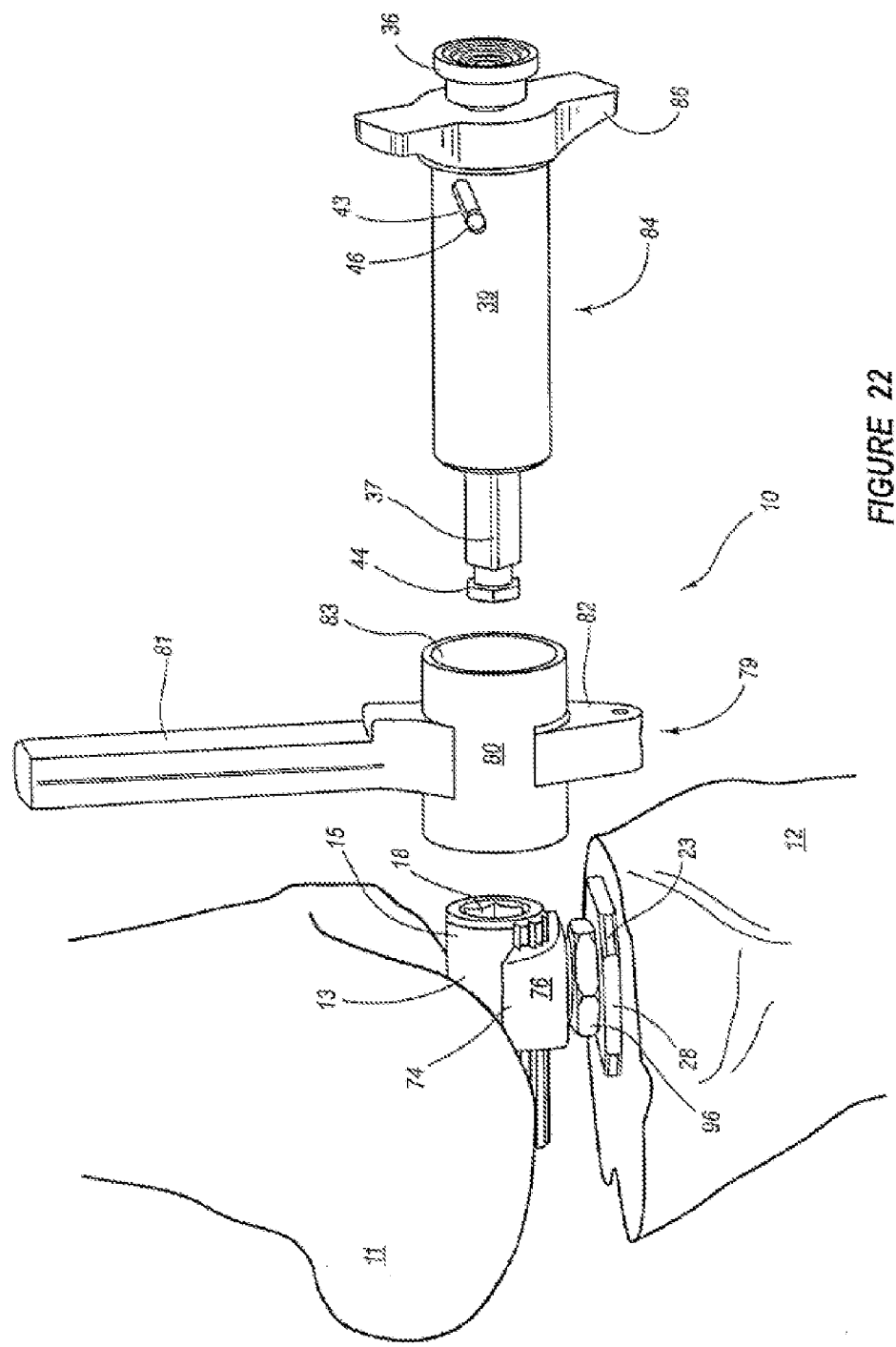
FIG. 22 is a perspective view of a second locking mechanism and extension guide support member of the assembly of the present invention being assembled to the femoral IM rod of FIG. 1.
Figure 23:
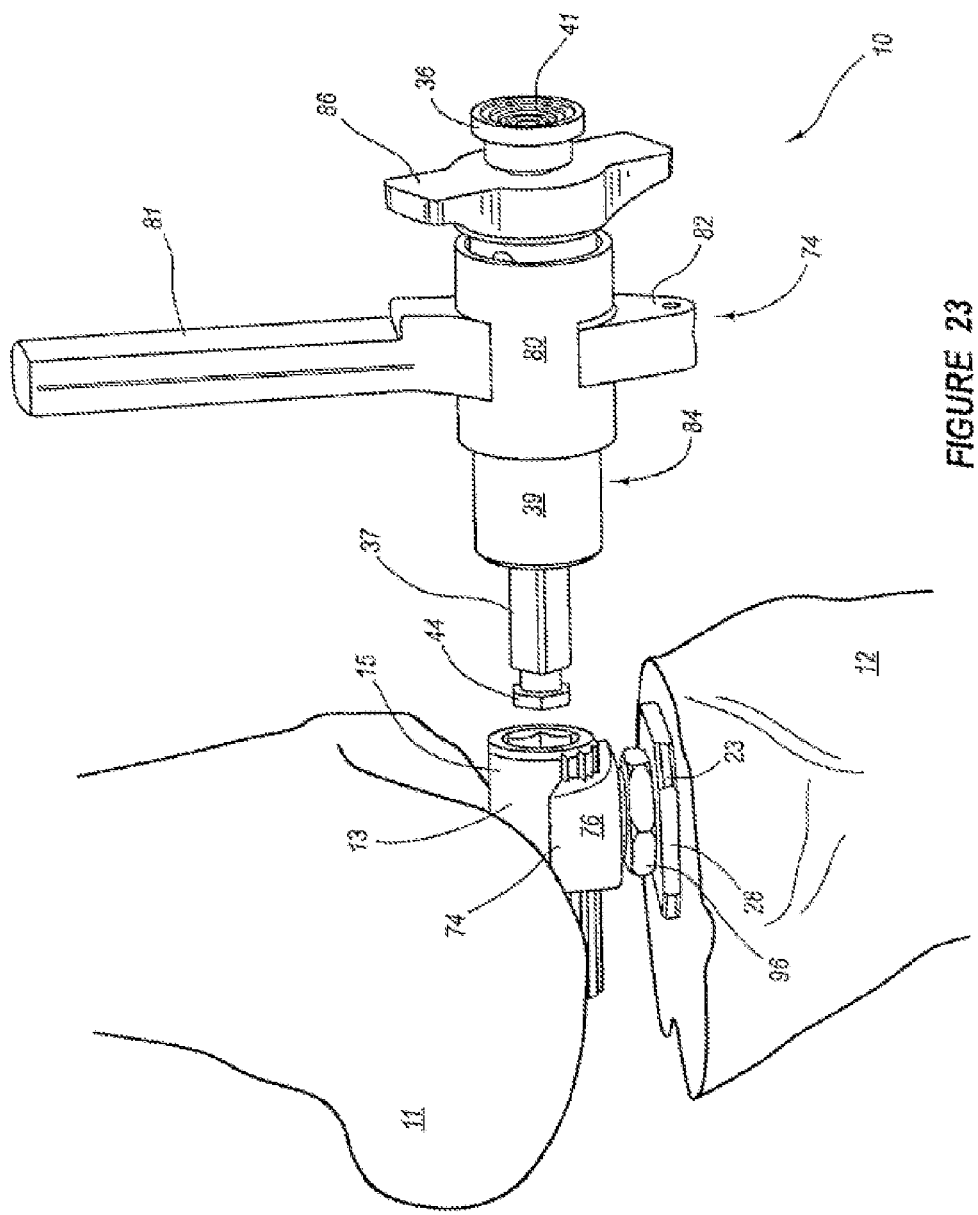
FIG. 23 is an enlarged perspective view of the assembly of the extension guide support member of the present invention to the second locking mechanism of FIG. 22.

Once the angulation and proximal-distal positioning of the tibia 12 with respect to the femur 11 has been adjusted, an extension guide support member 79 is attached to the femoral mount 15 using a second locking mechanism 84, as shown in FIGS. 22 and 23. Generally, the second locking mechanism 84 includes the plunger 36 (and its components including hexagonal end 44), hex extension 37 and helical slot 43 which are similarly numbered as they share a similar function with the same components of the first locking mechanism 34. The second locking mechanism 84 differs in that the head portion 39 is somewhat longer, is cylindrical and lacks the elongate portion 38 of the arm 35. Also, the second locking mechanism 84 includes a grip flange 86 positioned adjacent the plunger 36 to facilitate a finger grip when depressing the plunger. Regardless, the hexagonal end 44 has the same rotating motion that facilitates quick attachment of the end of the second locking mechanism 84 to the femoral mount 15.

The extension guide support member 79 includes a mounting portion 80, a support arm 81 and a fixation flange 82. The mounting portion 80 has a cylindrical shape with a cylindrical opening 83 extending therethrough that is configured to slidably receive the second locking mechanism 84, but is not rotationally constrained by said second locking mechanism 84. Extending away from one side of the mounting portion 80 is the support arm 81 which is an elongate structure with a T-shaped cross section. Extending away from the other side of the mounting portion 80 is an additional flange 82 that acts as a housing for a mechanism, in this case a ball and spring 85, to provide some resistance to rotation of the extension guide support member 79 with respect to the second locking mechanism 84.

Also included in the illustrated embodiment of the assembly 10, is an extended knee cutting guide 87 that is supported by the extension guide support member 79 during positioning, as shown in FIGS. 24-29. The extended knee cutting guide 87 includes a mounting portion 88, a fixation pin (or k-wire) guide portion 89, a femoral cut guide portion 90 and a reference lever 91. The mounting portion 88 is generally centered in a body portion of the extended knee cutting guide 87 and defines a channel 92 that has a cross-sectional shape matched to the T-shaped cross-section of the support arm 81. The matching shapes allow the extended knee cutting guide 87 to slide in the proximal-distal direction along the support arm 81.

Figure 25:
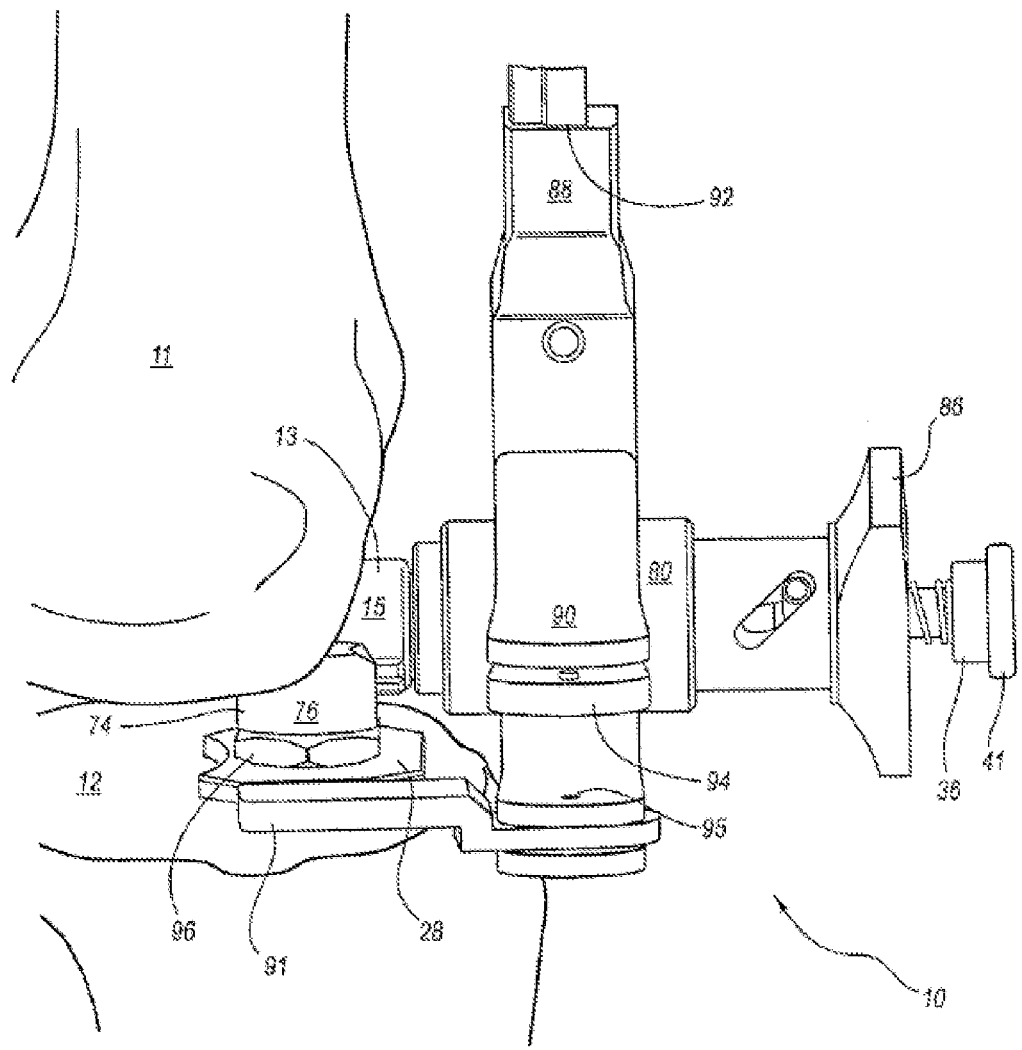
Figure 26:
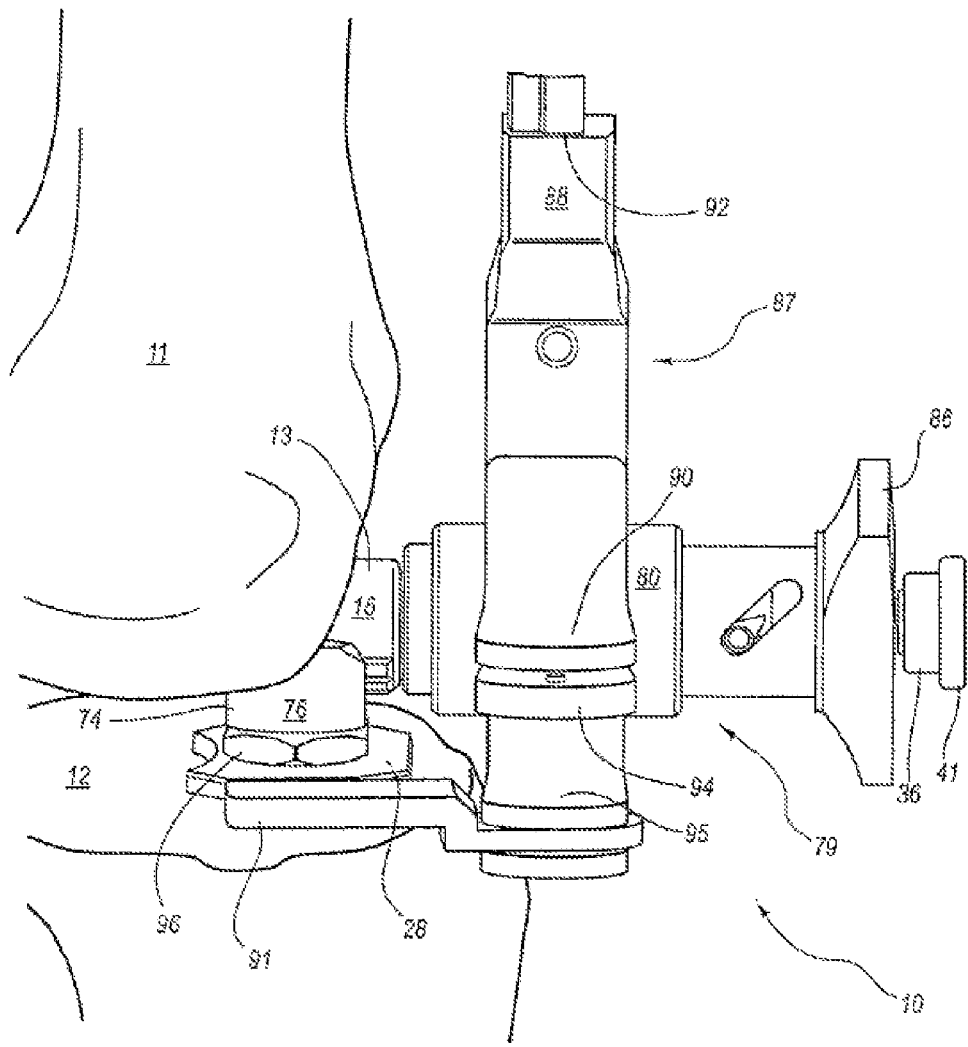

The fixation pin guide portion 89 defines a plurality of k-wire (or other type of fastener, e.g., screws, nails, etc.) holes 93 that allow fixation using fixation pins after positioning of the extended knee cutting guide 87. The holes 93 are positioned on medial and lateral sides of the anterior femur when positioned so as to allow fixation to relatively thick cortical bone, as shown in FIG. 25. As with the k-wire holes 72, the k-wire holes 93 can be oriented at various angles or selectively positioned to guide fasteners into and through larger lengths of denser bone on the femur 11.

The femoral cut guide portion 90 extends either laterally or medially for a unicompartmental reconstruction (as with the illustrated embodiment), or in both directions for a full resection of the femoral condyles. Notably, the guide portion 90 extends distally in the shape of a U that fits around the second locking mechanism 84 when the extended knee cutting guide 87 is in place, as well shown in FIG. 29. Regardless, the guide portion 90 extends distally from the k-wire guide portion 89 and then laterally or medially to define a guide slot 94. The guide slot 94 is of sufficient width to allow passage of cutting instruments or blades but still promote a relatively straight or planar resection. Notably, extension medially allows the laterally shifted patella to be avoided in a medially oriented approach to the knee joint compartment.

Figure 24:
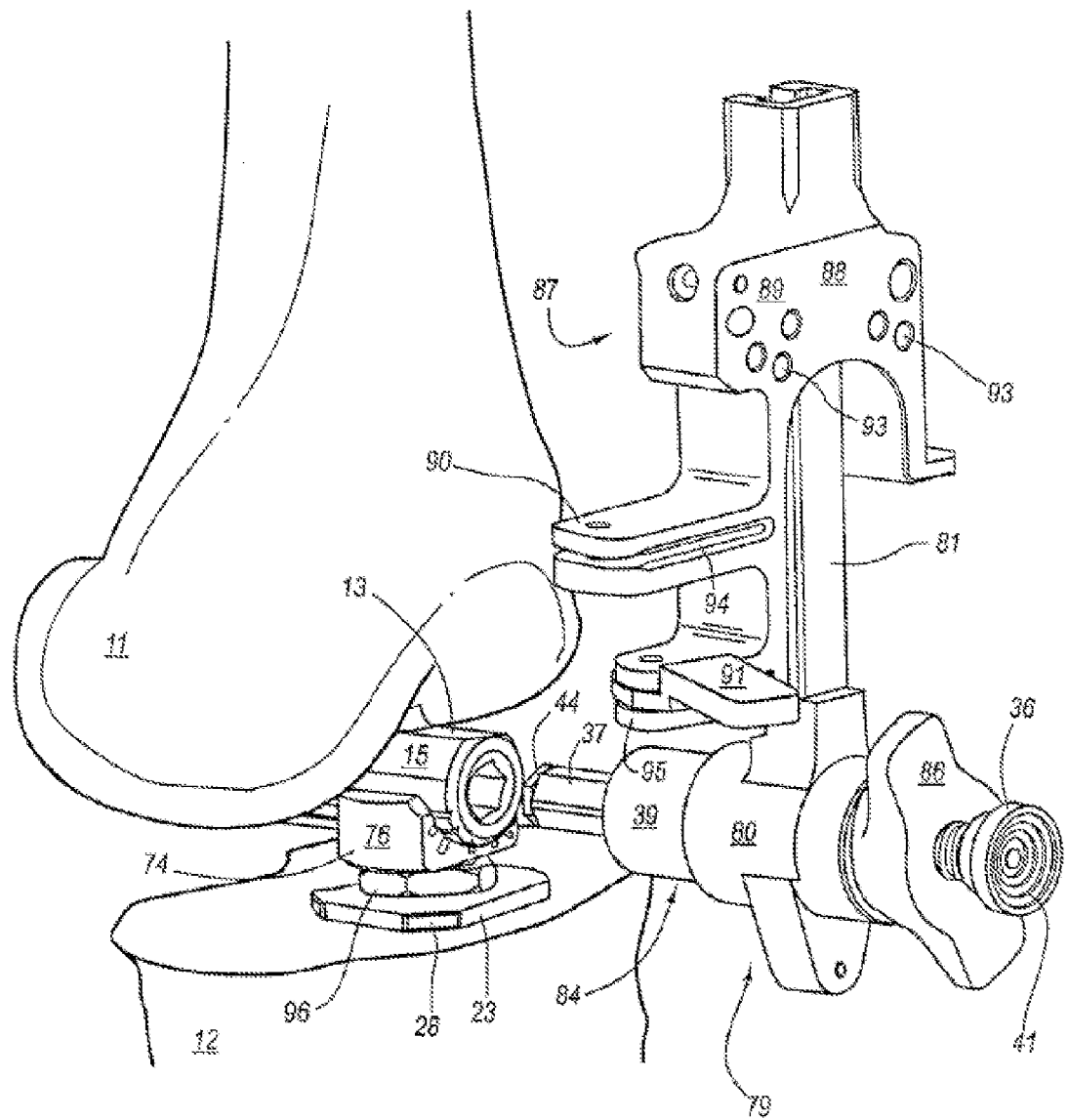
FIG. 24-26 are various a perspective views of an extended knee cutting guide of the assembly of the present invention attached to the extension guide support member and second locking mechanism of FIG. 22, and the femoral IM rod of FIG. 1.
Figure 27:
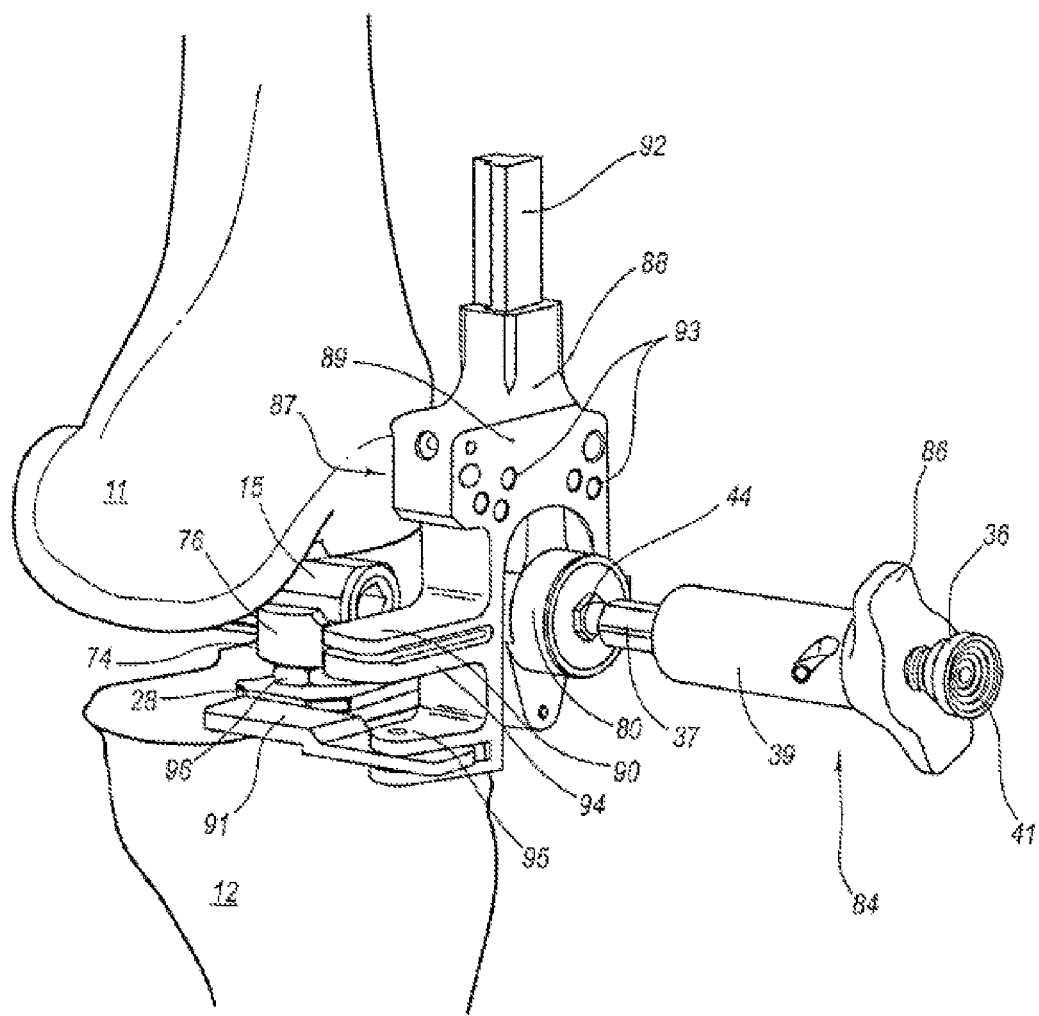
FIG. 27 is a perspective view illustrating disassembly of the second locking mechanism of FIG. 22, from the femoral IM rod of FIG. 1, once the extended knee cutting guide is fixed in position to the distal femur.
Figure 28:
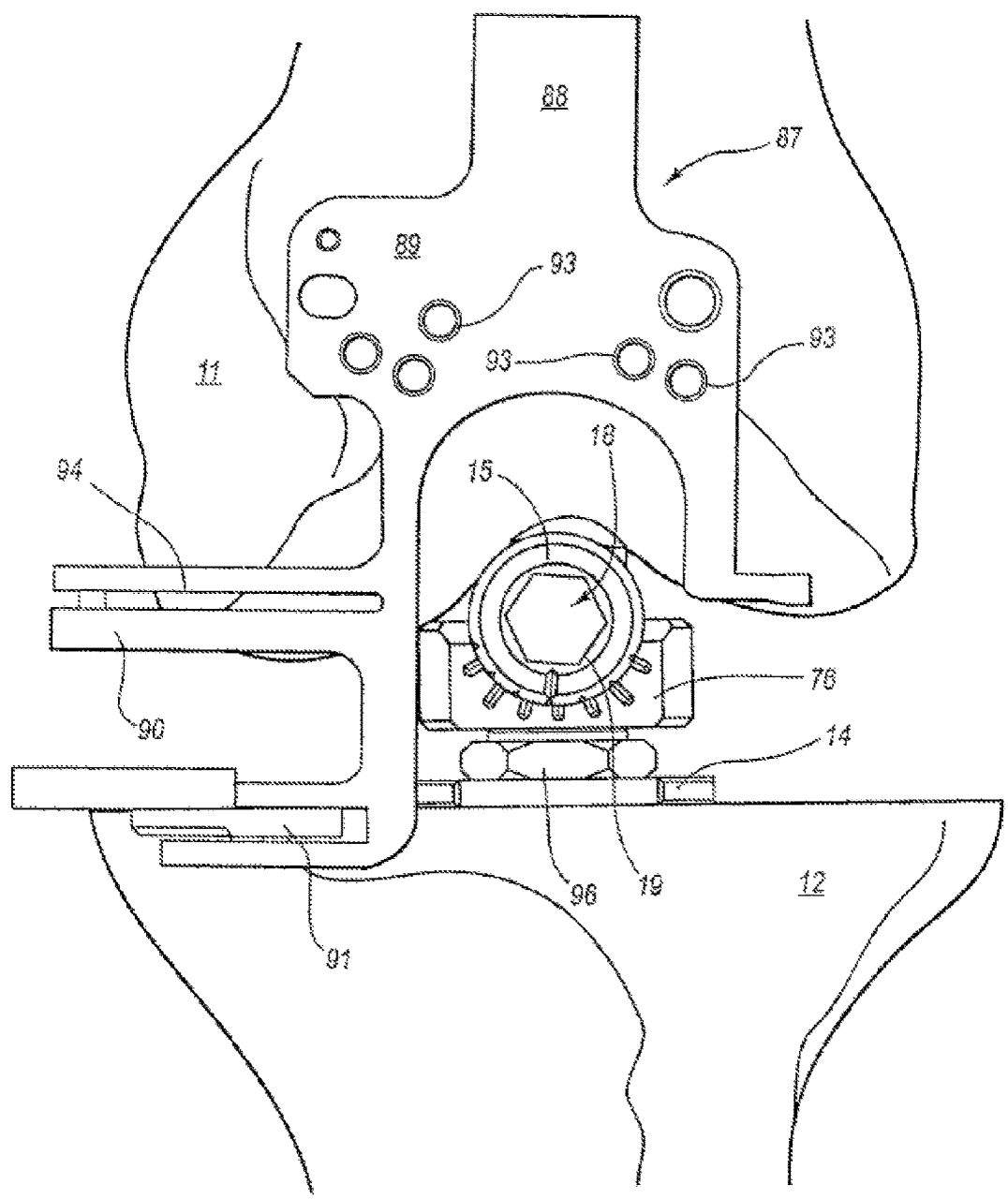
FIG. 28 is a front elevation view of the extended knee cutting guide of FIG. 24.
Figure 29:
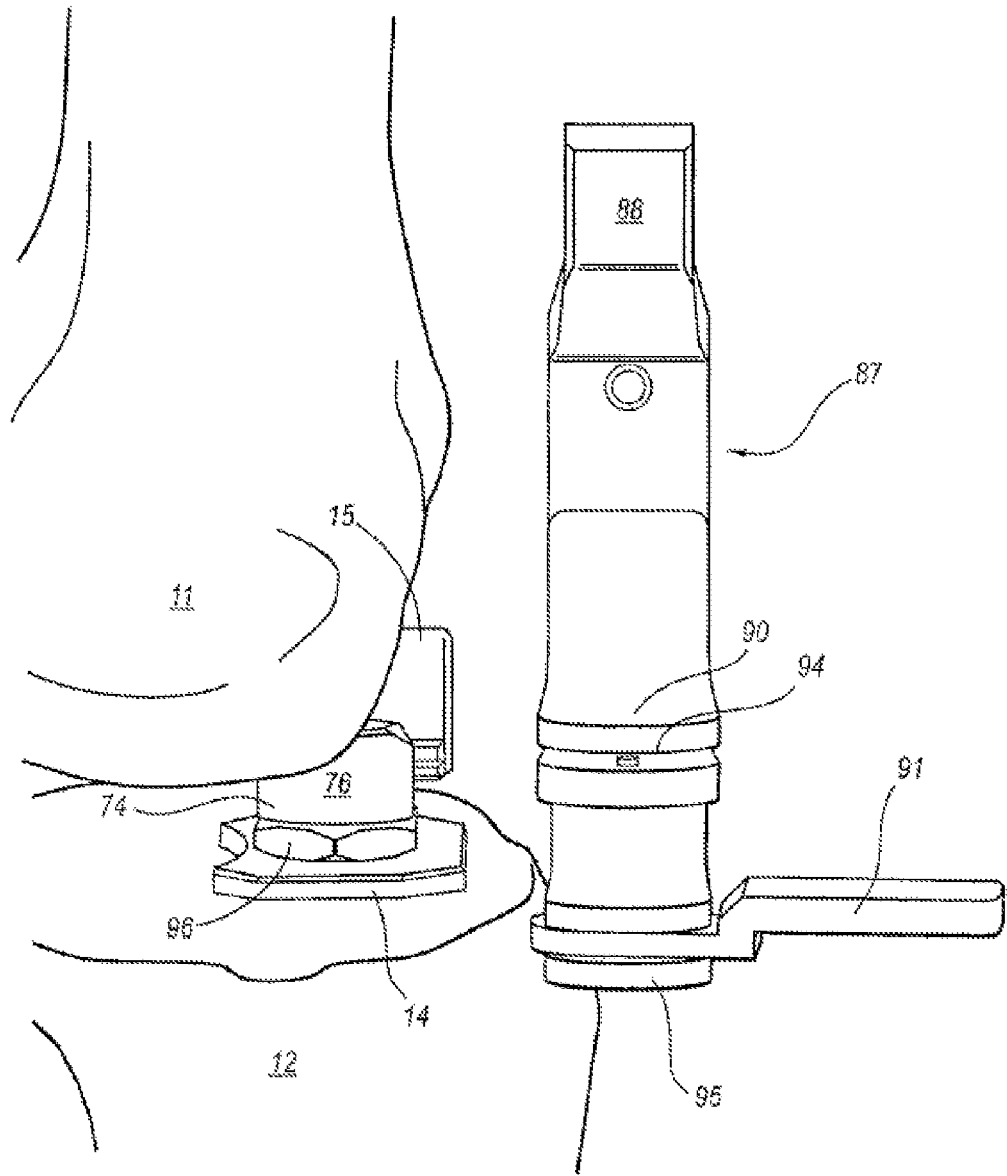
FIG. 29 is a side elevation view of the extended knee cutting guide of FIG. 24.

Extending further distally from the femoral cut guide portion 90 is a portion of the extended knee cutting guide 87 that defines a clevis 95 that rotationally supports the reference lever 91. The reference lever 91 extends laterally or medially and rotates in an anterior-posterior direction to allow positioning in the joint compartment, as shown in FIGS. 24 and 25. The reference lever 91 has a broad, flat distal surface that is configured to rest against the flat tibial cut and a flat lateral surface is configured to abut the side surface of the plateau flange 28. These surfaces provide a stop for the distal movement of the extended knee cutting guide 87 along the support arm 81 of the extension guide support member 79. With the reference lever 91 and the second locking mechanism 84 in place, fixation pins can be inserted through the pin holes 93 in the guide portion 89 to fix the femoral cut guide portion 90 to the femur 11. This allows removal of the extension guide support member 79, as shown in FIGS. 27, 28 and 29.

Advantageously, the components for positioning the cuts with the knee in extension, including the extension bolt 96, tibial angulation guide 74, the extension guide support member 79 and the extended knee cutting guide 87 are configured for passage through an anterior and medial approach to the knee compartment due to the narrow width and profile of the components. For example, as shown in FIG. 25, the posterior portion of the second locking mechanism 84 and the reference lever 91 would pass through the incision and exhibit the aforementioned narrowness and low-profile. Preferably, the width of this component is small compared to conventional cutting guides, for example, within a range of up to 4 to 5 cm thereby allowing their use with minimally invasive approaches to the knee joint.

Figure 30:
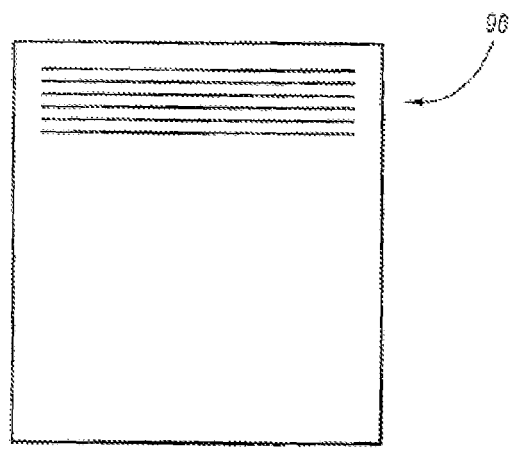
FIG. 30 is a plan view of an L-shaped cutting block of the assembly the present invention.
Figure 31:
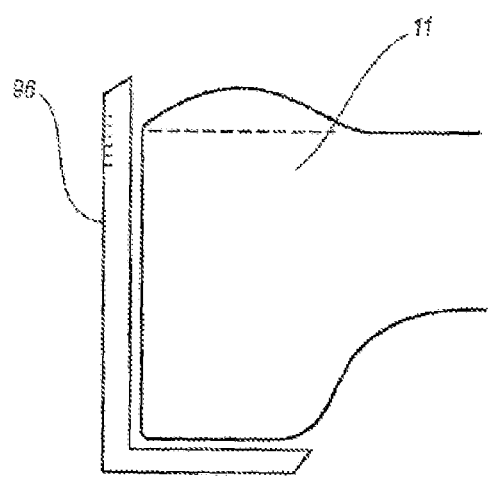
FIG. 31 is a side elevation view of the L-shaped cutting block of FIG. 30 being used to cut an anterior condyle of a femur.

After these initial cuts, further cuts can then be made using the initial cuts as a reference. As shown in FIGS. 30 and 31, an L-plate 99 is employed to abut the posterior and distal flat surface of the femur 11 to guide an anterior cut. Chamfer cuts (anterior and posterior) can be made using a chamfer cut block and other finishing cuts can be references from the initial cuts made using the assembly 10 of the present invention. Additional description of these finishing cuts can be found in U.S. patent application Ser. No. 10/794,188 filed on Mar. 5, 2004, entitled "Reference Mark Adjustment Mechanism for a Femoral Caliper and Method of Using the Same," which is hereby incorporated herein by reference.

Figure 32:
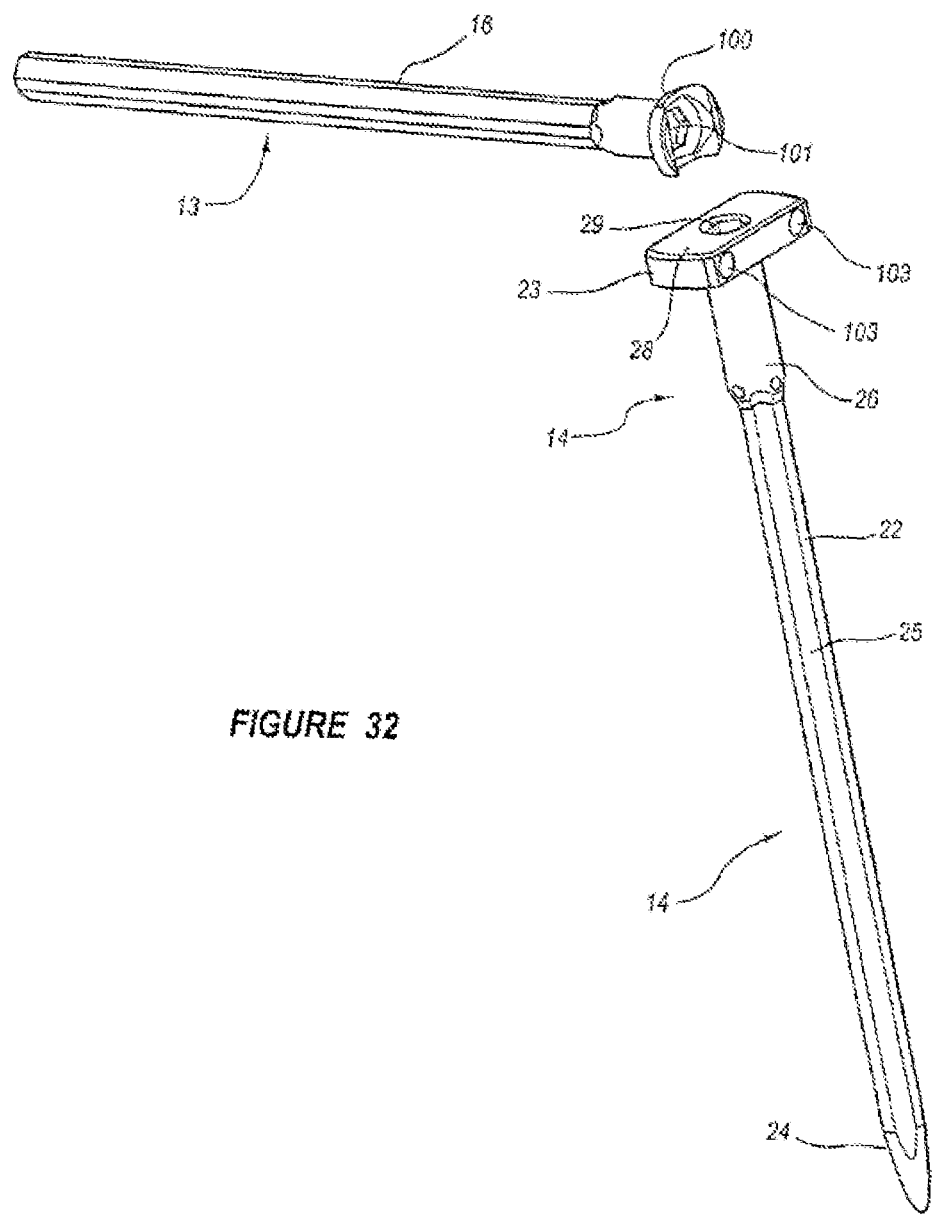
FIGS. 32-40 show various modular options of the present invention that promote quick assembly and facilitate minimally invasive intra-operative use.
Figure 33:
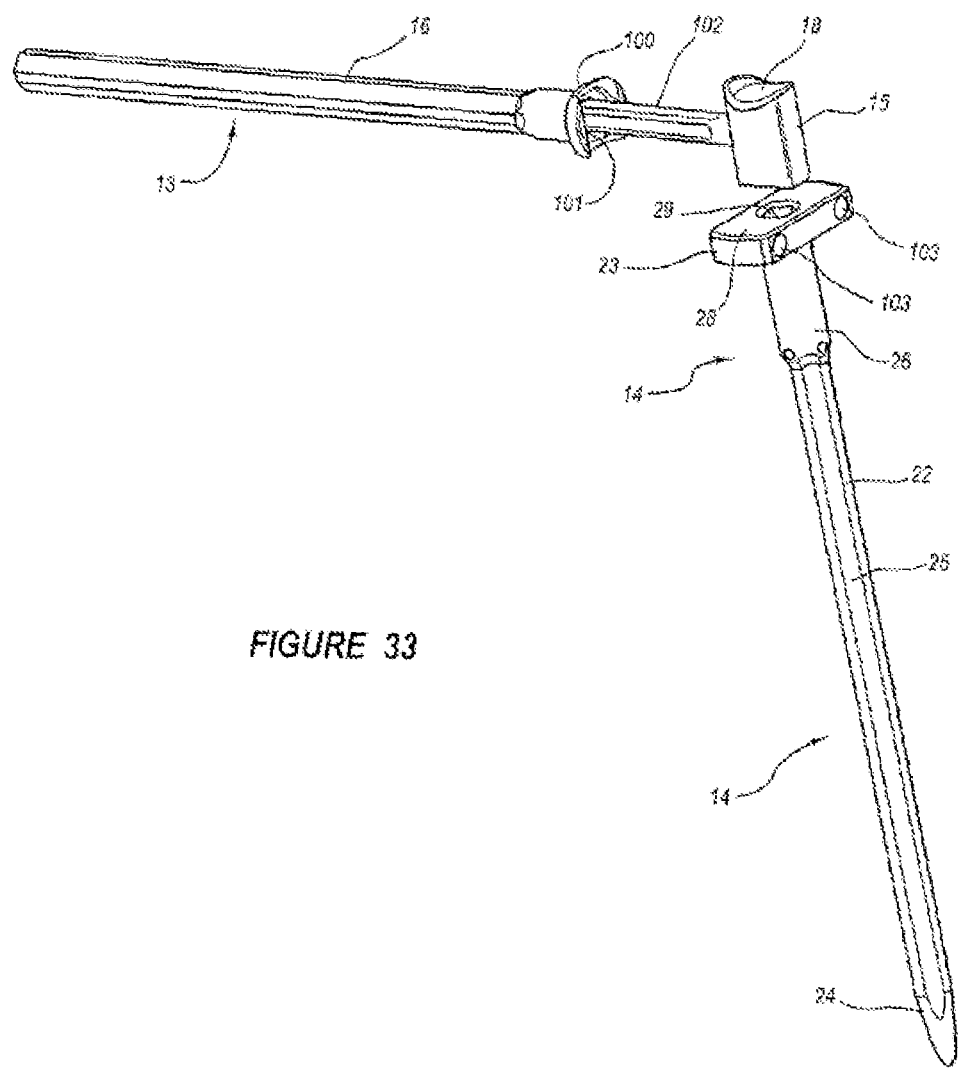

In another embodiment of the present invention, as shown by FIGS. 32 through 40, the assembly 10 includes additional modular options to promote quick assembly. As shown in FIG. 32, the femoral IM rod 13 includes a secondary femoral mount 100. The secondary femoral mount 100 has a saddle or crescent shape that extends laterally and distally from a central attachment to the distal end of the main shaft 16 of the femoral IM rod 13. Defined in the inner, convexly curved surface of the saddle is an opening 101 that is configured to receive a femoral mount rod 102 that supports the femoral mount 15, as shown in FIG. 33.

Figure 34:
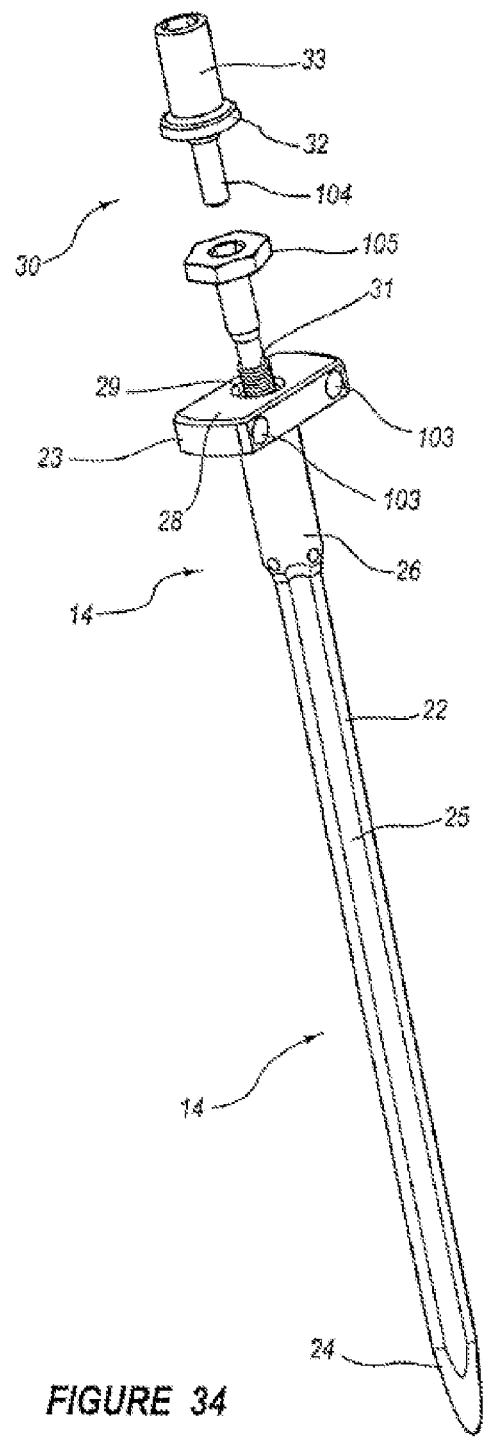
Figure 35:
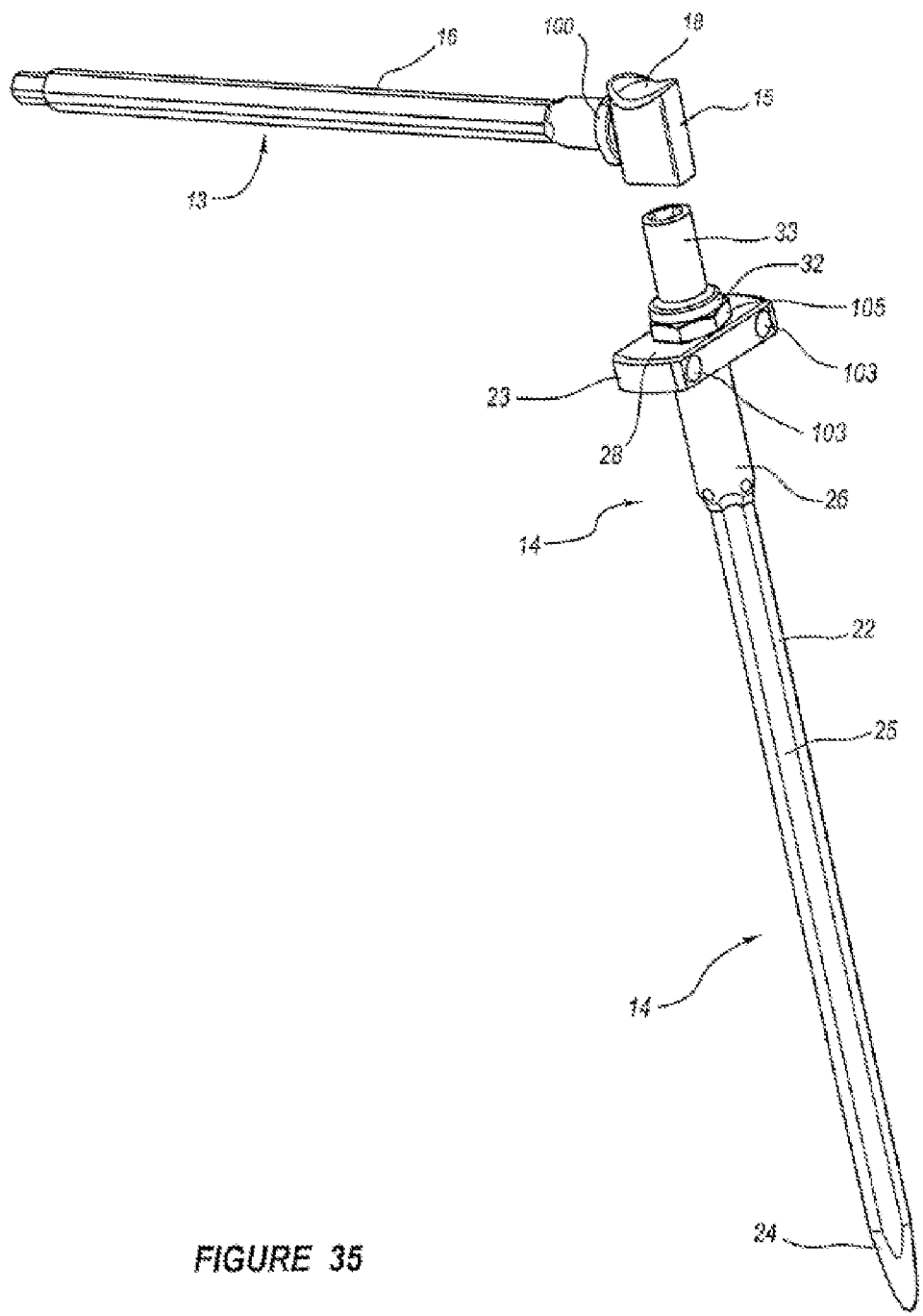
Figure 36:
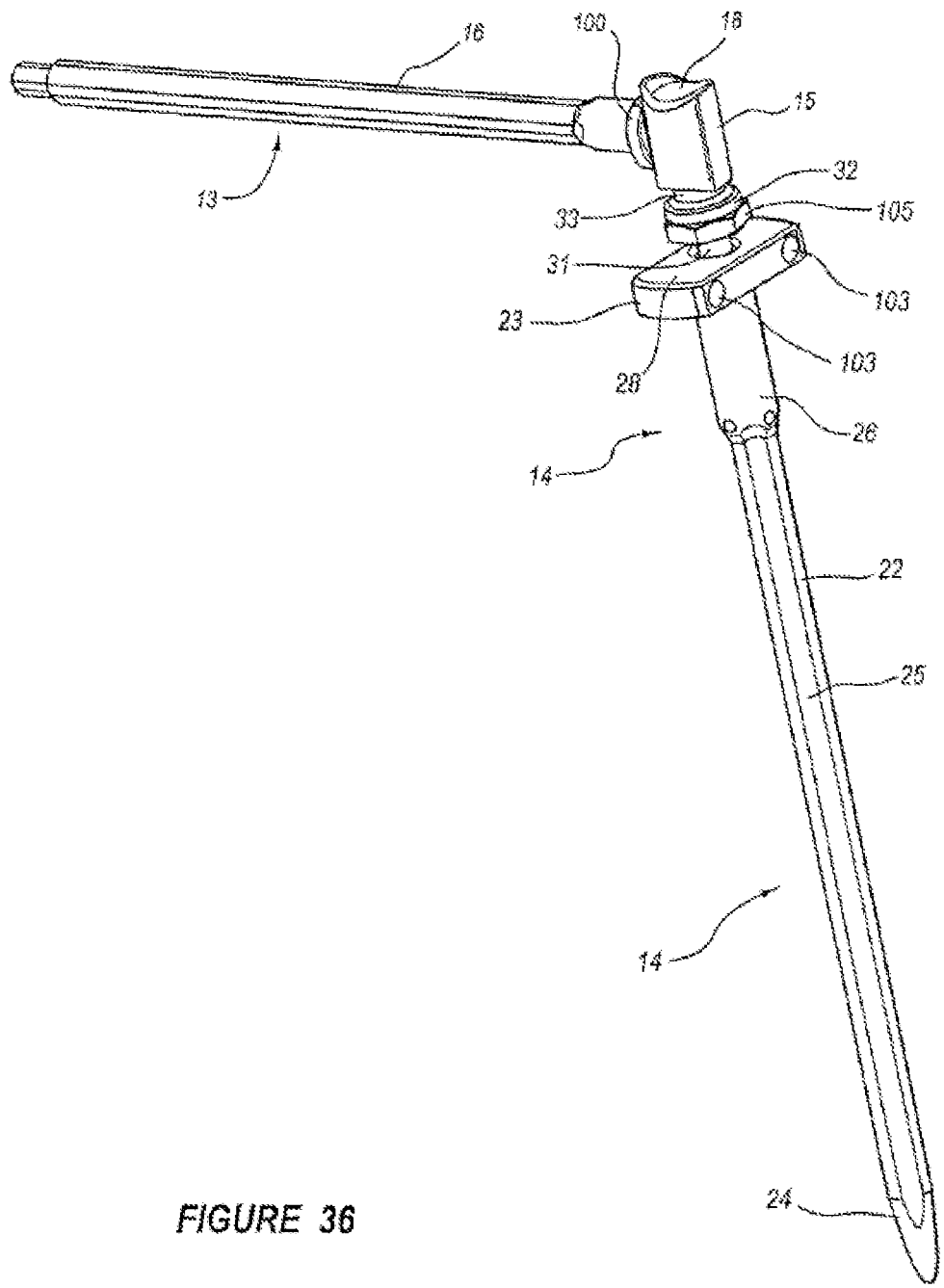

Referring again to FIG. 32, the tibial IM rod 14 includes a modified version of tibial mount 23 supported by the shaft 22. In particular, the plateau flange 28 of the tibial mount 23 has a widened rectangular shape that extends laterally outward from the threaded opening 29. Defined at the anterior side of the plateau flange 28 are a pair of guide mount openings 103 that extend posteriorly into the plateau flange. As shown in FIG. 34, the flexion bolt 30 may also be further modularized by providing a post 104 for mounting the bushing 33 and hex flange 32 within a central opening defined in a hex-head bolt 105 that includes the threaded shaft 31 extending from its head 105. FIGS. 35 and 36 show the assembly of the femoral mount 15 and tibial mount 32, along with tightening adjustment by elevation of the hex head bolt 105.

Figure 37:
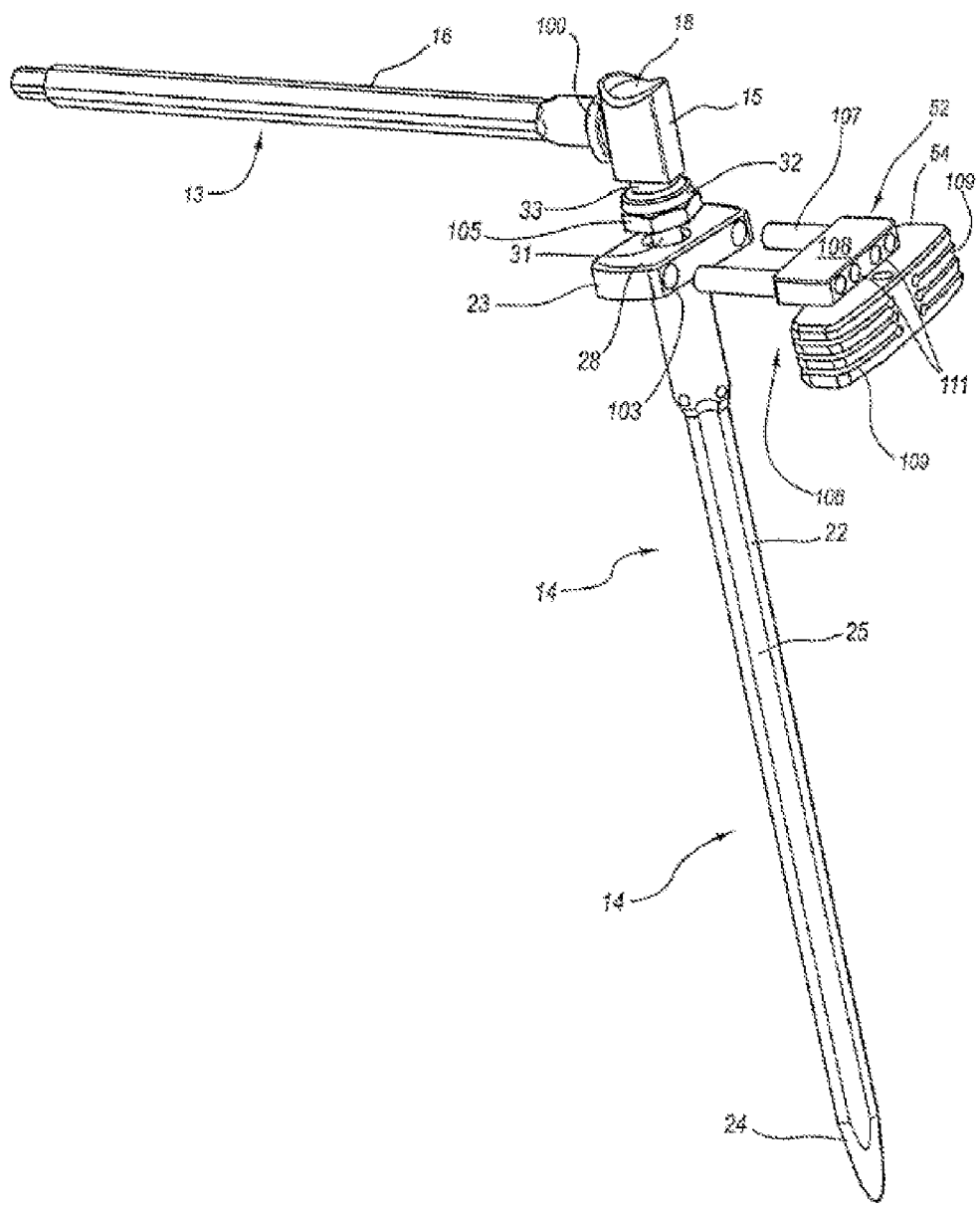

As shown in FIG. 37, the assembly 10 also includes a flexed knee cutting guide assembly 52 that includes a flexed knee cutting guide 54 and a direct mount 106. The direct mount includes a pair of posts 107 that are spaced apart and extend from a mounting block 108. The spacing and size of the posts 107 are configured to extend into the guide mount openings 103 defined in the plateau flange 28. Mounting block 108 can be coupled to tibial mount 32, such as by hermetically sealed magnets 111. The flexed knee cutting guide 54 is attached to and extends distally from the mounting block 108. The flexed knee cutting guide defines a selection of slots 109 for guiding tibial and femoral cuts.

The posterior femoral cut can be accomplished by turning the flexed knee cutting guide assembly 52 upside down or by using another block which would be a modification of the upside down cutting guide assembly 52 where the cutting guide 54 and selection of slots 109 is moved toward the posts 107 and therefore, closer to the posterior femoral condyles of the knee. The selection of slots 109 of cutting guide assembly 52 can be as shown with the slots attached centrally or could be open centrally and attached along both sides of the cutting guide 54.

Figure 38:
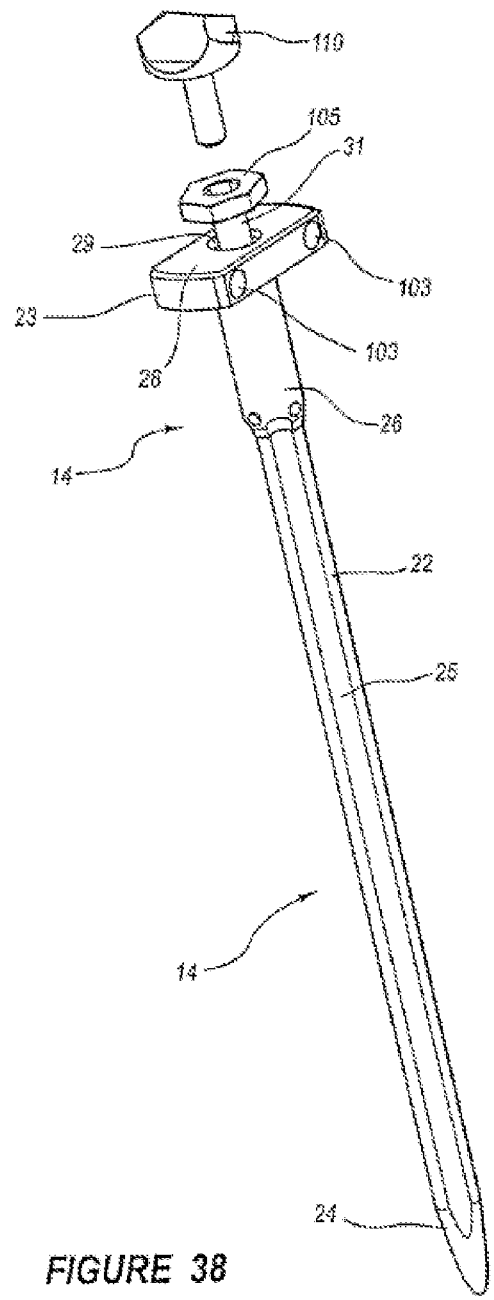
Figure 39:
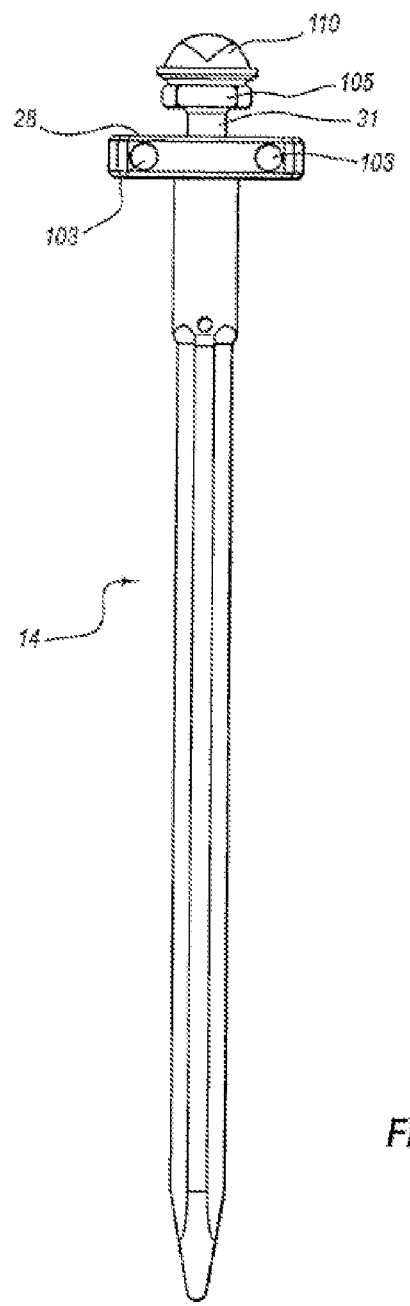
Figure 40:
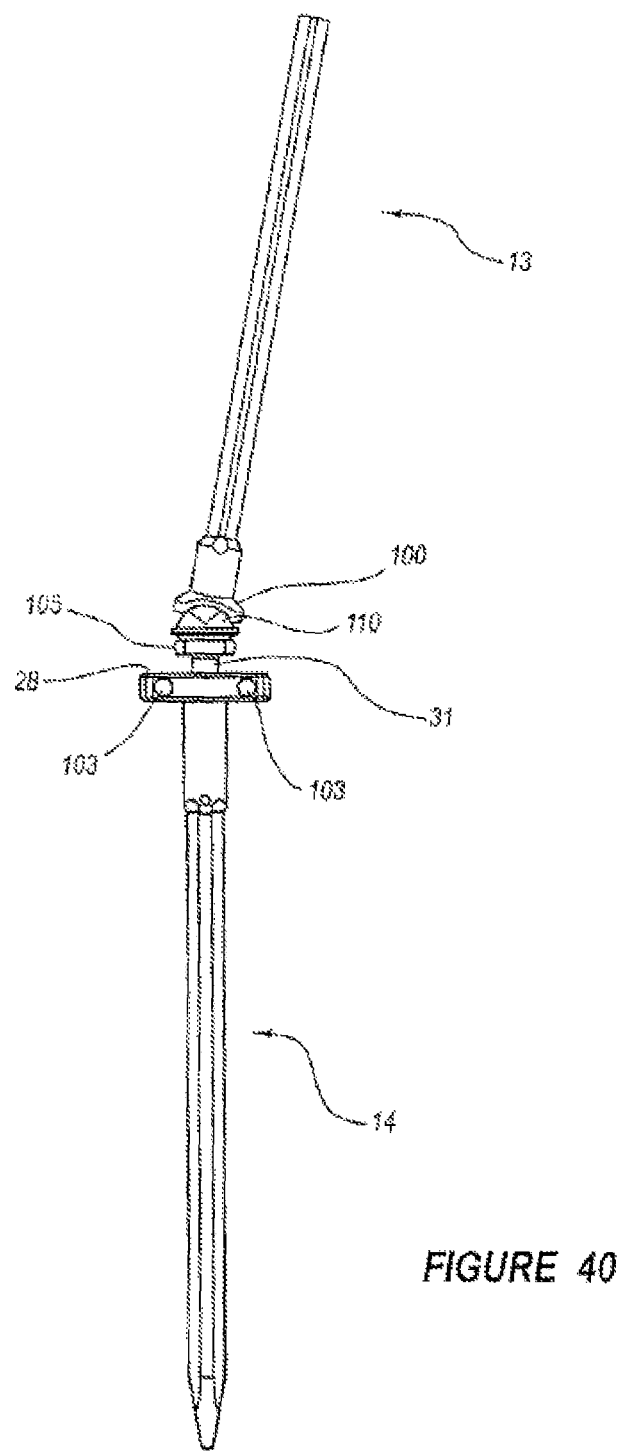

As shown in FIGS. 38 and 39, the tibial IM rod 14 may also include a valgus adapter member 110 or a modified version of femoral mount 15 that has its own post that is configured to insert into the central opening of the hex head bolt 105. As shown in FIG. 40, the valgus adapter member 110 has a convex shape that is configured to extend into the concave shape of the secondary femoral mount 100. This mating allows varus-valgus angulation to position the cuts when the knee is in extension, similar to the first embodiment disclosed above. Extended knee cutting guides can be mounted similar to the flexed knee cutting guide via posts 107.

The assembly 10 of the present invention has many advantages. It provides a relatively narrow and low profile collection of locking components that securely attach cutting guides to tibial and/or femoral IM rods. This provides a robust guide to reference cuts being made to the tibia and the femur with an approach to the joint that minimizes invasiveness. Further, many of the components, such as the first and second locking mechanisms 34, 84 and the quick release mechanism 53, facilitate quick assembly, easy adjustment and quick disassembly for improved efficiency. The use of the bolts 30 and 96 or 105 and the tibial angulation guide 74 or valgus adapter member 110 allow the tibia and femur to be distracted under a matching amount of torque in flexion and extension to ensure a better fit for the tibial and femoral knee replacement components throughout a range of flexion. Also, the tibial angulation guide allows the surgeon to adjust the amount of valgus angulation of the tibia as desired to match the anatomy of the patient.

Figure 41:
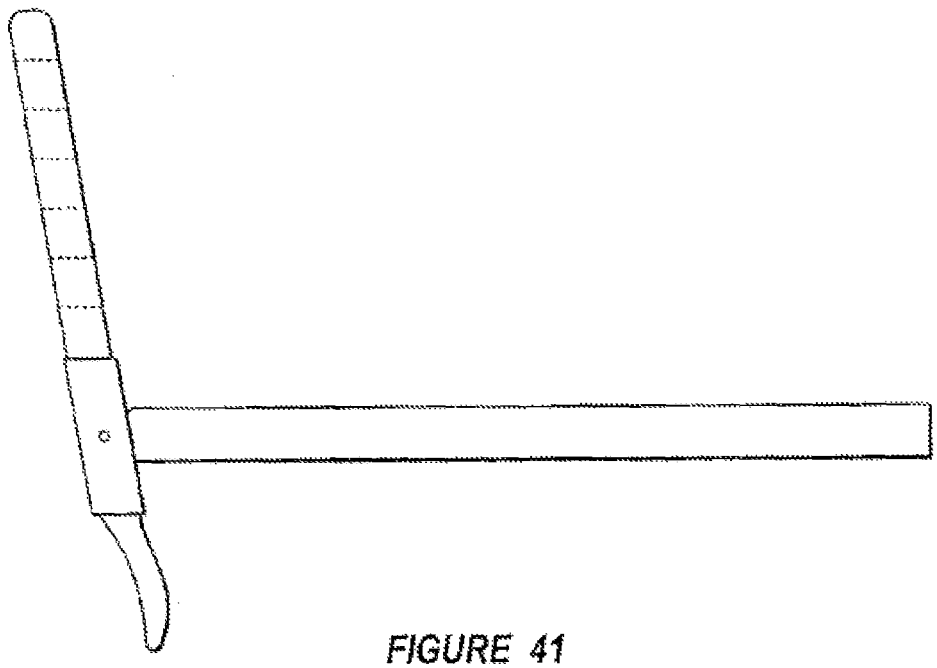
FIG. 41 shows a hinged retractor as used in one embodiment of the present invention.

As shown in FIG. 41, in another embodiment of the present invention a modified femoral mount rod 102 and femoral mount 15 with a hinge mechanism attaching mount 15 to the femoral mount rod 102 could be used with a retractor rod placed thru the hole 18 in the femoral mount 15 and guided posterior to the tibia thus providing a fulcrum and lever arm for the retractor to displace the tibia forward or anterior to allow exposure for placement of the tibial component of the total knee arthroplasty after the bone cuts have been made. Since the IM rods fix rigidly to the bone, other retractors could also be attached to the Guide Assembly to facilitate knee exposure during the knee surgery.

Figure 42:
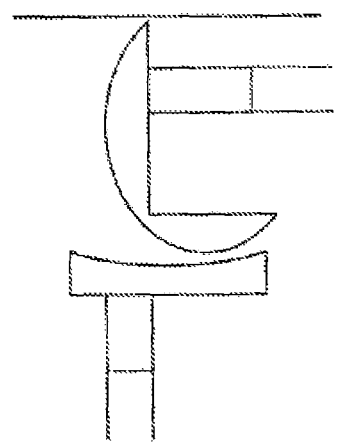
FIG. 42 shows an embodiment of the present invention that implements mini-trials.

As shown in FIG. 42, in another embodiment of the present invention mini-trial components or trial components which are smaller but shaped with identical thickness and radii to the actual knee arthroplasty implants, designed to fit in holes 101 of femoral IM rod 13 and 29 of tibial IM rod 14 and articulate in the center portion of the knee could be used to check alignment and ligament stability prior to placement of the actual final knee arthroplasty implants. This design of a centrally placed mini-knee arthroplasty implant system could become a stand alone total knee arthroplasty. One advantage of this embodiment of the present invention is that the smaller instruments take up less space. The mini-trial femoral component could be designed with cutting surfaces or slots for making the chamfer cuts and other finishing cuts, thus eliminating the need for a chamfer cut block and L-plate 99 shown in FIGS. 30 and 31.

Figure 43:
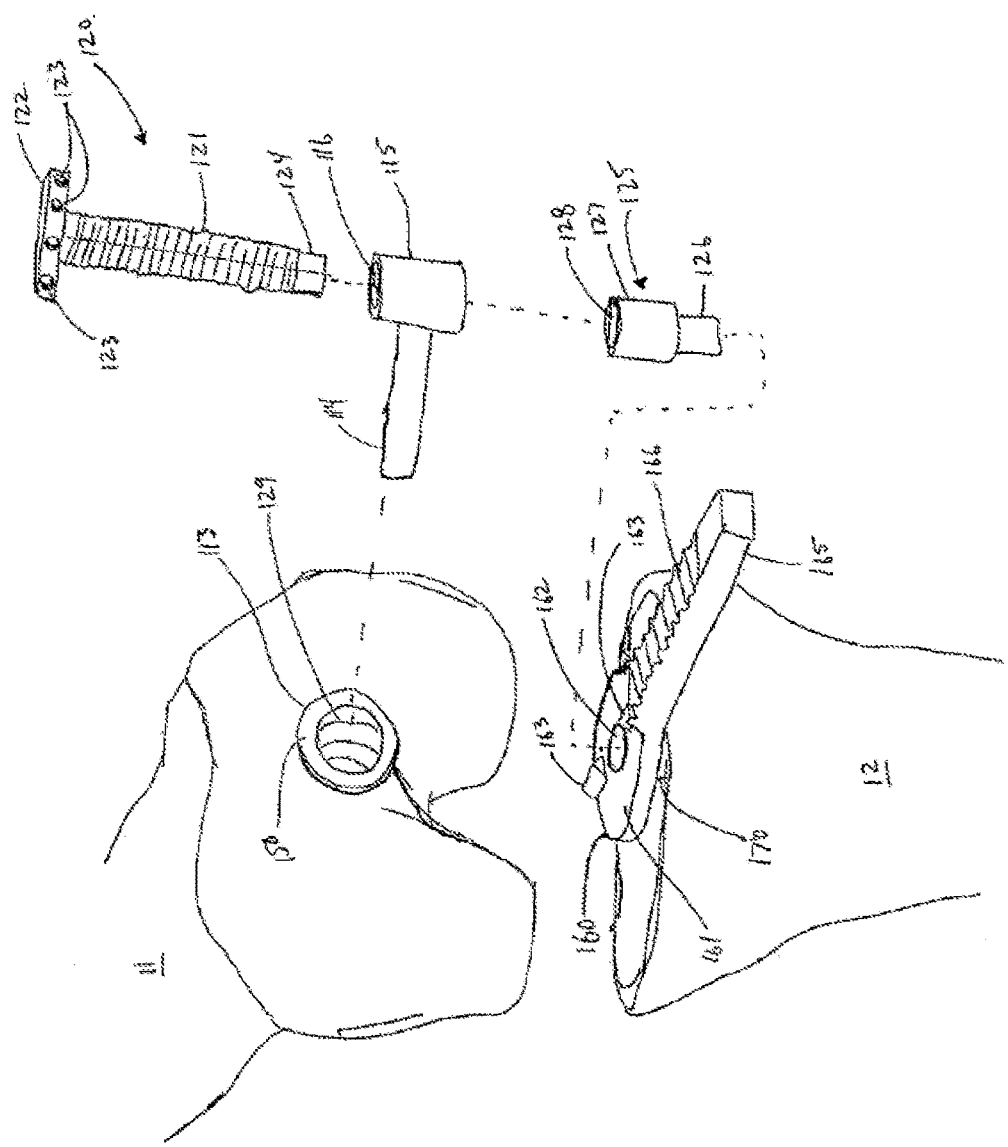
FIG. 43 shows an exploded view of an embodiment of the present invention for resection in knee flexion.
Figure 44:
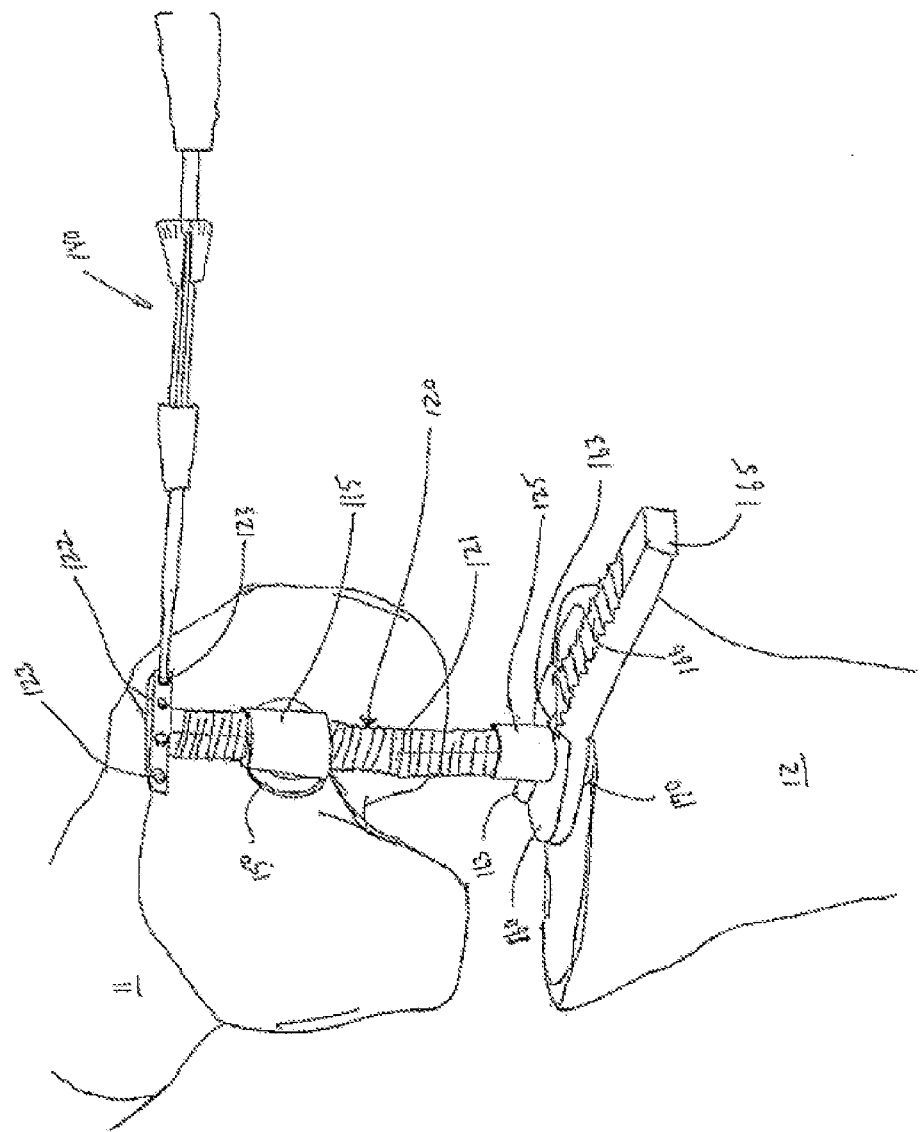
FIG. 44 shows a perspective view of the assembled embodiment of FIG. 43.
Figure 45:
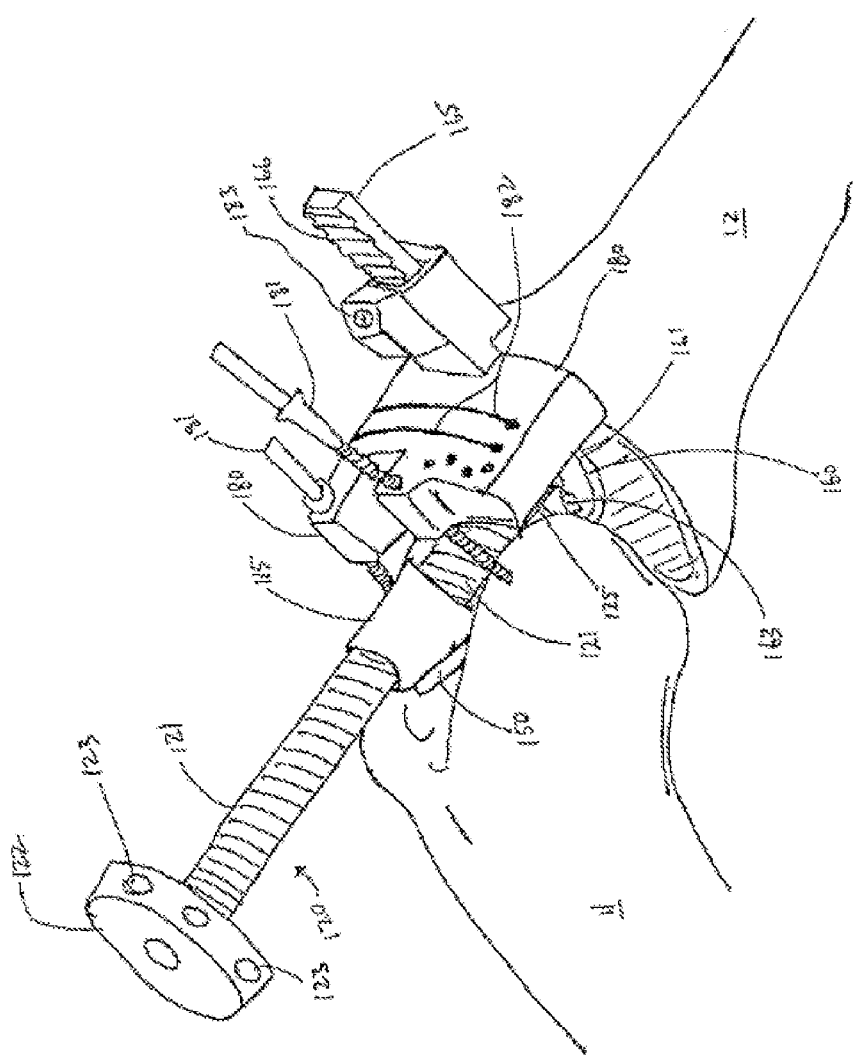
FIG. 45 shows a perspective view of an embodiment of the present invention having the cutting block attached and secured.
Figure 46:
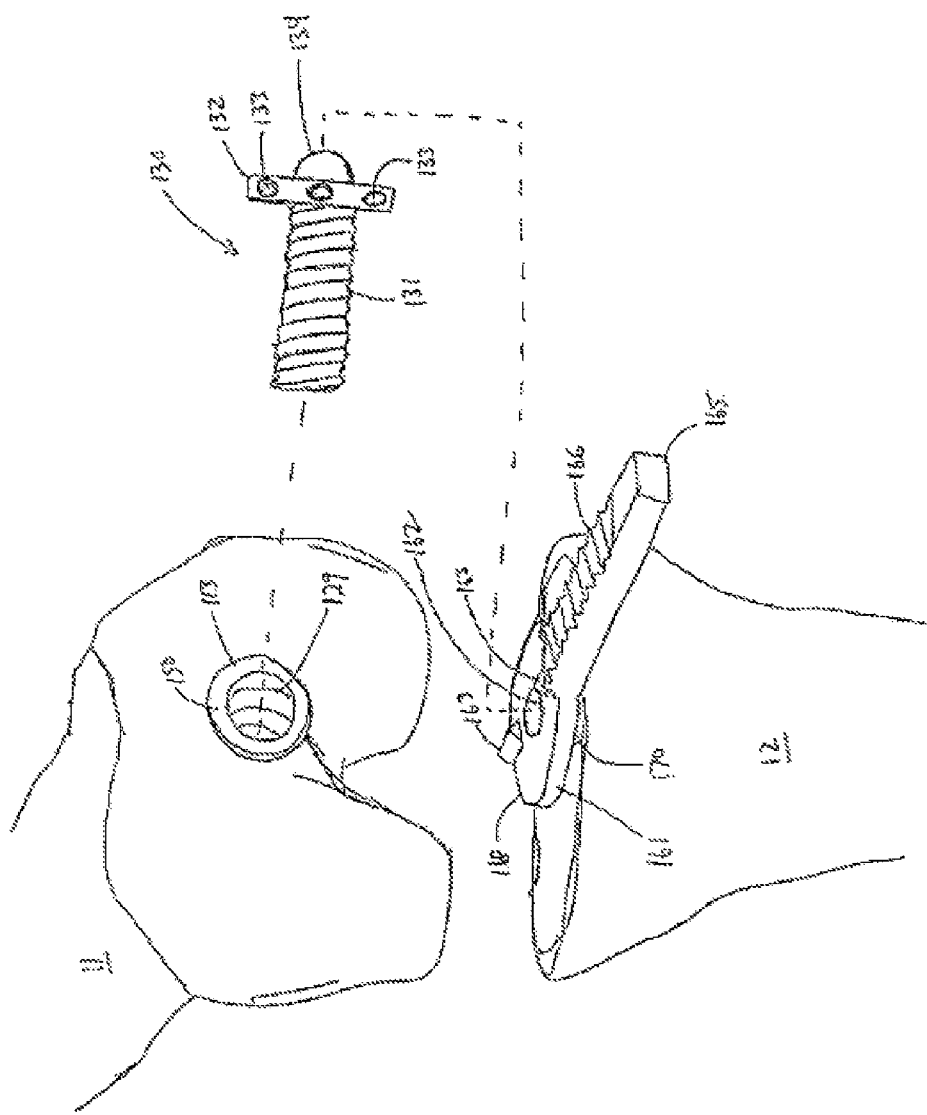
FIG. 46 shows an exploded view of an embodiment of the present invention for resection in knee extension.
Figure 47:
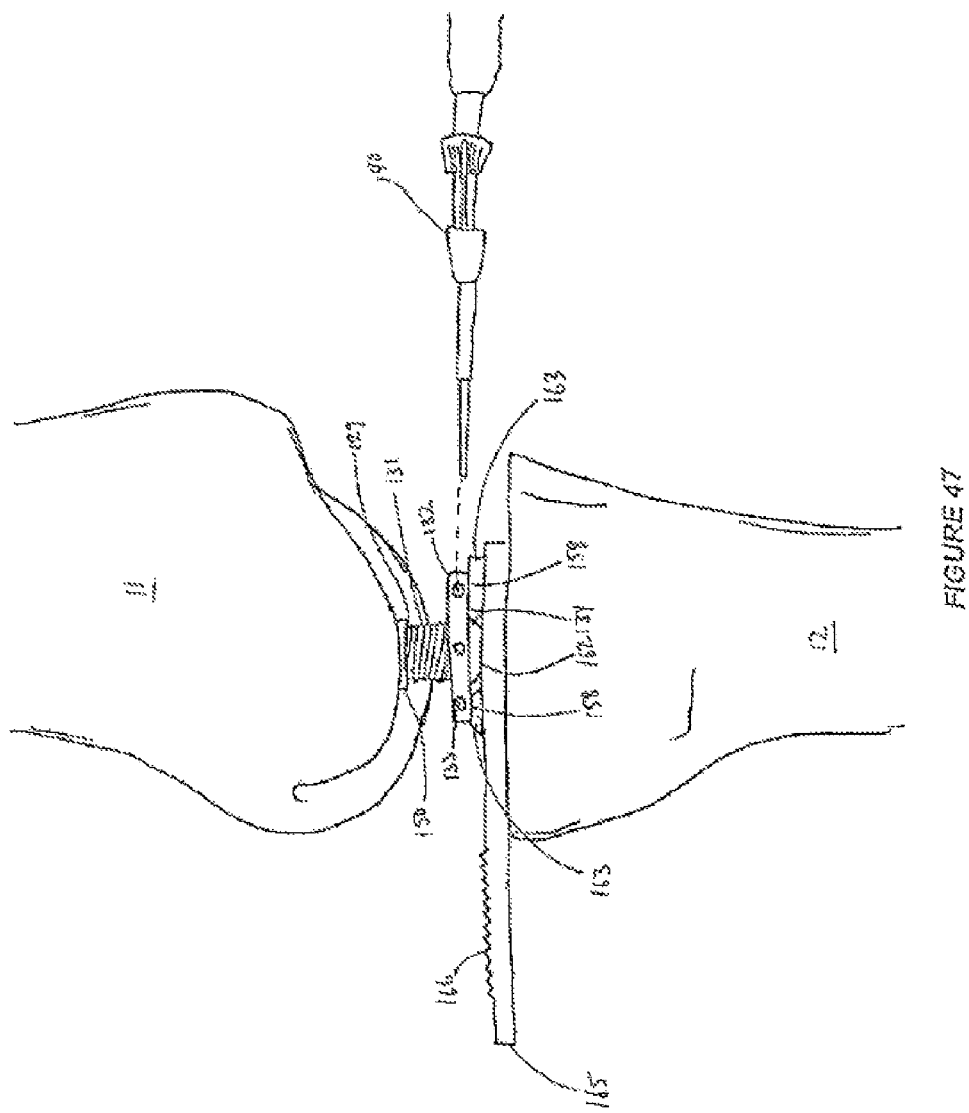
FIG. 47 shows a perspective side view of the assembled embodiment of FIG. 46.
Figure 48:
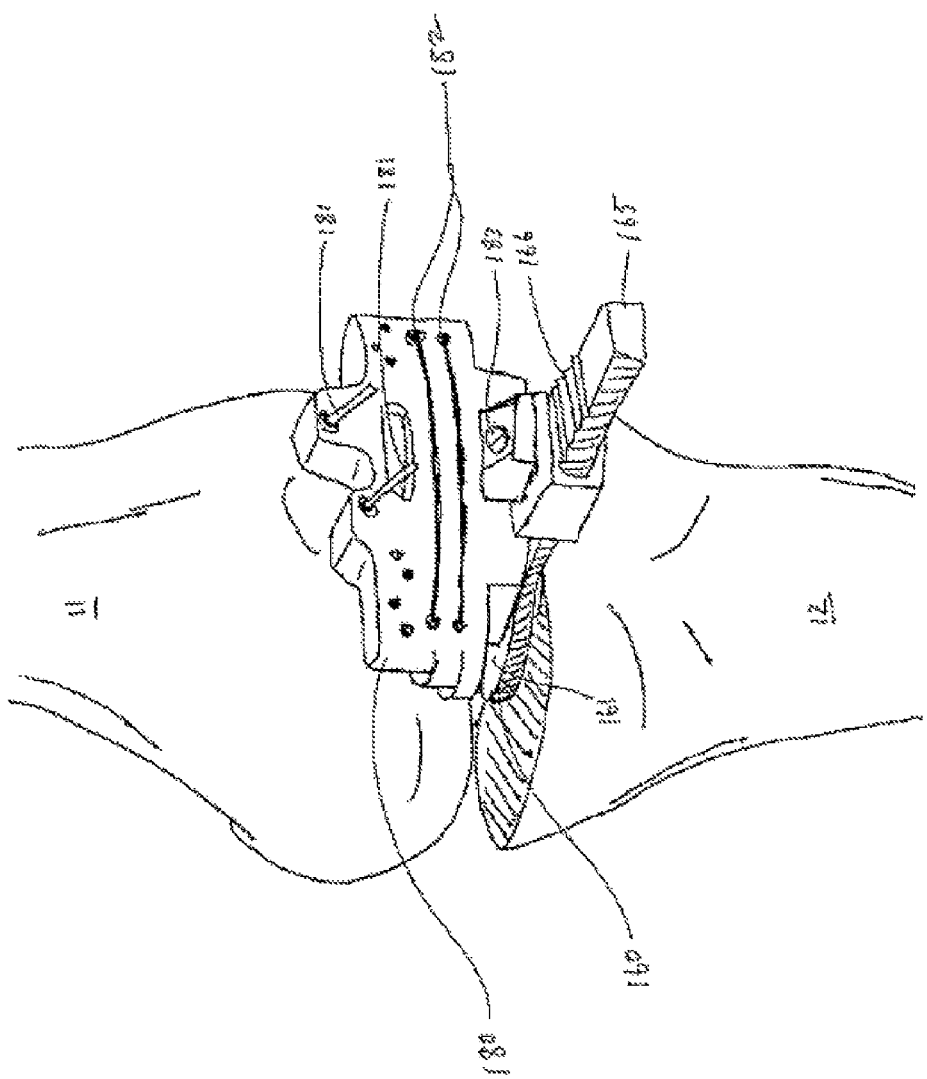
FIG. 48 shows a perspective view of an embodiment of the present invention having the cutting block attached and secured.

Referring now to FIGS. 43-48, another embodiment of the present invention is shown. Specifically, FIGS. 43-45 illustrate an implementation of the current invention for resecting a patient's knee in flexion, and FIGS. 46-48 illustrate an implementation of the current invention for resecting a patient's knee in extension. The femoral mount 150 of the femoral IM rod 113 of each embodiment comprises a planar flange that is substantially inset, and flush with the insertion site of the femur 11. In one embodiment, a rongeur is used to prepare the distal femur for a ⅜ inch drill entry. Following insertion of the drill, a planar is then used to clear the remaining bone from the insertion site and to provide a recessed surface into which the femoral mount 150 is seated. A threaded opening 129 extends into the femoral mount 150 and provides a coupling attachment for an extension bolt 130, which includes a threaded shaft 131, a circular flange 132 with mounting holes 133, and a centralizing ball 134, as shown in FIGS. 46 and 47. Additionally, the threaded opening 129 provides a mounting channel into which a non-threaded post 114 of a threaded barrel 115 is inserted. The interaction between the non-threaded post 114 and the threaded opening 129 sufficiently retains the threaded barrel 115 within the femoral IM rod 113 and permits axial rotation of the threaded barrel 115 relative to the IM rod 113. Axial rotation is desirable to permit limited movement of the surgical tool relative to the natural physiology of the patient's knee. As such, the threaded barrel 115 is permitted to rotate and facilitate the natural alignment of the patient's knee throughout the tensioning process, as described below.

The threaded barrel 115 comprises a non-threaded post 114 perpendicularly coupled to an outer surface of a threaded opening 116. The threaded opening 116 extends through the threaded barrel 15 and provides a coupling attachment for a flexion bolt 120. The flexion bolt 120 includes a threaded shaft 121, a circular flange 122 with mounting holes 123, and a non-threaded tip 124. The threaded shaft 121 compatibly threads through the threaded opening 116 such that the non-threaded tip 124 exits and extends beyond the threaded barrel 115. The circular flange 122 is perpendicularly attached to the threaded shaft 121 opposite the non-threaded tip 124. The flange 122 is circular and generally disk-shaped having a plurality of mounting holes 123 evenly spaced around the circumferential edge of the flange 122. The mounting holes 123 are sized and configured to compatibly receive a torque wrench 140 or other device for turning the flexion bolt 120.

The current embodiment further comprises a tibial tensioning adapter 160. The tibial tensioning adapter 160 is stably supported by the tibial IM rod 170 and positioned generally perpendicular to the main shaft of the tibial IM rod 170. The tibial tensioning adapter 160 comprises a base member 161 and a resection block guide 165. The base member 161 is generally planar and disc-like, having a centrally located opening 162 that extends into the main shaft of the tibial IM rod 170. A bushing 125 is further provided to compatibly seat within the opening 162. The bushing 125 comprises a post portion 126 having a first diameter, and a sleeve portion 127 having a second diameter and an opening 128. The diameter of the post portion 126 is selected to compatibly insert within the opening 162 of the base member 161, while the diameter of the sleeve portion 127 is selected to be greater than the diameter of the opening 162. As such, the sleeve portion 127 rests on the upper surface of the base member 161 and is prevented from inserting into the opening 162. The opening 128 of the sleeve portion 127 is non-threaded and sized to compatibly receive the non-threaded tip portion 124 of the flexion bolt 120. Additionally, the interaction between the post 126 and the opening 162 does not utilize threads thereby allowing the bushing 125 to freely rotate within the opening 162 of the tibial tensioning adapter 160, and allowing the non-threaded tip 124 of the flexion bolt 120 to freely rotate within the opening 128 of the bushing 125. These freely rotating interactions prevent rigid structuring or position of the surgical tools thereby further permitting the natural physiology of the patient's knee to be maintained during the tensioning and resection processes. Thus, the flexion bolt 120, the threaded barrel 115, and the bushing 125 are combined with the femoral mount 150 and the tibial tensioning adapter 160 to apply tension to the patient's knee preparatory to performing the desired resections.

The base 161 further comprises a pair of spacers 163 forming a portion of the base member upper surface. The spacers 163 are generally pyramid shape and linerally configured on opposing sides of the opening 162. The spacers 163 are provided to create a gap between the circular flange 132 of the extension bolt 130 and the upper surface of the base member 161, as shown in FIG. 47. The pyramidal shape of the spacers 163 permits limited radial movement of the extension bolt 130 relative to the base member 161. This limited movement is desirable to accommodate the natural physiology of the patient's knee throughout the tensioning process, described below in connection with FIGS. 46 and 48.

The resection block guide 165 is fixedly coupled to an edge surface of the base member 161 and extends outwardly therefrom. The block guide 165 is generally aligned with the spacers 163 and positioned to extend outwardly from the anterior surface of the knee. The block guide 165 further comprises a plurality of notches 166 occupying an upper surface of the guide 165. The notches 166 span a portion of the upper surface and provide a coupling attachment for a resection block 180, as shown in FIGS. 45 and 48. The notches 166 further provide a plurality of reference points or positions by which to gauge the position of the resection block 180.

Referring now to FIG. 44, an embodiment of the assembled invention is shown. Once the surgical device is assembled, a torque wrench 140 is inserted into a hole 123 of the circular flange 122 and the flexion bolt 120 is rotated. Alternatively, in one embodiment the flexion bolt 120 is initially rotated by hand until the femur 11 begins to lift away from the tibia 12. The torque wrench 140 is then utilized to further rotate the flexion bolt 120 to a desired tension. This will typically result in a final tension of about 10-20 in/lbs. The amount of tension will differ for each patient based on individual physiology, injury, and ligament viscoelasticity of the knee. Once the final tension in flexion has been attained, the final amount of tension placed on the ligaments in is recorded for future reference.

Figure 44A:
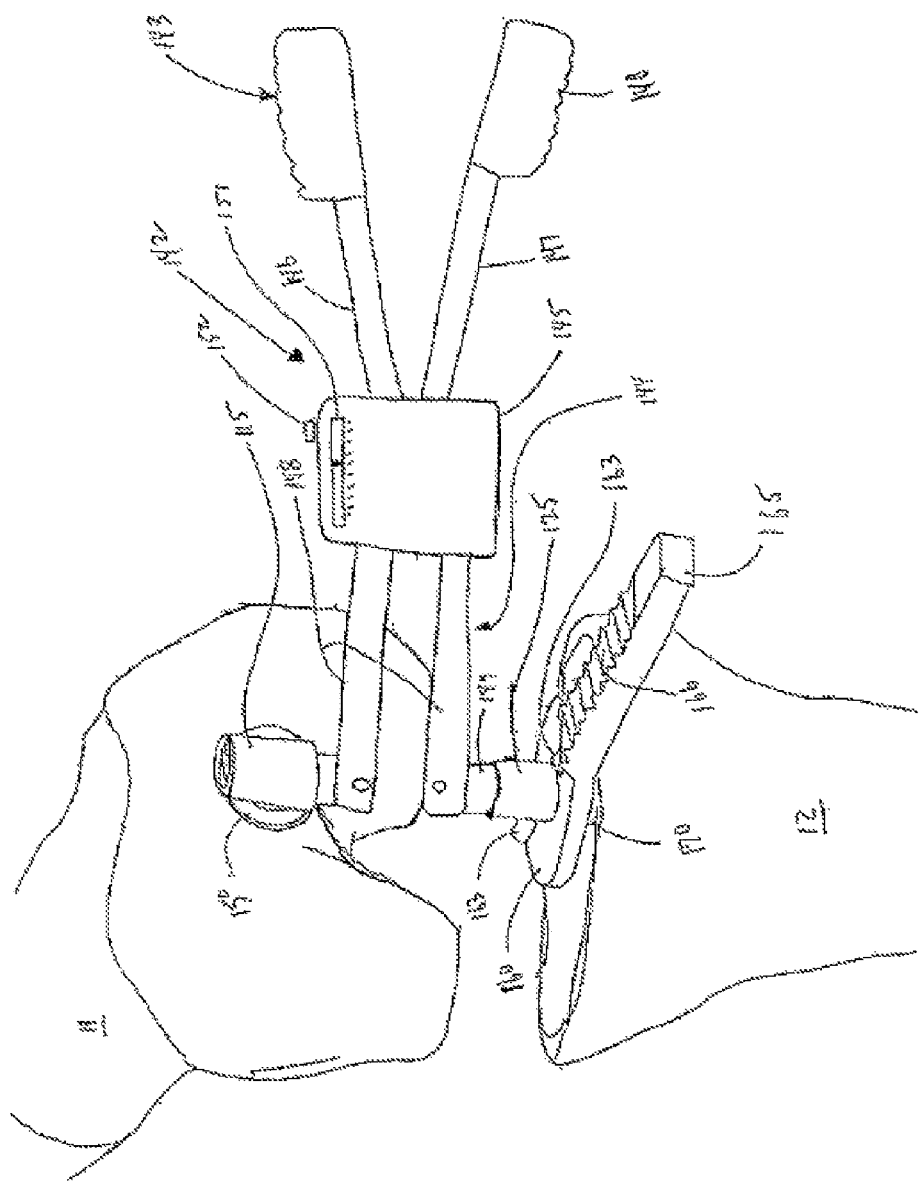
FIG. 44A shows a perspective view of an implementation of the current invention having a ratcheting device in place of the flexion bolt.

Referring now to FIG. 44A, an embodiment of the assembled invention is shown. In this embodiment, the flexion bolt 120 is substituted with a ratcheting device 142. The ratcheting device 142 generally comprises a handle portion 143, a biasing portion 144, and a gear box 145. The biasing portion 144 of the ratcheting device 142 is interposed between the threaded barrel 115 and the bushing 125. The handle portion 143 is then actuated to cause the biasing portion 144 to lift the femur 11 away from the tibia 12. The gear box 145 converts the motion, or actuation of the handle portion 143 to change the position of the biasing portion 144 and separate the knee joint.

The handle portion 143 may include any configuration whereby a physician may manipulate the handle portion 143 to actuate the biasing portion 144 of the device 142. For example, in one embodiment the handle portion 143 comprises a pair of opposing levers 146 and 147, each having a grip 148 at a distal end and extending into the gear box 145 at a proximal end. The biasing portion 144 of the device 142 is actuated by gripping the handle portion 143 and squeezing, such that the pair of opposing levers 146 and 147 is brought to a proximal position. The action of the opposing levers 146 and 147 manipulates the gear box 145 causing the biasing portion 144 to move away from a proximal position. Additionally, in one embodiment the gear box 145 includes a release for returning the biasing portion 144 to a proximal position.

In another embodiment, the handle portion 143 comprises a single shaft having a handle at the distal end, and extending into the gear box 145 at the proximal end. In this embodiment, the biasing portion 144 of the device 142 is actuated by rotating the handle portion 143 in a clockwise or counter-clockwise direction. The rotating action of the handle portion 143 manipulates the gear box 145 causing the biasing portion 144 to move away from, or towards a proximal position. In one embodiment, the gear box 145 further includes a pawl or other device for maintaining the biased position of the biasing portion 144 during use. As such, a physician may actuate the device 142 to separate the knee to a desired position or tension, and then maintain the tension hands-free.

The biasing portion 143 may include any configuration capable of mounting into the threaded barrel 115 and the bushing 125. For example, in one embodiment the biasing portion 143 includes a pair of jaws 148 having a first end for engaging the threaded barrel 115 and the bushing 125, and having a second end extending into the gear box 145. In another embodiment, the first end further includes a jointed connector 149 for engaging the threaded barrel 115 and the bushing 125. The jointed connector 149 permits the pair of jaws 148 to separate the knee joint, yet provide limited movement of the knee joint to accommodate the natural physiology of the patient's knee throughout the tensioning process.

The gear box 145 may include any configuration of gears compatible with the handle portion 143 and the biasing portion 144 to achieve controlled separation of the knee joint. The gear box 145 may also include any means for limiting or measuring the tension placed on the knee joint. For example, in one embodiment the gear box 145 further comprises a tension meter 151 whereby the tension placed on the knee joint, by the ratcheting device, 142 is displayed. In another embodiment, the gear box 145 further comprises an adjusting screw 152 whereby the maximum allowed tension of the ratcheting device 142 is set. In this embodiment, a physician adjusts the adjusting screw 152 to a desired tension. Once set, the physician actuates the ratcheting device 142 to separate the knee joint. When the desired tension is achieved, further tensioning by actuation of the ratcheting device 142 is prevented, thus maintaining the desired tension for the knee.

Referring now to FIG. 45, the resection block 180 is attached to the resection block guide 165 and slid into position against the anterior surface of the femur 11. The resection block 180 is secured to the resection block guide 165 by tightening a set screw 183 against the notches 166 of the guide 165. The resection block 180 is then secured to the femur 11 via a plurality of screws 181. Once the resection block 180 is secured in position, the flexion bolt 120 is removed from the surgical tool assembly and the cutting guides 182 of the resection block 180 are used to resect the exposed distal surfaces of the lateral and medial condyles.

Referring now to FIGS. 46-48, an implementation of the current invention is provided for operation in knee extension. Referring to FIG. 46, the extension bolt 130 is shown prior to being interposed between the femoral mount 150 and the tibial tensioning adapter 160. The extension bolt 130 generally comprises a threaded shaft 131, a circular flange 132 and a centralizing ball 134. The threaded shaft 131 is configured to compatibly thread within the threaded opening 129 of the femoral mount 150. The circular flange 132 is perpendicularly attached to the threaded shaft 131 and interposed between the threaded shaft 131 and the centralizing ball 134. The flange 132 is disk shaped having a plurality of mounting holes 133 evenly space around the circumferential edge of the flange 132. The mounting holes 133 are sized and configured to compatibly receive a torque wrench 140 or other device for turning the extension bolt 130.

The centralizing ball 134 comprises a hemispherically shaped surface that is sized and configured to partially insert within opening 162 of the tibial tensioning adapter 160. As such, the centralizing ball 134 partially engages the opening 162 yet remains sufficiently free to provide axial rotation between the femur 11 and the tibia 12. The interface between the centralizing ball 134 and the opening 162 further ensures accurate alignment of the femoral mount 150 with the tibial tensioning adapter 160. Radial rotation is further provided to the femur 11 and the tibia 12 due to the interface 158 between the circular flange 132 and the spacers 163, as previously discussed and as shown in FIG. 47. Thus, the extension bolt 130 provides both alignment and limited free adjustment to the femur 11 and tibia 12 during the tensioning and resection procedures.

In one embodiment, the extension bolt 130 is first coupled to the femoral mount 150 by threading the threaded shaft 131 into the threaded opening 129 of the femoral mount 150, with the knee in flexion, as shown in FIG. 46. The extension bolt 130 is maximally inserted into the threaded opening 129 to minimize the distance between the femur 11 and the tibia 12. The knee is then brought into extension and the centralizing ball 134 is inserted into opening 162, as shown in FIG. 47. A torque wrench 140 is then utilized to rotate the extension bolt 130 and apply tension the knee. The torque wrench 140 is inserted into a hole 133 of the circular flange 132 and turned to gradually remove the extension bolt 130 from the threaded opening 129. In one embodiment, the physician immobilizes the resection block guide 165 to prevent rotation of the tibia 12 during rotation of the extension bolt 130. The physician continues to turn the extension bolt 130 until the desired tension is placed on the ligaments of the knee. Alternatively, a ratcheting device (see FIG. 44A) may be used with the knee in extension to place the desired tension on the ligaments of the knee. In one embodiment, the final tension in extension is equal to the final tension in flexion. In another embodiment, the final tension in extension is different than the final tension in flexion.

Referring now to FIG. 48, the resection block 180 is attached to the resection block guide 165 and slid into position against the anterior surface of the femur 11, as discussed above in connection with FIG. 45. Once positioned, the resection block 180 is secured to the femur 11 with screws 181 and the anterior surfaces of the lateral and medial condyles are resectioned.

In another embodiment, since the guide assembly is fixed rigidly to the bone and left in place during the essential steps of the knee preparation, computer assisted guides are attached to the guide assembly instruments thus facilitating computer assisted total knee replacement. In other embodiments of the present invention, the guide assembly instruments are modified for use in a partial or unicompartmental knee arthroplasty procedure.

In some embodiments, the Guide Assembly Instruments can be modified for use with short IM rods or a tibial platform instead of an IM rod for extramedullary knee preparation.

In some embodiments, the Guide Assembly holds a patient's leg in place. This decreases the need for medical assistants to hold the patient's leg.

Figure 49:
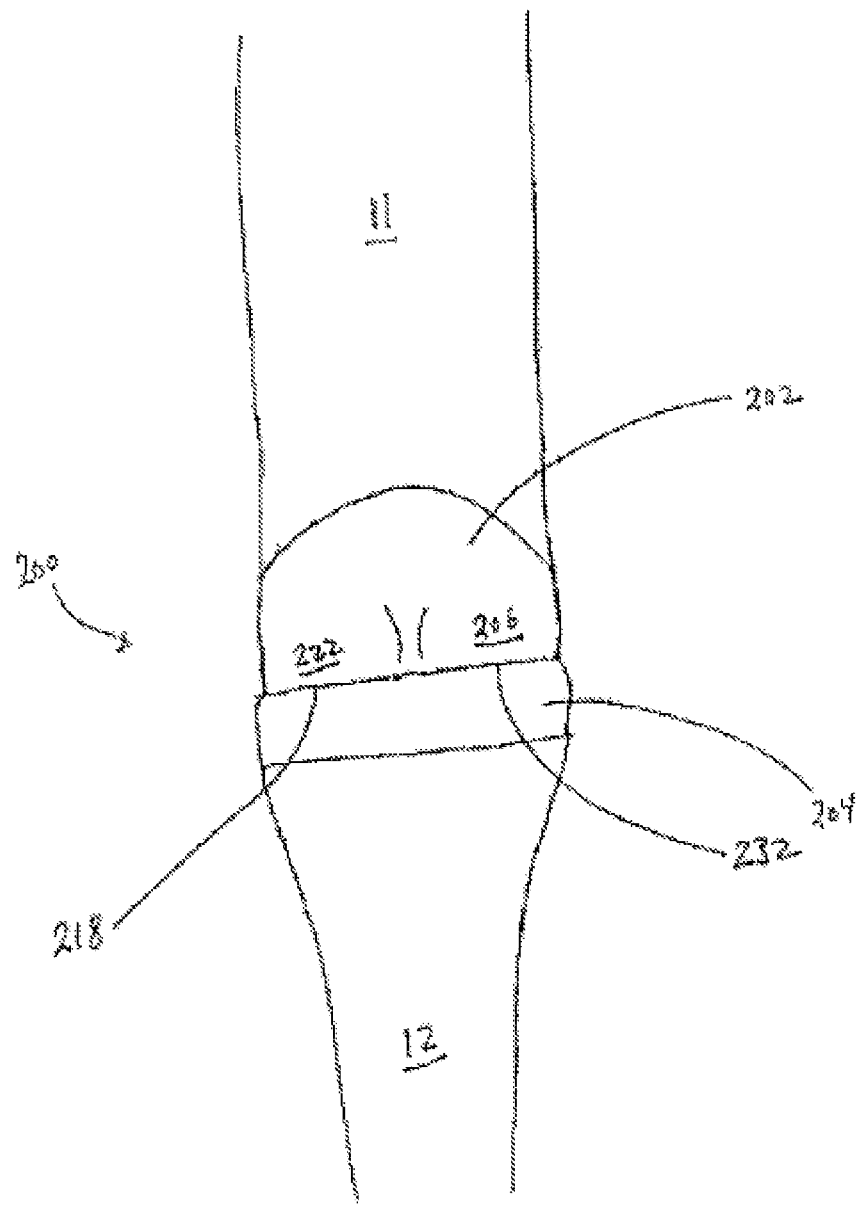
FIG. 49 shows a perspective front view of an embodiment of the resectioned knee having been fitted with a knee prosthesis.
Figure 50:
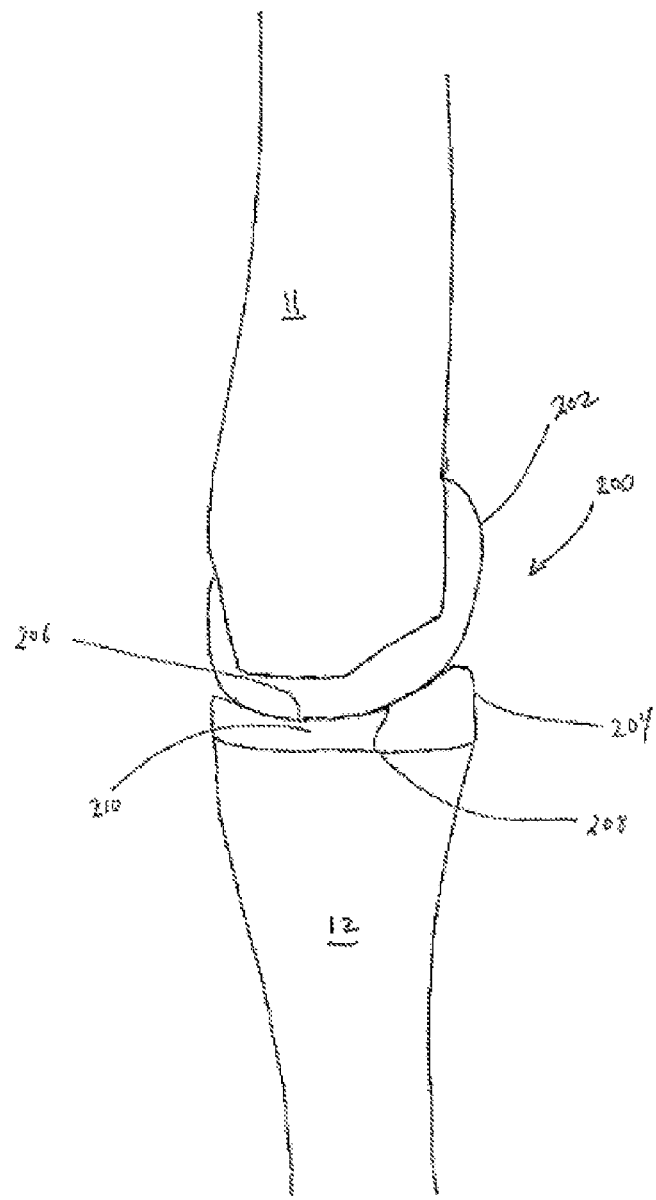
FIG. 50 shows a perspective side view of the embodiment of FIG. 49.

Following a completed resection of the patient's knee joint, the resectioned portions of the femur 11 and the tibia 12 are replaced by a knee prosthesis or implant 200, such as shown in FIGS. 49 and 50. The knee implant 200 generally comprises a femoral component 202 and a tibial component 204. Although the instruments of the invention can be used with any type of knee prosthesis 200, the instruments are particularly well-suited for use in accurately resecting the knee for receipt of a knee prosthesis that employs a constant radius throughout the primary range of flexion, such as Wright Medical Technology, Inc.'s ADVANCE® medial pivot knee implant. The features and characteristics of constant radius knee prostheses are well known to those of skill in the art, but have not previously been used with knee tensioning resection instruments. As will be described below, a synergistic and previously unappreciated effect is obtained by using the tensioning instruments in combination with prior art constant radius knee implants. It is anticipated that the end result of this synergistic combination will be greater overall accuracy in the implantation of constant radius knee implants, with resulting improvements in clinical outcomes.

One of the benefits of a properly designed and implanted constant radius knee prosthesis is that it provides the patient with constant ligament tension throughout the primary range of flexion. As discussed herein, the use of the instruments of the invention to resect the knee while under optimum tension helps insure accurate placement of the knee implant components. The combined use of tensioning instruments and constant radius knee implants improves the likelihood of achieving constant ligament tension throughout the primary range of flexion. Various embodiments of knee implants that incorporate a constant radius are discussed in the following prior art documents, which are incorporated herein by reference: U.S. Pat. Nos. 7,261,740; 6,013,103; 6,013,103; 5,824,100; 5,330,533; 5,326,361; 5,314,482; 5,219,362; 5,133,758; 4,085,466; German Patent Application 3314038A1.

Figure 51:
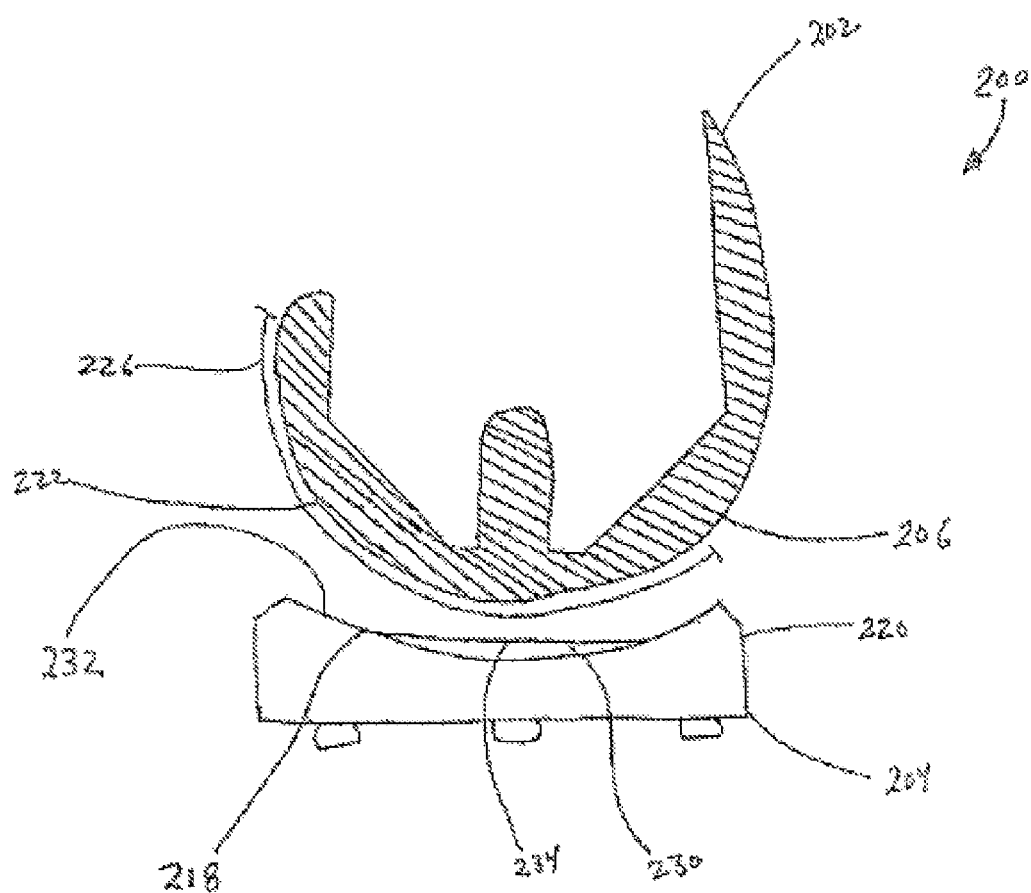
FIG. 51 shows a partially cross-sectioned view of an implementation of the knee prosthesis.

In the prior art ADVANCE® Medial Pivot knee implant, the femoral component 202 has a spherical condyle 206 on the medial side. As indicated in FIG. 51, in the sagittal or A-P plane, the medial femoral condyle 206 has a constant radius 226 over at least the primary range of flexion, which extends from about 0 degrees in extension to about 90 degrees in flexion, depending on the patient. The lateral femoral condyle 222 also has an A-P constant radius 226 throughout the primary range of flexion. The medial side of the tibial base 204 of the ADVANCE® Medial Pivot knee has a shallow spherically concave bearing surface 232, which is sized to closely receive the medial femoral condyle 206 in a ball-and-socket manner. The lateral side of the tibial base 204 is generally in the form of an elongated arcuate trough 230. These features allow the medial femoral condyle 206 to pivot in the medial tibial bearing 232 during flexion, while simultaneously permitting the lateral femoral condyle 222 to translate posteriorly in the lateral tibial bearing 218. This action is designed to mimic the function of the natural knee, in which the medial femoral condyle exhibits less rollback than the lateral condyle during motion. Features and characteristics of the ADVANCE® Medial Pivot knee are discussed in greater detail in U.S. Pat. Nos. 5,964,808 and 6,013,103, which are incorporated herein by reference. Although the ADVANCE® Medial Pivot knee implant is an exemplary implant design for optimizing and complementing the use of the tensioning instruments of the invention, other constant radius knee implant designs can be used to similar or equal effect.

One of the drawbacks of prior art knee instruments is that overstuffing or under filling the joint sometimes occurs, with resulting tightness or laxity, respectively, in the ligaments. As discussed above, use of the tensioning instruments to resect with the knee tensed in the extended position allows the user to make a balanced extension gap resection when compared with the tensed resections made with the knee previously positioned in flexion. The resection cuts are made off of a single reference point, the single reference point being the desired amount of tension. The use of equal flexion and extension gaps automatically balances the mid-flexion gap at all points in between. By then implanting a constant radius knee implant onto the resectioned knee, the surgeon effectively transfers the optimum tension obtained by the tensioning instruments to the constant radius knee implant, resulting in a stable, smoothly functioning knee throughout at least the primary range of flexion. In mechanical terms, the tensioning technique preloads the bearing, the bearing being the constant radius knee implant.

In contrast, if a conventional J-curve or varying radius knee implant is used with the tensioning technique, rather than a constant radius implant, it becomes necessary to vary the cuts instead of using an equal flexion and extension gap. The use of a varying radius knee implant thus necessarily complicates the process and the use of the instruments.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An apparatus for adjusting at least one of: (i) tension and (ii) an alignment of a knee joint, the apparatus comprising:
   a first member configured to extend into a femur when the apparatus is seated in the knee joint;
   a second member that is configured to be seated at a proximal portion of a tibia when the apparatus is seated in the knee joint; and an adjustable component that is configured to couple the first member with the second member such that the second member is rotatable about a longitudinal axis of the first member when a position of the first member is constant with respect to the femur to allow for adjustment of an angle between the tibia and the femur when the apparatus is seated in the knee joint.

2. The apparatus of claim 1, further comprising a femoral element defining an opening that is configured to extend into the femur when the femoral element is seated in the knee joint, and wherein the first member is configured to extend into the opening in the femoral element when the first member is seated in the knee joint.

3. The apparatus of claim 2, wherein the adjustable component comprises a threaded object that is configured to be rotated to vary a distance between the first member and the second member when the apparatus is seated in the knee joint, and wherein the apparatus is configured to be seated in the knee joint with the first member extended into the femur and the second member seated at the proximal portion of the tibia when the knee joint is disposed in a flexed position.

4. The apparatus of claim 3, wherein a longitudinal axis of the threaded element is runs perpendicularly with respect to the longitudinal axis of the first member when the apparatus is seated in the knee joint.

5. The apparatus of claim 1, wherein the first member comprises an intramedullary rod and wherein the adjustable component is configured to couple the second member to the intramedullary rod such that the second member is rotatable about a longitudinal axis of the intramedullary rod when the apparatus is seated in the knee joint.

6. The apparatus of claim 5, further comprising a femoral element defining an opening, wherein a portion of the femoral element and the opening are configured to be disposed in a distal portion of a femur and wherein the intramedullary rod extends into the femoral element when the apparatus is seated in the knee joint.

7. An apparatus for adjusting at least one of: (i) tension and (ii) an alignment of a knee joint, the apparatus comprising:
an elongated member that is configured to extend into a distal end of a femur;
a tibial contact member that is configured to contact a proximal end of a tibia; and
an adjustable component that connects the elongated member with the tibial contact member such that the tibial contact member is rotatable about a longitudinal axis of the elongated member when the apparatus is seated in the knee joint, when the elongated member is fixed in position with respect to the femur, and when the knee joint is in a flexed position.

8. The apparatus of claim 7, wherein the adjustable component comprises a threaded element that is configured to be rotated to vary a distance between the elongated member and the tibial contact member when the elongated member extends into the distal end of the femur and the tibial contact member contacts the proximal end of the tibia.

9. The apparatus of claim 8, wherein a longitudinal axis of the threaded element is configured to run substantially perpendicular to the longitudinal axis of the elongated member when the apparatus is seated in the knee joint with the elongated member extending into the distal end of the femur and the tibial contact member contacting the proximal end of the tibia.

10. The apparatus of claim 8, further comprising a femoral element defining an opening, wherein a portion of the femoral element and the opening are configured to be disposed in a distal portion of the femur and wherein the elongated member is configured to extend into the femoral element when the apparatus is seated in the knee joint.

11. The apparatus of claim 10, wherein the adjustable component comprises a threaded object that is configured to be rotated to vary a distance between the elongated member and the tibial contact member when the elongated member extends into the distal end of the femur and the tibial contact member contacts the proximal end of the tibia, and wherein a longitudinal axis of the threaded element is configured to run substantially perpendicular to the longitudinal axis of the elongated member when the apparatus is seated in the knee joint with the rod extending into the distal end of the femur and the tibial contact member contacting the proximal end of the tibia.

12. An apparatus for adjusting at least one of: (i) tension and (ii) an alignment of a knee joint, the apparatus comprising:
a femoral element defining an opening, wherein a portion of the femoral element and the opening are configured to extend into a distal portion of a femur when the femoral element is seated in the knee joint;
a elongated member that is configured to be received within the opening such that a portion of the elongated member extends into the femur when the femoral element is placed in the distal end of the femur and the elongated member is inserted into the femoral element; and
a tibial contact member that is configured to contact a proximal end of a tibia when the apparatus is seated in the knee joint,
wherein the elongated member and the tibial contact member are configured to couple together when the apparatus is seated in the knee joint such that the tibial contact member is rotatable with respect to the femur to allow for adjustment of an angle between the tibia and the femur when the apparatus is seated in the knee joint.

13. The apparatus of claim 12, further comprising an adjustment mechanism that couples the elongated member to the tibial contact member, and wherein a portion of the adjustment mechanism is configured to be twisted to vary a distance between the elongated member and the tibial contact member.

14. The apparatus of claim 13, wherein the adjustment mechanism comprises a threaded element that is configured to be rotated to vary a distance between the elongated member and the tibial contact member when the apparatus is seated in the knee joint, and wherein a longitudinal axis of the threaded element is configured to run substantially perpendicular to a longitudinal axis of the elongated member when the apparatus is seated in the knee joint.

15. The apparatus of claim 14, wherein the elongated member comprises a rod that is configured to extend into an intramedullary portion of the femur, and wherein the apparatus is configured to be seated in the knee joint when the knee joint is disposed in a flexed position.

16. The apparatus of claim 12, wherein the elongated member comprises a rod that is configured to extend into an intramedullary portion of the femur, and wherein the apparatus is configured to be seated in the knee joint when the knee joint is disposed in a flexed position.

17. The apparatus of claim 12, wherein the tibial contact member is coupled to the femoral element such that the tibial contact member is rotatable around a longitudinal axis of the femoral element when the femoral element is fixed in location with respect to the femur.

\* \* \* \* \*